United States Patent
Benting et al.

(10) Patent No.: US 9,617,286 B2
(45) Date of Patent: Apr. 11, 2017

(54) FUNGICIDE N-[(TRISUBSTITUTEDSILYL) METHYL]-CARBOXAMIDE DERIVATIVES

(71) Applicants: Juergen Benting, Leichlingen (DE); Pierre Cristau, Lyons (FR); Philippe Desbordes, Lyons (FR); Helene Lachaise, Lyons (FR); Philippe Rinolfi, Chatillon-d'Azergues (FR)

(72) Inventors: Juergen Benting, Leichlingen (DE); Pierre Cristau, Lyons (FR); Philippe Desbordes, Lyons (FR); Helene Lachaise, Lyons (FR); Philippe Rinolfi, Chatillon-d'Azergues (FR)

(73) Assignee: BAYER INTELLECTUAL PROPERTY GMBH (DE)

( * ) Notice: Subject to any disclaimer, the term of this patent is extended or adjusted under 35 U.S.C. 154(b) by 0 days.

(21) Appl. No.: 14/359,370

(22) PCT Filed: Nov. 20, 2012

(86) PCT No.: PCT/EP2012/004801
§ 371 (c)(1),
(2) Date: May 20, 2014

(87) PCT Pub. No.: WO2013/075817
PCT Pub. Date: May 30, 2013

(65) Prior Publication Data
US 2014/0315858 A1    Oct. 23, 2014

Related U.S. Application Data

(60) Provisional application No. 61/567,201, filed on Dec. 6, 2011.

(30) Foreign Application Priority Data

Nov. 21, 2011  (EP) .................................... 11356014

(51) Int. Cl.
*C07F 7/08* (2006.01)
*A01N 55/00* (2006.01)
(52) U.S. Cl.
CPC ............ *C07F 7/0812* (2013.01); *A01N 55/00* (2013.01); *C07F 7/0818* (2013.01)

(58) Field of Classification Search
CPC ..................................................... C07F 7/0812
See application file for complete search history.

(56) References Cited

U.S. PATENT DOCUMENTS

| | | | |
|---|---|---|---|
| 5,384,312 A | 1/1995 | Schirlin et al. | 514/63 |
| 5,529,988 A | 6/1996 | Schirlin et al. | 514/63 |
| 5,532,397 A | 7/1996 | Schirlin et al. | 556/413 |
| 7,087,776 B2* | 8/2006 | Sieburth et al. | 556/400 |
| 8,841,332 B2 | 9/2014 | Bennabi et al. | 514/361 |
| 2009/0298890 A1 | 12/2009 | Coqueron et al. | 514/351 |

FOREIGN PATENT DOCUMENTS

| | | |
|---|---|---|
| CN | 102119150 A | 7/2011 |
| WO | WO 95/29154 | 11/1995 |
| WO | WO 2008/003744 | 1/2008 |
| WO | WO 2010/012795 A1 | 2/2010 |

OTHER PUBLICATIONS

International Search Report issued Jan. 7, 2013 in corresponding International Application No. PCT/EP2012/004801.

* cited by examiner

*Primary Examiner* — Brian McDowell
(74) *Attorney, Agent, or Firm* — Ostrolenk Faber LLP

(57) ABSTRACT

The present invention relates to fungicidal N-[(trisubstitutedsilyl)methyl]carboxamide or its thiocarboxamide derivatives with formula:

$$\begin{array}{c} Z^3 \ Z^4 \ Z^7 \\ B \underset{Z^1 \ Z^2}{\overset{\phantom{x}}{\diagdown}} \underset{n}{\overset{\phantom{x}}{\diagup}} Si \underset{Z^5 \ Z^6}{\overset{\phantom{x}}{\diagdown}} \underset{\phantom{x}}{\overset{\phantom{x}}{\diagup}} N \underset{T}{\overset{\phantom{x}}{\diagdown}} A \end{array} \quad (I)$$

their process of preparation and intermediate compounds for their preparation, their use as fungicides, particularly in the form of fungicidal compositions and methods for the control of phytopathogenic fungi of plants using these compounds or their compositions.

15 Claims, No Drawings

FUNGICIDE N-[(TRISUBSTITUTEDSILYL) METHYL]-CARBOXAMIDE DERIVATIVES

CROSS-REFERENCE TO RELATED APPLICATION(S)

The present application is a 35 U.S.C. §371 national phase conversion of PCT/EP2012/004801 filed on Nov. 20, 2012, which claims priority of European Application No. 11356014.8 filed on Nov. 21, 2011 and U.S. Provisional Application No. 61/567,201 filed on Dec. 6, 2011. Applicants claim priority to each of the foregoing patent applications. The PCT International Application was published in the English language.

DESCRIPTION

The present invention relates to fungicidal N-[(trisubstitutedsilyl)methyl]carboxamide or its thiocarboxamide derivative, their process of preparation and intermediate compounds for their preparation, their use as fungicides, particularly in the form of fungicidal compositions and methods for the control of phytopathogenic fungi of plants using these compounds or their compositions.

In international patent application WO-1995/029154 certain (thio)ureas or (thio)carbamates derivatives, acting as squalene epoxidase inhibitors, are generically embraced in a broad disclosure of numerous compounds of the following formula:

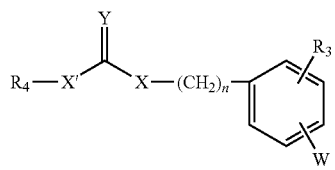

wherein Y can represent an oxygen or a sulfur atom, X and X' can independently represent an oxygen atom or a substituted or non-substituted nitrogen atom, n can be 0, $R_3$ can be a hydrogen atom, a halogen atom or a $C_1$-$C_6$-alkyl group, W represents a mono or disubstituted aminomethyl group and $R_4$ can represent among many other groups, a substituted [di-$C_1$-$C_6$-alkyl(phenyl)silyl]methyl group. However, this document does not disclose compounds wherein the (thio)urea or the (thio)carbamate can be replaced by a (thio)amide. Furthermore, there is no disclosure in this document of any compound wherein W can represent hydrogen and R¹can represent a halogen atom or a $C_1$-$C_6$-alkyl group.

In international patent application WO-2007/1039615 certain fungicidal N-[(trialkylsilyl)alkyl]carboxamide derivatives are generically embraced in a broad disclosure of numerous compounds of the following formula:

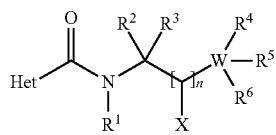

wherein Het can represent a 5-membered heterocyclic ring, n can be 2 to 4, $R^1$ can represent a hydrogen atom, a $C_1$-$C_6$-alkyl group or a $C_3$-$C_7$-cycloalkyl group, W can represent a silicon atom, X and $R^3$ can represent a hydrogen atom or a $C_1$-$C_6$-alkyl group, $R^2$, $R^4$, $R^5$ and $R^6$ can represent various substituents among which a $C_1$-$C_6$-alkyl group. However, this document does not disclose compounds wherein Het can be an unsaturated or partially saturated, 6-membered heterocyclyl group. Furthermore, there is no disclosure in this document of any compound wherein one of the three substituent $R^4$, $R^5$ or $R^6$ can be a (hetero) aromatic ring and n can be 0.

In international patent application WO-2008/003744 certain fungicidal N-[(dialkyl-2-pyridylsilyl)methyl]carboxamide derivatives are generically embraced in a broad disclosure of numerous compounds of the following formula:

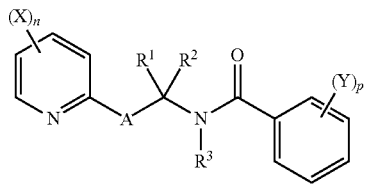

wherein A can represent a $SiR^4R^5$ group, $R^3$ can represent a hydrogen atom, a $C_1$-$C_6$-alkyl group or a $C_3$-$C_7$-cycloalkyl group, $R^1$ and $R^2$ can represent various substituents among which a hydrogen atom or a $C_1$-$C_6$-alkyl group, and $R^4$ and $R^5$ can represent a $C_1$-$C_6$-alkyl group. However, this document does not disclose compounds wherein the 2-pyridine moiety can be replaced by a phenyl group or any other heterocyclyl group. Furthermore, there is no explicit disclosure in this document of any compound wherein A can be a dialkylsilyl group.

In international patent application WO-2008/081011 certain fungicidal N-[(dialkyl-2-pyridylsilyl)methyl]carboxamide derivatives are generically embraced in a broad disclosure of numerous compounds of the following formula:

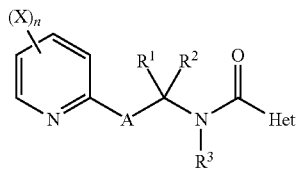

wherein Het can represent a 6-membered non fused heterocyclic ring, A can represent a $SiR^4R^5$ group, $R^3$ can represent a hydrogen atom, a $C_1$-$C_6$-alkyl group or a $C_3$-$C_7$-cycloalkyl group, $R^1$ and $R^2$ can represent various substituents among which a hydrogen atom or a $C_1$-$C_6$-alkyl group, and $R^4$ and $R^5$ can represent a $C_1$-$C_6$-alkyl group. However, this document does not disclose compounds wherein the 2-pyridine moiety can be replaced by a phenyl group or any other heterocyclyl group. Furthermore, there is no explicit disclosure in this document of any compound wherein A can be a dialkylsilyl group.

In international patent application WO-2010/012795 certain fungicidal N-[(dialkyl-2-phenylsilyl)ethyl]carboxamide derivatives are generically embraced in a broad disclosure of numerous compounds of the following formula:

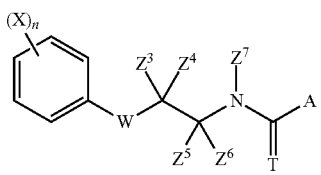

wherein A can represent a 5-membered heterocyclic ring, T can represent an oxygen atom or a sulfur atom, W can represent a $SiZ^1Z^2$ group, $Z^7$ can represent a $C_3$-$C_7$-cycloalkyl group, $Z^1$ and $Z^2$ can represent a $C_1$-$C_8$-alkyl group, and $Z^3$, $Z^4$, $Z^5$ and $Z^6$ can represent various substituents among which a hydrogen atom or a $C_1$-$C_8$-alkyl group. However, this document does not disclose compounds wherein A can be a phenyl group or an unsaturated or partially saturated, 6-membered heterocyclyl group. Furthermore, this document does not disclose compounds wherein the $SiZ^1Z^2$ group can be linked to the (thio)carboxamide moiety by a unique methylene group or wherein $Z^7$ can represent a hydrogen atom or a $C_1$-$C_6$-alkyl group.

It is always of high-interest in the field of agrochemicals to use pesticidal compounds more active than the compounds already known by the man ordinary skilled in the art whereby reduced amounts of compound can be used whilst retaining equivalent efficacy.

Furthermore, the provision of new pesticidal compounds with a higher efficacy strongly reduces the risk of appearance of resistant strains in the fungi to be treated.

We have now found a new family of compounds which show enhanced fungicidal activity over the general known family of such compounds.

Accordingly, the present invention provides a N-[(trisubstitutedsilyl)methyl]carboxamide or its thiocarboxamide derivative of formula (I)

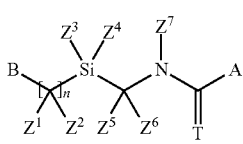

wherein
  A represents a phenyl group that can be substituted by up to five groups R or a carbo-linked, unsaturated or partially saturated, 6-membered heterocyclyl group that can be substituted by up to four groups R;
  T represents O or S;
  n represents 0 or 1;
  B represents a phenyl ring that can be substituted by up to 5 groups X which can be the same or different; a naphthyl ring that can be substituted by up to 7 groups X which can be the same or different; a thienyl ring that can be substituted by up to 3 groups X which can be the same or different; or a benzothiophenyl ring that can be substituted by up to 5 groups X which can be the same or different;
  X represents a halogen atom; nitro; cyano; isonitrile; hydroxy; amino; sulfanyl; pentafluoro-$\lambda^6$-sulfanyl; formyl; formyloxy; formylamino; substituted or non-substituted (hydroxyimino)-$C_1$-$C_8$-alkyl; substituted or non-substituted ($C_1$-$C_8$-alkoxyimino)-$C_1$-$C_8$-alkyl; substituted or non-substituted ($C_2$-$C_8$-alkenyloxyimino)-$C_1$-$C_8$-alkyl; substituted or non-substituted ($C_2$-$C_8$-alkynyloxyimino)-$C_1$-$C_8$-alkyl; substituted or non-substituted (benzyloxyimino)-$C_1$-$C_8$-alkyl; carboxy; carbamoyl; N-hydroxycarbamoyl; carbamate; substituted or non-substituted $C_1$-$C_8$-alkyl; $C_1$-$C_8$-halogenoalkyl having 1 to 5 halogen atoms; substituted or non-substituted $C_2$-$C_8$-alkenyl; $C_2$-$C_8$-halogenoalkenyl having 1 to 5 halogen atoms; substituted or non-substituted $C_2$-$C_8$-alkynyl; $C_2$-$C_8$-halogenoalkynyl having 1 to 5 halogen atoms; substituted or non-substituted $C_1$-$C_8$-alkoxy; $C_1$-$C_8$-halogenoalkoxy having 1 to 5 halogen atoms; substituted or non-substituted $C_1$-$C_8$-alkylsulfanyl; $C_1$-$C_8$-halogenoalkylsulfanyl having 1 to 5 halogen atoms; substituted or non-substituted $C_1$-$C_8$-alkylsulfinyl; $C_1$-$C_8$-halogenoalkylsulfinyl having 1 to 5 halogen atoms; substituted or non-substituted $C_1$-$C_8$-alkylsulfonyl; $C_1$-$C_8$-halogenoalkylsulfonyl having 1 to 5 halogen atoms; substituted or non-substituted $C_1$-$C_8$-alkylamino; substituted or non-substituted di-$C_1$-$C_8$-alkylamino; substituted or non-substituted $C_2$-$C_8$-alkenyloxy; $C_2$-$C_8$-halogenoalkenyloxy having 1 to 5 halogen atoms; substituted or non-substituted $C_3$-$C_8$-alkynyloxy; $C_3$-$C_7$-halogenoalkynyloxy having 1 to 5 halogen atoms; substituted or non-substituted $C_3$-$C_7$-cycloalkyl; $C_3$-$C_7$-halogenocycloalkyl having 1 to 5 halogen atoms; substituted or non-substituted ($C_3$-$C_7$-cycloalkyl)-$C_1$-$C_8$-alkyl; substituted or non-substituted ($C_3$-$C_7$-cycloalkyl)-$C_2$-$C_8$-alkenyl; substituted or non-substituted ($C_3$-$C_7$-cycloalkyl)-$C_2$-$C_8$-alkynyl; substituted or non-substituted tri($C_1$-$C_8$-alkyl)silyl; substituted or non-substituted tri($C_1$-$C_8$-alkyl)silyl-$C_1$-$C_8$-alkyl; substituted or non-substituted $C_1$-$C_8$-alkylcarbonyl; $C_1$-$C_8$-halogenoalkylcarbonyl having 1 to 5 halogen atoms; substituted or non-substituted $C_1$-$C_8$-alkylcarbonyloxy; $C_1$-$C_8$-halogenoalkylcarbonyloxy having 1 to 5 halogen atoms; substituted or non-substituted $C_1$-$C_8$-alkylcarbonylamino; $C_1$-$C_8$-halogenoalkyl-carbonylamino having 1 to 5 halogen atoms; substituted or non-substituted $C_1$-$C_8$-alkoxycarbonyl; $C_1$-$C_8$-halogenoalkoxycarbonyl having 1 to 5 halogen atoms; substituted or non-substituted $C_1$-$C_8$-alkyloxycarbonyloxy; $C_1$-$C_8$-halogenoalkoxycarbonyloxy having 1 to 5 halogen atoms; substituted or non-substituted $C_1$-$C_8$-alkylcarbamoyl; substituted or non-substituted di-$C_1$-$C_8$-alkylcarbamoyl; substituted or non-substituted $C_1$-$C_8$-alkylaminocarbonyloxy; substituted or non-substituted di-$C_1$-$C_8$-alkylaminocarbonyloxy; substituted or non-substituted N—($C_1$-$C_8$-alkyl)hydroxy carbamoyl; substituted or non-substituted $C_1$-$C_8$-alkoxycarbamoyl; substituted or non-substituted N—($C_1$-$C_8$-alkyl)-$C_1$-$C_8$-alkoxycarbamoyl; aryl that can be substituted by up to 6 groups Q which can be the same or different; $C_1$-$C_8$-arylalkyl that can be substituted by up to 6 groups Q which can be the same or different; $C_2$-$C_8$-arylalkenyl that can be substituted by up to 6 groups Q which can be the same or different; $C_2$-$C_8$-arylalkynyl that can be substituted by up to 6 groups Q which can be the same or different; aryloxy that can be substituted by up to 6 groups Q which can be the same or different; arylsulfanyl that can be substituted by up to 6 groups Q which can be the same or different; arylamino that can be substituted by up to 6 groups Q which can be the same or different; $C_1$-$C_8$-arylalkyloxy that can be substituted by up to 6 groups Q which can be the same or different; $C_1$-$C_8$-arylalkylsulfanyl that can be substituted by up to 6 groups Q which can be the same or different; or $C_1$-$C_8$-arylalkylamino that can be substituted by up to 6 groups Q which can be the same or different; or two substituent X together with the consecutive carbon atoms to which they are linked can form a 5- or 6-membered, saturated carbocycle or saturated heterocycle, which can be substituted by up to four groups Q which can be the same or different;

$Z^1$ and $Z^2$ independently represent a hydrogen atom; a halogen atom; cyano; substituted or non-substituted $C_1$-$C_8$-alkyl; $C_1$-$C_8$-halogenoalkyl having 1 to 5 halogen atoms; substituted or non-substituted $C_1$-$C_8$-alkoxy; substituted or non-substituted $C_1$-$C_8$-alkylsulfanyl; or substituted or non-substituted $C_1$-$C_8$-alkoxycarbonyl; or $Z^1$ and $Z^2$ are a $C_2$-$C_5$-alkylene group that can be substituted by up to four $C_1$-$C_8$-alkyl groups;

$Z^3$ and $Z^4$ independently represent a substituted or non-substituted $C_1$-$C_8$-alkyl;

$Z^5$ and $Z^6$ independently represent a hydrogen atom; a halogen atom; cyano; substituted or non-substituted $C_1$-$C_8$-alkyl; $C_1$-$C_8$-halogenoalkyl having 1 to 5 halogen atoms; substituted or non-substituted $C_1$-$C_8$-alkoxy; substituted or non-substituted $C_1$-$C_8$-alkylsulfanyl; or substituted or non-substituted $C_1$-$C_8$-alkoxycarbonyl; or $Z^5$ and $Z^6$ are a $C_2$-$C_5$-alkylene group that can be substituted by up to four $C_1$-$C_8$-alkyl groups;

$Z^7$ represents a hydrogen atom; a formyl group; a substituted or non-substituted $C_1$-$C_8$-alkyl; a substituted or non substituted $C_1$-$C_8$-alkoxy; a non-substituted $C_3$-$C_7$-cycloalkyl or a $C_3$-$C_7$-cycloalkyl substituted by up to 10 atoms or groups that can be the same or different and that can be selected in the list consisting of halogen atoms, cyano, $C_1$-$C_8$-alkyl, $C_1$-$C_8$-halogenoalkyl comprising up to 9 halogen atoms that can be the same or different, $C_1$-$C_8$-alkoxy, $C_1$-$C_8$-halogenoalkoxy comprising up to 9 halogen atoms that can be the same or different, $C_1$-$C_8$-alkoxycarbonyl, $C_1$-$C_8$-halogenoalkoxycarbonyl comprising up to 9 halogen atoms that can be the same or different, $C_1$-$C_8$-alkylaminocarbonyl and di-$C_1$-$C_8$-alkylaminocarbonyl;

Q independently represents a halogen atom; cyano; nitro; substituted or non-substituted $C_1$-$C_8$-alkyl; $C_1$-$C_8$-halogenoalkyl having 1 to 9 halogen atoms that can be the same or different; substituted or non-substituted $C_1$-$C_8$-alkoxy; $C_1$-$C_8$-halogenoalkoxy having 1 to 9 halogen atoms that can be the same or different; substituted or non-substituted $C_1$-$C_8$-alkylsulfanyl; $C_1$-$C_8$-halogenoalkylsulfanyl having 1 to 9 halogen atoms that can be the same or different; substituted or non-substituted tri($C_1$-$C_8$-alkyl)silyl; substituted or non-substituted tri($C_1$-$C_8$-alkyl)silyl-$C_1$-$C_8$-alkyl; substituted or non-substituted ($C_1$-$C_8$-alkoxyimino)-$C_1$-$C_8$-alkyl; substituted or non-substituted (benzyloxyimino)-$C_1$-$C_8$-alkyl;

R independently represents hydrogen atom; halogen atom; nitro; cyano; hydroxy; amino; sulfanyl; pentafluoro-$\lambda^6$-sulfanyl; substituted or non-substituted ($C_1$-$C_8$-alkoxyimino)-$C_1$-$C_8$-alkyl; substituted or non-substituted (benzyloxyimino)-$C_1$-$C_8$-alkyl; substituted or non-substituted $C_1$-$C_8$-alkyl; $C_1$-$C_8$-halogenoalkyl having 1 to 5 halogen atoms; substituted or non-substituted $C_2$-$C_8$-alkenyl; $C_2$-$C_8$-halogenoalkenyl having 1 to 5 halogen atoms; substituted or non-substituted $C_2$-$C_8$-alkynyl; $C_2$-$C_8$-halogenoalkynyl having 1 to 5 halogen atoms; substituted or non-substituted $C_1$-$C_8$-alkoxy; $C_1$-$C_8$-halogenoalkoxy having 1 to 5 halogen atoms; substituted or non-substituted $C_1$-$C_8$-alkylsulfanyl; $C_1$-$C_8$-halogenoalkylsulfanyl having 1 to 5 halogen atoms; substituted or non-substituted $C_1$-$C_8$-alkylsulfinyl; $C_1$-$C_8$-halogenoalkylsulfinyl having 1 to 5 halogen atoms; substituted or non-substituted $C_1$-$C_8$-alkylsulfonyl; $C_1$-$C_8$-halogenoalkylsulfonyl having 1 to 5 halogen atoms; substituted or non-substituted $C_1$-$C_8$-alkylamino; substituted or non-substituted di-$C_1$-$C_8$-alkylamino; substituted or non-substituted $C_2$-$C_8$-alkenyloxy; substituted or non-substituted $C_3$-$C_8$-alkynyloxy; substituted or non-substituted $C_3$-$C_7$-cycloalkyl; $C_3$-$C_7$-halogenocycloalkyl having 1 to 5 halogen atoms; substituted or non-substituted tri(($C_1$-$C_8$-alkyl)silyl; substituted or non-substituted $C_1$-$C_8$-alkylcarbonyl; $C_1$-$C_8$-halogenoalkylcarbonyl having 1 to 5 halogen atoms; substituted or non-substituted $C_1$-$C_8$-alkoxycarbonyl; $C_1$-$C_8$-halogenoalkoxycarbonyl having 1 to 5 halogen atoms; substituted or non-substituted $C_1$-$C_8$-alkylcarbamoyl; substituted or non-substituted di-$C_1$-$C_8$-alkylcarbamoyl; phenoxy; phenylsulfanyl; phenylamino; benzyloxy; benzylsulfanyl; or benzylamino;

as well as its salts, N-oxides, metal complexes, metallic complexes and optically active isomers.

For the compounds according to the invention, the following generic terms are generally used with the following meanings:

halogen means fluorine, bromine, chlorine or iodine.
carboxy means —C(=O)OH;
carbonyl means —C(=O)—;
carbamoyl means —C(=O)NH$_2$;
N-hydroxycarbamoyl means —C(=O)NHOH;
SO represents a sulfoxyde group;
SO$_2$ represents a sulfone group;

an alkyl group, an alkenyl group and an alkynyl group as well as moieties containing these terms, can be linear or branched;

the aryl moiety contained in an aryl group, an arylalkyl group, an arylalkenyl group and an arylalkynyl group as well as moieties containing these terms, can be a phenyl group that can be substituted by up to 5 groups Q which can be the same or different, a naphthyl group that can be substituted by up to 7 groups Q which can be the same or different or a pyridyl group that can be substituted by up to 4 groups Q which can be the same or different;

and, heteroatom means sulfur, nitrogen or oxygen.

in the case of an amino group or the amino moiety of any other amino-comprising group, substituted by two substituent that can be the same or different, the two substituent together with the nitrogen atom to which they are linked can form a heterocyclyl group, preferably a 5- to 7-membered heterocyclyl group, that can be substituted or that can include other hetero atoms, for example a morpholino group or piperidinyl group.

unless indicated otherwise, a group or a substituent that is substituted according to the invention can be substituted by one or more of the following groups or atoms: a halogen atom, a nitro group, a hydroxy group, a cyano group, an amino group, a sulfanyl group, a pentafluoro-$\lambda^6$-sulfanyl group, a formyl group, a formyloxy group, a formylamino group, a carbamoyl group, a N-hydroxycarbamoyl group, a (hydroxyimino)-$C_1$-$C_6$-alkyl group, a $C_1$-$C_8$-alkyl, a tri($C_1$-$C_8$-alkyl)silyl-$C_1$-$C_8$-alkyl, $C_1$-$C_8$-cycloalkyl, tri($C_1$-$C_8$-alkyl)silyl-$C_1$-$C_8$-cycloalkyl, a $C_1$-$C_8$-halogenoalkyl having 1 to 5 halogen atoms, a $C_1$-$C_8$-halogenocycloalkyl having 1 to 5 halogen atoms, a $C_2$-$C_8$-alkenyl, a $C_2$-$C_8$-alkynyl, a C$_2$-C$_8$-alkenyloxy, a C$_2$-C$_8$-alkynyloxy, a C$_1$-C$_8$-alkylamino, a di-C$_1$-C$_8$-alkylamino, a C$_1$-C$_8$-alkoxy, a C$_1$-C$_8$-halogenoalkoxy having 1 to 5 halogen atoms, a C$_1$-C$_8$-alkylsulfanyl, a C$_1$-C$_8$-halogenoalkylsulfanyl having 1 to 5 halogen atoms, a C$_2$-C$_8$-alkenyloxy, a C$_2$-C$_8$-halogenoalkenyloxy having 1 to 5 halogen atoms, a C$_3$-C$_8$-alkynyloxy, a C$_3$-C$_8$-halogenoalkynyloxy having 1 to 5 halogen atoms, a C$_1$-C$_8$-alkylcarbonyl, a C$_1$-C$_8$-halogenoalkylcarbonyl having 1 to 5 halogen atoms, a C$_1$-C$_8$-alkylcarbamoyl, a di-C$_1$-C$_8$-alkylcarbamoyl, a N-C$_1$-C$_8$-alkyloxycarbamoyl, a C$_1$-C$_8$-alkoxycarbamoyl, a N-C$_1$-C$_8$-alkyl-C$_1$-C$_8$-alkoxycarbamoyl, a C$_1$-C$_8$-alkoxycarbonyl, a C$_1$-C$_8$-halogenoalkoxycarbonyl having 1 to 5 halogen atoms, a C-C$_8$-alkylcarbonyloxy, a C$_1$-C$_8$-halogenoalkylcarbonyloxy having 1 to 5 halogen atoms, a C$_1$-C$_8$-alkylcarbonylamino, a C$_1$-C$_8$-halogenoalkylcarbonylamino having 1 to 5 halogen atoms, a C$_1$-C$_8$-alkylaminocarbonyloxy, a di-C$_1$-C$_8$-alkylaminocarbonyloxy, a C$_1$-C$_8$-alkyloxycarbonyloxy, a C$_1$-C$_8$-alkylsulfinyl, a C$_1$-C$_8$-halogenoalkylsulfinyl having 1 to 5 halogen atoms, a C$_1$-C$_8$-alkylsulfonyl, a C$_1$-C$_8$-halogenoalkylsulfonyl having 1 to 5 halogen atoms, a C$_1$-C$_8$-alkylaminosulfamoyl, a di-C$_1$-C$_8$-alkylaminosulfamoyl, a (C$_i$-C$_6$-alkoxyimino)-C$_1$-C$_6$-alkyl, a (C$_1$-C$_6$-alkenyloxyimino)-C$_1$-C$_6$-alkyl, a (C$_1$-C$_6$-alkynyloxyimino)-C$_1$-C$_6$-alkyl, a 2-oxopyrrolidin-1-yl, (benzyloxyimino)-C$_1$-C$_6$-alkyl, C$_1$-C$_8$-alkoxyalkyl, C$_1$-C$_8$-halogenoalkoxyalkyl having 1 to 5 halogen atoms, benzyloxy, benzylsulfanyl, benzylamino, phenoxy, phenylsulfanyl, or phenylamino.

Any of the compounds of the present invention can exist in one or more optical or chiral isomer forms depending on the number of asymmetric centres in the compound. The invention thus relates equally to all the optical isomers and to their racemic or scalemic mixtures (the term "scalemic" denotes a mixture of enantiomers in different proportions) and to the mixtures of all the possible stereoisomers, in all proportions. The diastereoisomers and/or the optical isomers can be separated according to the methods which are known per se by the man ordinary skilled in the art.

Any of the compounds of the present invention can also exist in one or more geometric isomer forms depending on the number of double bonds in the compound. The invention thus relates equally to all geometric isomers and to all possible mixtures, in all proportions. The geometric isomers can be separated according to general methods, which are known per se by the man ordinary skilled in the art.

Any of the compounds of the present invention can also exist in one or more geometric isomer forms depending on the relative position (syn/anti or cis/trans) of the substituents of ring B. The invention thus relates equally to all syn/anti (or cis/trans) isomers and to all possible syn/anti (or cis/trans) mixtures, in all proportions. The syn/anti (or cis/trans) isomers can be separated according to general methods, which are known per se by the man ordinary skilled in the art.

Any of the compounds of formula (I) wherein X represents a hydroxy, a sulfanyl group or an amino group may be found in its tautomeric form resulting from the shift of the proton of said hydroxy, sulfanyl or amino group. Such tautomeric forms of such compounds are also part of the present invention. More generally speaking, all tautomeric forms of compounds of formula (I) wherein X represents a hydroxy, a sulfanyl group or an amino group, as well as the tautomeric forms of the compounds which can optionally be used as intermediates in the preparation processes and which will be defined in the description of these processes, are also part of the present invention.

Preferred compounds according to the invention are compounds of formula (I) wherein A is selected in the list consisting of:

a carbocycle of formula (A$^1$)

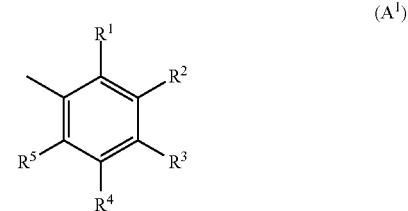

(A$^1$)

wherein:

R$^1$ represents a halogen atom; a hydroxy group; an amino group; a cyano group; substituted or non-substituted C$_1$-C$_5$-alkyl; C$_1$-C$_5$-halogenoalkyl comprising up to 5 halogen atoms that can be the same or different; substituted or non-substituted C$_1$-C$_5$-alkoxy; C$_1$-C$_5$-halogenoalkoxy comprising up to 5 halogen atoms that can be the same or different; substituted or non-substituted C$_1$-C$_5$-alkylsulfanyl or C$_1$-C$_5$-halogenoalkylsulfanyl comprising up to 5 halogen atoms that can be the same or different;

R$^2$ to R$^5$ that can be the same or different represent a hydrogen atom; a halogen atom; a hydroxy group; an amino group; a cyano group; substituted or non-substituted C$_1$-C$_5$-alkyl; C$_1$-C$_5$-halogenoalkyl comprising up to 5 halogen atoms that can be the same or different; substituted or non-substituted C$_1$-C$_5$-alkoxy; C$_1$-C$_5$-halogenoalkoxy comprising up to 5 halogen atoms that can be the same or different; substituted or non-substituted C$_1$-C$_5$-alkylsulfanyl or C$_1$-C$_5$-halogenoalkylsulfanyl comprising up to 5 halogen atoms that can be the same or different;

a heterocycle of formula (A$^2$)

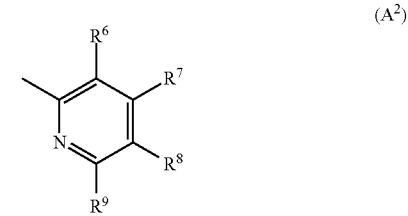

(A$^2$)

wherein:

R$^6$ represents a halogen atom; a cyano group; substituted or non-substituted C$_1$-C$_5$-alkyl; C$_1$-C$_5$-halogenoalkyl comprising up to 5 halogen atoms that can be the same or different; substituted or non-substituted C$_1$-C$_5$-alkoxy; C$_1$-C$_5$-halogenoalkoxy comprising up to 5 halogen atoms that can be the same or different; substituted or non-substituted C$_1$-C$_5$-alkylsulfanyl or C$_1$-C$_5$-halogenoalkylsulfanyl comprising up to 5 halogen atoms that can be the same or different;

R$^7$ to R$^9$ that can be the same or different represent a hydrogen atom; a halogen atom; a hydroxy group; an amino group; a cyano group; substituted or non-substituted C$_1$-C$_5$-alkyl; C$_1$-C$_5$-halogenoalkyl comprising up to 5 halogen atoms that can be the same or different; substituted or non-substituted $C_1$-$C_5$-alkoxy; $C_1$-$C_5$-halogenoalkoxy comprising up to 5 halogen atoms that can be the same or different; substituted or non-substituted $C_1$-$C_5$-alkylsulfanyl or $C_1$-$C_5$-halogenoalkylsulfanyl comprising up to 5 halogen atoms that can be the same or different;

a heterocycle of formula ($A^3$)

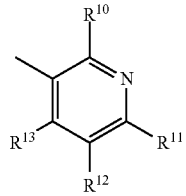

wherein:

$R^{10}$ represents a halogen atom; a hydroxy group; an amino group, a cyano group; substituted or non-substituted $C_1$-$C_5$-alkyl; $C_1$-$C_5$-halogenoalkyl comprising up to 5 halogen atoms that can be the same or different; substituted or non-substituted $C_1$-$C_5$-alkoxy; $C_1$-$C_5$-halogenoalkoxy comprising up to 5 halogen atoms that can be the same or different; substituted or non-substituted $C_1$-$C_5$-alkylsulfanyl or $C_1$-$C_5$-halogenoalkylsulfanyl comprising up to 5 halogen atoms that can be the same or different;

$R^{11}$ to $R^{13}$ that can be the same or different represent a hydrogen atom; a halogen atom; a hydroxy group; an amino group; a cyano group; substituted or non-substituted $C_1$-$C_5$-alkyl; $C_1$-$C_5$-halogenoalkyl comprising up to 5 halogen atoms that can be the same or different; substituted or non-substituted $C_1$-$C_5$-alkoxy; $C_1$-$C_5$-halogenoalkoxy comprising up to 5 halogen atoms that can be the same or different; substituted or non-substituted $C_1$-$C_5$-alkylsulfanyl or $C_1$-$C_5$-halogenoalkylsulfanyl comprising up to 5 halogen atoms that can be the same or different;

a heterocycle of formula ($A^4$)

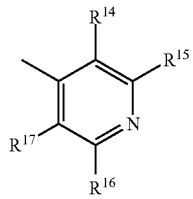

wherein:

$R^{14}$ represents a halogen atom; a cyano group; substituted or non-substituted $C_1$-$C_5$-alkyl; $C_1$-$C_5$-halogenoalkyl comprising up to 5 halogen atoms that can be the same or different; substituted or non-substituted $C_1$-$C_5$-alkoxy; $C_1$-$C_5$-halogenoalkoxy comprising up to 5 halogen atoms that can be the same or different; substituted or non-substituted $C_1$-$C_5$-alkylsulfanyl or $C_1$-$C_5$-halogenoalkylsulfanyl comprising up to 5 halogen atoms that can be the same or different;

$R^{15}$ to $R^{17}$ that can be the same or different represent a hydrogen atom; a halogen atom; a hydroxy group; an amino group; a cyano group; substituted or non-substituted $C_1$-$C_5$-alkyl; $C_1$-$C_5$-halogenoalkyl comprising up to 5 halogen atoms that can be the same or different; substituted or non-substituted $C_1$-$C_5$-alkoxy; $C_1$-$C_5$-halogenoalkoxy comprising up to 5 halogen atoms that can be the same or different; substituted or non-substituted $C_1$-$C_5$-alkylsulfanyl or $C_1$-$C_5$-halogenoalkylsulfanyl comprising up to 5 halogen atoms that can be the same or different;

a heterocycle of formula ($A^5$)

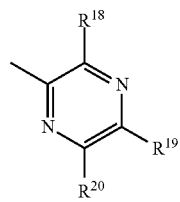

wherein:

$R^{18}$ represents a halogen atom; a cyano group; substituted or non-substituted $C_1$-$C_5$-alkyl; $C_1$-$C_5$-halogenoalkyl comprising up to 5 halogen atoms that can be the same or different; substituted or non-substituted $C_1$-$C_5$-alkoxy; $C_1$-$C_5$-halogenoalkoxy comprising up to 5 halogen atoms that can be the same or different; substituted or non-substituted $C_1$-$C_5$-alkylsulfanyl or $C_1$-$C_5$-halogenoalkylsulfanyl comprising up to 5 halogen atoms that can be the same or different;

$R^{19}$ and $R^{20}$ that can be the same or different represent a hydrogen atom; a halogen atom; substituted or non-substituted $C_1$-$C_5$-alkyl or $C_1$-$C_5$-halogenoalkyl comprising up to 5 halogen atoms that can be the same or different;

a heterocycle of formula ($A^6$)

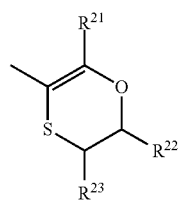

wherein:

$R^{21}$ represents a halogen atom; a cyano group; substituted or non-substituted $C_1$-$C_5$-alkyl; $C_1$-$C_5$-halogenoalkyl comprising up to 5 halogen atoms that can be the same or different; substituted or non-substituted $C_1$-$C_5$-alkoxy; $C_1$-$C_5$-halogenoalkoxy comprising up to 5 halogen atoms that can be the same or different; substituted or non-substituted $C_1$-$C_5$-alkylsulfanyl or $C_1$-$C_5$-halogenoalkylsulfanyl comprising up to 5 halogen atoms that can be the same or different;

$R^{22}$ and $R^{23}$ that can be the same or different represent a hydrogen atom; substituted or non-substituted $C_1$-$C_5$-alkyl or $C_1$-$C_5$-halogenoalkyl comprising up to 5 halogen atoms that can be the same or different;

a heterocycle of formula ($A^7$)

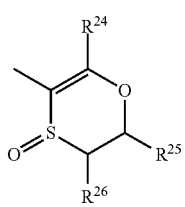

wherein:

R²⁴ represents a halogen atom; a cyano group; substituted or non-substituted $C_1$-$C_5$-alkyl; $C_1$-$C_5$-halogenoalkyl comprising up to 5 halogen atoms that can be the same or different; substituted or non-substituted $C_1$-$C_5$-alkoxy; $C_1$-$C_5$-halogenoalkoxy comprising up to 5 halogen atoms that can be the same or different; substituted or non-substituted $C_1$-$C_5$-alkylsulfanyl or $C_1$-$C_5$-halogenoalkylsulfanyl comprising up to 5 halogen atoms that can be the same or different;

R²⁵ and R²⁶ that can be the same or different represent a hydrogen atom; substituted or non-substituted $C_1$-$C_5$-alkyl or $C_1$-$C_5$-halogenoalkyl comprising up to 5 halogen atoms that can be the same or different;

a heterocycle of formula (A⁶)

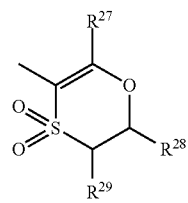

(A⁸)

wherein:

R²⁷ represents a halogen atom; a cyano group; substituted or non-substituted $C_1$-$C_5$-alkyl; $C_1$-$C_5$-halogenoalkyl comprising up to 5 halogen atoms that can be the same or different; substituted or non-substituted $C_1$-$C_5$-alkoxy; $C_1$-$C_5$-halogenoalkoxy comprising up to 5 halogen atoms that can be the same or different; substituted or non-substituted $C_1$-$C_5$-alkylsulfanyl or $C_1$-$C_5$-halogenoalkylsulfanyl comprising up to 5 halogen atoms that can be the same or different;

R²⁸ and R²⁹ that can be the same or different represent a hydrogen atom; substituted or non-substituted $C_1$-$C_5$-alkyl or $C_1$-$C_5$-halogenoalkyl comprising up to 5 halogen atoms that can be the same or different;

a heterocycle of formula (A⁹)

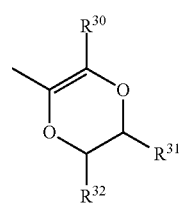

(A⁹)

wherein:

R³⁰ represents a halogen atom; a cyano group; substituted or non-substituted $C_1$-$C_5$-alkyl; $C_1$-$C_5$-halogenoalkyl comprising up to 5 halogen atoms that can be the same or different; substituted or non-substituted $C_1$-$C_5$-alkoxy; $C_1$-$C_5$-halogenoalkoxy comprising up to 5 halogen atoms that can be the same or different; substituted or non-substituted $C_1$-$C_5$-alkylsulfanyl or $C_1$-$C_5$-halogenoalkylsulfanyl comprising up to 5 halogen atoms that can be the same or different;

R³¹ and R³² that can be the same or different represent a hydrogen atom; substituted or non-substituted $C_1$-$C_5$-alkyl or $C_1$-$C_5$-halogenoalkyl comprising up to 5 halogen atoms that can be the same or different;

a heterocycle of formula (A¹⁰)

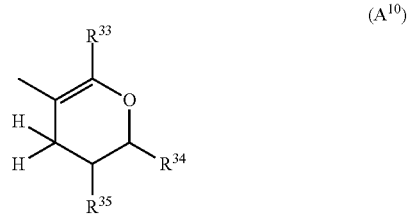

(A¹⁰)

wherein:

R³³ represents a halogen atom; a cyano group; substituted or non-substituted $C_1$-$C_5$-alkyl; $C_1$-$C_5$-halogenoalkyl comprising up to 5 halogen atoms that can be the same or different; substituted or non-substituted $C_1$-$C_5$-alkoxy; $C_1$-$C_5$-halogenoalkoxy comprising up to 5 halogen atoms that can be the same or different; substituted or non-substituted $C_1$-$C_5$-alkylsulfanyl or $C_1$-$C_5$-halogenoalkylsulfanyl comprising up to 5 halogen atoms that can be the same or different;

R³⁴ and R³⁵ that can be the same or different represent a hydrogen atom; substituted or non-substituted $C_1$-$C_5$-alkyl or $C_1$-$C_5$-halogenoalkyl comprising up to 5 halogen atoms that can be the same or different;

More preferred compounds according to the invention are compounds of formula (I) wherein A is selected in the list consisting of A¹; A³; A⁵ and A⁶ as herein-defined.

Even more preferred compounds according to the invention are compounds of formula (I) wherein A represents A¹ wherein R¹ represents a halogen atom, substituted or non-substituted $C_1$-$C_5$-alkyl, $C_1$-$C_5$-halogenoalkyl comprising up to 5 halogen atoms that can be the same or different and R² to R⁵ represent a hydrogen atom.

Other even more preferred compounds according to the invention are compounds of formula (I) wherein A represents A³ wherein R¹⁰ represents a halogen atom or $C_1$-$C_5$-halogenoalkyl comprising up to 5 halogen atoms that can be the same or different and R¹¹ to R¹³ represent a hydrogen atom.

Other even more preferred compounds according to the invention are compounds of formula (I) wherein A represents A⁵ wherein R¹⁸ represents a halogen atom or $C_1$-$C_5$-halogenoalkyl comprising up to 5 halogen atoms that can be the same or different and R¹⁹ and R²⁰ represent a hydrogen atom.

Other even more preferred compounds according to the invention are compounds of formula (I) wherein A represents A⁶ wherein R²¹ represents a non-substituted $C_1$-$C_5$-alkyl or $C_1$-$C_5$-halogenoalkyl comprising up to 5 halogen atoms that can be the same or different and R²² and R²³ represent a hydrogen atom.

Other preferred compounds according to the invention are compounds of formula (I) wherein T represents O.

Other preferred compounds according to the invention are compounds of formula (I) wherein B represents a substituted or non-substituted phenyl ring or a substituted or non-substituted naphthyl ring. Even more preferably, B represents a substituted or non-substituted phenyl ring.

Other preferred compounds according to the invention are compounds of formula (I) wherein X independently represents a halogen atom; substituted or non-substituted $C_1$-$C_8$-alkyl; $C_1$-$C_8$-halogenoalkyl comprising up to 9 halogen atoms that can be the same or different; substituted or non-substituted tri($C_1$-$C_8$-alkyl)silyl; substituted or non-substituted $C_1$-$C_8$-alkoxy or $C_1$-$C_8$-halogenoalkoxy comprising up to 9 halogen atoms that can be the same or different; or wherein two consecutive substituents X together with the phenyl ring form a substituted or non substituted 1,3-benzodioxolyl; 1,2,3,4-tetrahydro-quinoxalinyl; 3,4-dihydro-2H-1,4-benzoxazinyl; 1,4-benzodioxanyl; indanyl; 2,3-dihydrobenzofuranyl; or indolinyl.

Other preferred compounds according to the invention are compounds of formula (I) wherein $Z^1$, $Z^2$, $Z^5$ and $Z^6$ independently represent a hydrogen atom, a substituted or non-substituted $C_1$-$C_8$-alkyl or a substituted or non-substituted $C_1$-$C_8$-alkoxy.

Other preferred compounds according to the invention are compounds of formula (I) wherein $Z^3$ and $Z^4$ independently represent a non-substituted $C_1$-$C_8$-alkyl. More preferably, $Z^3$ and $Z^4$ independently represent a non-substituted $C_1$-$C_3$-alkyl. Even more preferably, $Z^3$ and $Z^4$ represent methyl.

Other preferred compounds according to the invention are compounds of formula (I) wherein $Z^7$ represents a hydrogen atom, a non-substituted $C_3$-$C_7$ cycloalkyl or a $C_3$-$C_7$ cycloalkyl substituted by up to 10 groups or atoms that can be the same or different and that can be selected in the list consisting of halogen atoms, $C_1$-$C_8$-alkyl, $C_1$-$C_8$-halogenoalkyl comprising up to 9 halogen atoms that can be the same or different, $C_1$-$C_8$-alkoxy or $C_1$-$C_8$-halogenoalkoxy comprising up to 9 halogen atoms that can be the same or different. More preferably $Z^7$ represents a non-substituted $C_3$-$C_7$-cycloalkyl; even more preferably $Z^7$ represents cyclopropyl.

Other preferred compounds according to the invention are compounds of formula (I) wherein R independently represents a hydrogen atom; halogen atom; cyano; substituted or non-substituted $C_1$-$C_8$-alkylamino; substituted or non-substituted di-$C_1$-$C_8$-alkylamino; substituted or non-substituted tri($C_1$-$C_8$-alkyl)silyl; substituted or non-substituted $C_1$-$C_8$-alkyl; $C_1$-$C_8$-halogenoalkyl comprising up to 5 halogen atoms that can be the same or different; substituted or non-substituted $C_1$-$C_8$-alkoxy; $C_1$-$C_8$-halogenoalkoxy comprising up to 5 halogen atoms that can be the same or different; substituted or non-substituted $C_1$-$C_8$-alkylsulfanyl; amino; hydroxyl; nitro; substituted or non-substituted $C_1$-$C_8$-alkoxycarbonyl; substituted or non-substituted $C_2$-$C_8$-alkynyloxy.

The above mentioned preferences with regard to the substituents of the compounds according to the invention can be combined in various manners. These combinations of preferred features thus provide sub-classes of compounds according to the invention. Examples of such sub-classes of preferred compounds according to the invention can be combined:

preferred features of A with preferred features of B, $Z^1$, $Z^2$, $Z^3$, $Z^4$, $Z^5$, $Z^6$, $Z^7$, X, T and R;
preferred features of B with preferred features of A, $Z^1$, $Z^2$, $Z^3$, $Z^4$, $Z^5$, $Z^6$, $Z^7$, X, T and R;
preferred features of $Z^1$ with preferred features of A, B, $Z^2$, $Z^3$, $Z^4$, $Z^5$, $Z^6$, $Z^7$, X, T and R;
preferred features of $Z^2$ with preferred features of A, B, $Z^1$, $Z^3$, $Z^4$, $Z^5$, $Z^6$, $Z^7$, X, T and R;
preferred features of $Z^3$ with preferred features of A, B, $Z^1$, $Z^2$, $Z^4$, $Z^5$, $Z^6$, $Z^7$, X, T and R;
preferred features of $Z^4$ with preferred features of A, B, $Z^1$, $Z^2$, $Z^3$, $Z^5$, $Z^6$, $Z^7$, X, T and R;
preferred features of $Z^5$ with preferred features of A, B, $Z^1$, $Z^2$, $Z^3$, $Z^4$, $Z^6$, $Z^7$, X, T and R;
preferred features of $Z^6$ with preferred features of A, B, $Z^1$, $Z^2$, $Z^3$, $Z^4$, $Z^5$, $Z^7$, X, T and R;
preferred features of $Z^7$ with preferred features of A, B, $Z^1$, $Z^2$, $Z^3$, $Z^4$, $Z^5$, $Z^6$, X, T and R;
preferred features of X with preferred features of A, B, $Z^1$, $Z^2$, $Z^3$, $Z^4$, $Z^5$, $Z^6$, $Z^7$, T and R;
preferred features of T with preferred features of A, B, $Z^1$, $Z^2$, $Z^3$, $Z^4$, $Z^5$, $Z^6$, $Z^7$, X and R;
preferred features of R with preferred features of A, B, $Z^1$, $Z^2$, $Z^3$, $Z^4$, $Z^5$, $Z^6$, $Z^7$, T and X;

In these combinations of preferred features of the substituents of the compounds according to the invention, the said preferred features can also be selected among the more preferred features of each of A, B, $Z^1$, $Z^2$, $Z^3$, $Z^4$, $Z^5$, $Z^6$, $Z^7$, T, X and R, so as to form most preferred subclasses of compounds according to the invention.

The present invention also relates to a process for the preparation of the compound of formula (I).

Thus, according to a further aspect of the present invention there is provided a process P1 for the preparation of a compound of formula (I) as herein-defined and wherein T represents O and that comprises reacting a N-[(trisubstitutedsilyl)methyl]amine derivative of formula (II) or one of its salts:

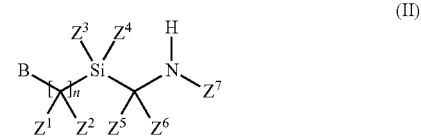

wherein B, n, $Z^1$, $Z^2$, $Z^3$, $Z^4$, $Z^5$, $Z^6$ and $Z^7$ are as herein-defined; with a carboxylic acid derivative of formula (III):

wherein A is as herein-defined and $L^1$ represents a leaving group selected in the list consisting of a halogen atom, a hydroxyl group, —$OR^a$, —OC(=O)$R^a$, $R^a$ being a substituted or non-substituted $C_1$-$C_6$-alkyl, a substituted or non-substituted $C_1$-$C_6$-haloalkyl, a benzyl, 4-methoxybenzyl or pentafluorophenyl group, or a group of formula O—C(=O)A; in the presence of a catalyst and in the presence of a condensing agent in case $L^1$ represents a hydroxyl group, and in the presence of an acid binder in case $L^1$ represents a halogen atom.

N-[(trisubstitutedsilyl)methyl]amine derivatives of formula (II) wherein $Z^7$ is a substituted or non-substituted $C_1$-$C_8$-alkyl or a substituted or non-substituted $C_3$-$C_7$-cycloalkyl, can be prepared by known processes such as the nucleophilic substitution of a (halogenomethyl)-(dialkyl)arylsilane by the corresponding primary amine (Journal of Organometallic Chemistry (1978), 153, 193). N-[(trisubstitutedsilyl)methyl]amine derivatives of formula (II) wherein $Z^7$ is a hydrogen atom can be prepared by known processes such as the nucleophilic substitution of a (halogenomethyl)(dialkyl)arylsilane by ammonia (Journal of the Americam Chemical Society (1951), 73, 3867) or by phthalimide followed a deprotection by hydrazine (patent application EP0291787). Furthermore N-[(trisubstitutedsilyl)methyl] amine derivatives of formula (II) wherein $Z^7$ is a substituted or non-substituted $C_1$-$C_8$-alkyl or a substituted or non-substituted $C_3$-$C_7$-cycloalkyl, can be prepared by known processes from N-[(trisubstitutedsilyl)methyl]amine derivatives of formula (II) wherein $Z^7$ is a hydrogen atom by reductive amination with an aldehyde or ketone, or by nucleophilic substitution of a halogeno(cyclo)alkyl (Journal of Organic Chemistry (2005), 70, 8372).

Carboxylic acid derivatives of formula (III) can be prepared by known processes.

In case $L^1$ represents a hydroxy group, the process according to the present invention is conducted in the presence of condensing agent. Suitable condensing agent may be selected in the non limited list consisting of acid halide former, such as phosgene, phosphorous tribromide, phosphorous trichloride, phosphorous pentachloride, phosphorous trichloride oxide or thionyl chloride; anhydride former, such as ethyl chloroformate, methyl chloroformate, isopropyl chloroformate, isobutyl chloroformate or methanesulfonyl chloride; carbodiimides, such as N,N'-dicyclohexylcarbodiimide (DCC) or other customary condensing agents, such as phosphorous pentoxide, polyphosphoric acid, N,N'-carbonyl-diimidazole, 2-ethoxy-N-ethoxycarbonyl-1,2-dihydroquinoline (EEDQ), triphenylphosphine/tetrachloromethane, 4-(4,6-dimethoxy[1.3.5]-triazin-2-yl)-4-methylmorpholinium chloride hydrate, bromotripyrrolidino-phosphonium-hexafluorophosphate or propanephosphonic anhydride (T3P).

The process according to the present invention is conducted in the presence of a catalyst. Suitable catalyst may be selected in the list consisting of 4-dimethyl-aminopyridine, 1-hydroxy-benzotriazole or dimethylformamide.

In case $L^1$ represents a halogen atom, the process according to the present invention is conducted in the presence of an acid binder. Suitable acid binders for carrying out process P1 according to the invention are in each case all inorganic and organic bases that are customary for such reactions. Preference is given to using alkaline earth metal, alkali metal hydride, alkali metal hydroxides or alkali metal alkoxides, such as sodium hydroxide, sodium hydride, calcium hydroxide, potassium hydroxide, potassium tert-butoxide or other ammonium hydroxide, alkali metal carbonates, such as cesium carbonate, sodium carbonate, potassium carbonate, potassium bicarbonate, sodium bicarbonate, alkali metal or alkaline earth metal acetates, such as sodium acetate, potassium acetate, calcium acetate and also tertiary amines, such as trimethylamine, triethylamine, diisopropylethylamine, tributylamine, N,N-dimethylaniline, pyridine, N-methylpiperidine, N,N-dimethylaminopyridine, diazabicyclooctane (DABCO), diazabicyclo-nonene (DBN) or diazabicycloundecene (DBU).

It is also possible to work in the absence of an additional condensing agent or to employ an excess of the amine component, so that it simultaneously acts as acid binder agent.

According to a further aspect according to the invention, there is provided a process P2 for the preparation of a compound of formula (I) wherein T represents S, starting from a compound of formula (I) wherein T represents O and illustrated according to the following reaction scheme:

Scheme P2

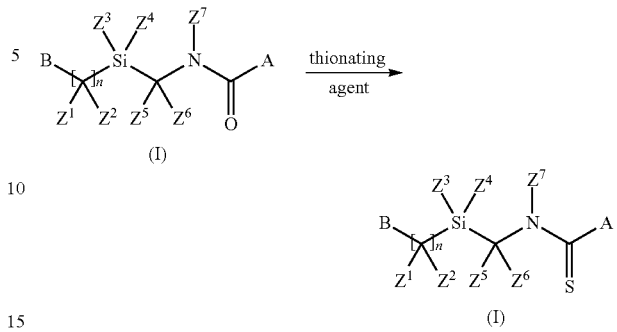

wherein A, B, n, $Z^1$, $Z^2$, $Z^3$, $Z^4$, $Z^5$, $Z^6$ and $Z^7$ are as herein-defined, in the optional presence of a catalytic or stoechiometric or more, quantity of a base such as an inorganic and organic base. Preference is given to using alkali metal carbonates, such as sodium carbonate, potassium carbonate, potassium bicarbonate, sodium bicarbonate; heterocyclic aromatic bases, such as pyridine, picoline, lutidine, collidine; and also tertiary amines, such as trimethylamine, triethylamine, tributylamine, N,N-dimethylaniline, N,N-dimethylaminopyridine or N-methyl-piperidine.

Process P2 according to the invention is performed in the presence of a thionating agent.

Starting amide derivatives of formula (I) can be prepared according to processes P1.

Suitable thionating agents for carrying out process P2 according to the invention can be sulfur (S), sulfhydric acid ($H_2S$), sodium sulfide ($Na_2S$), sodium hydrosulfide (NaHS), boron trisulfide ($B_2S_3$), bis(diethylaluminium) sulfide (($AlEt_2)_2S$), ammonium sulfide (($NH_4)_2S$), phosphorous pentasulfide ($P_2S_5$), Lawesson's reagent (2,4-bis(4-methoxyphenyl)-1,2,3,4-dithiadiphosphetane 2,4-disulfide) or a polymer-supported thionating reagent such as described in Journal of the Chemical Society, Perkin 1 (2001), 358.

The compound according to the present invention can be prepared according to the general processes of preparation described above. It will nevertheless be understood that, on the basis of his general knowledge and of available publications, the skilled worker will be able to adapt this method according to the specifics of each of the compounds, which it is desired to synthesize.

Still in a further aspect, the present invention relates to compounds of formula (II) useful as intermediate compounds or materials for the process of preparation according to the invention. The present invention thus provides compounds of formula (IIa):

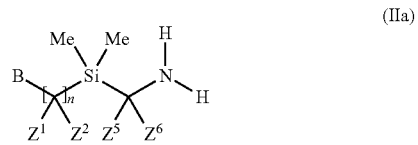

wherein B, n, $Z^1$, $Z^2$, $Z^5$ and $Z^6$ are as herein-defined with the exclusion of:
1-[dimethyl(phenyl)silyl]methanamine and its hydrochloride salt
1-[dimethyl(phenyl)silyl]ethanamine and its hydrochloride salt (1R)-1-[dimethyl(phenyl)silyl]ethanamine
1-[dimethyl(phenyl)silyl]propan-1-amine
1-[dimethyl(phenyl)silyl]pentan-1-amine and its hydrochloride salt
1-[dimethyl(phenyl)silyl]octan-1-amine
1-[(4-methoxyphenyl)(dimethyl)silyl]methanamine
1-[(3-fluorophenyl)(dimethyl)silyl]methanamine and its hydrochloride salt
1-[(4-fluorophenyl)(dimethyl)silyl]methanamine
1-[(4-chlorophenyl)(dimethyl)silyl]methanamine
1-[benzyl(dimethyl)silyl]methanamine and its hydrochloride salt
1-[(2-fluorobenzyl)(dimethyl)silyl]methanamine and its hydrochloride salt
1-[(3-fluorobenzyl)(dimethyl)silyl]methanamine and its hydrochloride salt
1-[(4-fluorobenzyl)(dimethyl)silyl]methanamine and its hydrochloride salt
1-[(4-chlorobenzyl)(dimethyl)silyl]methanamine
1-[(2,4-difluorobenzyl)(dimethyl)silyl]methanamine and its hydrochloride salt
1-[(2,6-difluorobenzyl)(dimethyl)silyl]methanamine and its hydrochloride salt
1-[(3,4-difluorobenzyl)(dimethyl)silyl]methanamine and its hydrochloride salt
1-[(3,5-difluorobenzyl)(dimethyl)silyl]methanamine
1-[(3,4-dichlorobenzyl)(dimethyl)silyl]methanamine
1-[dimethyl(2-thienylmethyl)silyl]methanamine.

The present invention thus also provides compounds of formula (IIb):

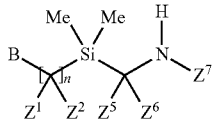

wherein B, n, $Z^1$, $Z^2$, $Z^5$ and $Z^6$ are as herein-defined, and $Z^7$ represents a cyclopropyl, cyclobutyl, cyclopentyl, cyclohexyl or cycloheptyl group with the exclusion of:
N-{[dimethyl-(phenyl)silyl]methyl}cyclohexanamine.

On the basis of the present description and his general knowledge and of available publications as for example Journal of Organometallic Chemistry (1978), 153, 193 or Journal of Organic Chemistry (2005), 70, 8372, the skilled person can prepare intermediate compound of formula (II) according to the present invention.

In a further aspect, the present invention also relates to a fungicide composition comprising an effective and non-phytotoxic amount of an active compound of formula (I).

The expression "effective and non-phytotoxic amount" means an amount of composition according to the invention that is sufficient to control or destroy the fungi present or liable to appear on the crops and that does not entail any appreciable symptom of phytotoxicity for the said crops. Such an amount can vary within a wide range depending on the fungus to be controlled, the type of crop, the climatic conditions and the compounds included in the fungicide composition according to the invention. This amount can be determined by systematic field trials that are within the capabilities of a person skilled in the art.

Thus, according to the invention, there is provided a fungicide composition comprising, as an active ingredient, an effective amount of a compound of formula (I) as herein defined and an agriculturally acceptable support, carrier or filler.

According to the invention, the term "support" denotes a natural or synthetic, organic or inorganic compound with that the active compound of formula (I) is combined or associated to make it easier to apply, notably to the parts of the plant. This support is thus generally inert and should be agriculturally acceptable. The support can be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports can also be used.

The composition according to the invention can also comprise additional components. In particular, the composition can further comprise a surfactant. The surfactant can be an emulsifier, a dispersing agent or a wetting agent of ionic or non-ionic type or a mixture of such surfactants. Mention can be made, for example, of polyacrylic acid salts, lignosulfonic acid salts, phenolsulfonic or naphthalenesulfonic acid salts, polycondensates of ethylene oxide with fatty alcohols or with fatty acids or with fatty amines, substituted phenols (in particular alkylphenols or arylphenols), salts of sulfosuccinic acid esters, taurine derivatives (in particular alkyl taurates), phosphoric esters of polyoxyethylated alcohols or phenols, fatty acid esters of polyols and derivatives of the above compounds containing sulfate, sulfonate and phosphate functions. The presence of at least one surfactant is generally essential when the active compound and/or the inert support are water-insoluble and when the vector agent for the application is water. Preferably, surfactant content can be comprised from 5% to 40% by weight of the composition.

Optionally, additional components can also be included, e.g. protective colloids, adhesives, thickeners, thixotropic agents, penetration agents, stabilisers, sequestering agents. More generally, the active compounds can be combined with any solid or liquid additive, that complies with the usual formulation techniques.

In general, the composition according to the invention can contain from 0.05 to 99% by weight of active compound, preferably 10 to 70% by weight.

Compositions according to the invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ULV) liquid, ultra low volume (ULV) suspension, water dispersible granules or tablets, water dispersible powder for slurry treatment, water soluble granules or tablets, water soluble powder for seed treatment and wettable powder. These compositions include not only compositions that are ready to be applied to the plant or seed to be treated by means of a suitable device, such as a spraying or dusting device, but also concentrated commercial compositions that must be diluted before application to the crop.

The compounds according to the invention can also be mixed with one or more insecticide, fungicide, bactericide, attractant, acaricide or pheromone active substance or other compounds with biological activity.

The compounds of formula (I) and the fungicide composition according to the invention can be used to curatively or preventively control the phytopathogenic fungi of plants or crops.

Thus, according to a further aspect of the invention, there is provided a method for curatively or preventively controlling the phytopathogenic fungi of plants or crops characterised in that a compound of formula (I) or a fungicide composition according to the invention is applied to the seed, the plant or to the fruit of the plant or to the soil wherein the plant is growing or wherein it is desired to grow.

The method of treatment according to the invention can also be useful to treat propagation material such as tubers or rhizomes, but also seeds, seedlings or seedlings pricking out and plants or plants pricking out. This method of treatment can also be useful to treat roots. The method of treatment according to the invention can also be useful to treat the overground parts of the plant such as trunks, stems or stalks, leaves, flowers and fruit of the concerned plant.

According to the invention all plants and plant parts can be treated. By plants is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. By plant parts is meant all above ground and below ground parts and organs of plants such as shoot, leaf, blossom and root, whereby for example leaves, needles, stems, branches, blossoms, fruiting bodies, fruits and seed as well as roots, corms and rhizomes are listed. Crops and vegetative and generative propagating material, for example cuttings, corms, rhizomes, runners and seeds also belong to plant parts.

Among the plants that can be protected by the method according to the invention, mention may be made of major field crops like corn, soybean, cotton, *Brassica* oilseeds such as *Brassica napus* (e.g. canola), *Brassica rapa, B. juncea* (e.g. mustard) and *Brassica carinata*, rice, wheat, sugarbeet, sugarcane, oats, rye, barley, millet, triticale, flax, vine and various fruits and vegetables of various botanical taxa such as Rosaceae sp. (for instance pip fruit such as apples and pears, but also stone fruit such as apricots, cherries, almonds and peaches, berry fruits such as strawberries), Ribesioidae sp., Juglandaceae sp., Betulaceae sp., Anacardiaceae sp., Fagaceae sp., Moraceae sp., Oleaceae sp., Actinidaceae sp., Lauraceae sp., Musaceae sp. (for instance banana trees and plantings), Rubiaceae sp. (for instance coffee), Theaceae sp., Sterculiceae sp., Rutaceae sp. (for instance lemons, oranges and grapefruit); Solanaceae sp. (for instance tomatoes, potatoes, peppers, eggplant), Liliaceae sp., Compositiae sp. (for instance lettuce, artichoke and chicory—including root chicory, endive or common chicory), Umbelliferae sp. (for instance carrot, parsley, celery and celeriac), Cucurbitaceae sp. (for instance cucumber—including pickling cucumber, squash, watermelon, gourds and melons), Alliaceae sp. (for instance onions and leek), Cruciferae sp. (for instance white cabbage, red cabbage, broccoli, cauliflower, brussel sprouts, pak choi, kohlrabi, radish, horseradish, cress, Chinese cabbage), Leguminosae sp. (for instance peanuts, peas and beans beans—such as climbing beans and broad beans), Chenopodiaceae sp. (for instance mangold, spinach beet, spinach, beetroots), Malvaceae (for instance okra), Asparagaceae (for instance asparagus); horticultural and forest crops; ornamental plants; as well as genetically modified homologues of these crops.

The method of treatment according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology, RNA interference—RNAi—technology or microRNA—miRNA—technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are also suitable for mobilizing the defense system of the plant against attack by unwanted microorganisms. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted microorganisms, the treated plants display a substantial degree of resistance to these microorganisms. In the present case, unwanted microorganisms are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids. Examples of nematode resistant plants are described in e.g. U.S. patent application Ser. Nos. 11/765,491, 11/765,494, 10/926,819, 10/782,020, 12/032,479, 10/783,417, 10/782,096, 11/657,964, 12/192,904, 11/396,808, 12/166,253, 12/166,239, 12/166,124, 12/166,209, 11/762,886, 12/364,335, 11/763,947, 12/252,453, 12/209,354, 12/491,396, 12/497,221, 12/644,632, 12/646,004, 12/701,058, 12/718,059, 12/721,595, 12/638,591 and in WO11/002992, WO11/014749, WO11/103247, WO11/103248.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stresses). Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species (WO 92/05251, WO 95/09910, WO 98/27806, WO 05/002324, WO 06/021972 and U.S. Pat. No. 6,229,072). However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar (e.g. WO 91/02069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-resistant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., 1983, Science 221, 370-371), the CP4 gene of the bacterium *Agrobacterium* sp. (Barry et al., 1992, Curr. Topics Plant Physiol. 7, 139-145), the genes encoding a *Petunia* EPSPS (Shah et al., 1986, Science 233, 478-481), a Tomato EPSPS (Gasser et al., 1988, J. Biol. Chem. 263, 4280-4289), or an *Eleusine* EPSPS (WO 01/66704). It can also be a mutated EPSPS as described in for example EP 0837944, WO 00/66746, WO 00/66747, WO02/26995, WO11/000498. Glyphosate-tolerant plants can also be obtained by expressing a gene that encodes a glyphosate oxido-reductase enzyme as described in U.S. Pat. Nos. 5,776,760 and 5,463,175. Glyphosate-tolerant plants can also be obtained by expressing a gene that encodes a glyphosate acetyl transferase enzyme as described in for example WO 02/36782, WO 03/092360, WO 05/012515 and WO 07/024782. Glyphosate-tolerant plants can also be obtained by selecting plants containing naturally-occurring mutations of the above-mentioned genes, as described in for example WO 01/024615 or WO 03/013226. Plants expressing EPSPS genes that confer glyphosate tolerance are described in e.g. U.S. patent application Ser. Nos. 11/517,991, 10/739,610, 12/139,408, 12/352,532, 11/312,866, 11/315,678, 12/421,292, 11/400,598, 11/651,752, 11/681,285, 11/605,824, 12/468,205, 11/760,570, 11/762,526, 11/769,327, 11/769,255, 11/943801 or 12/362,774. Plants comprising other genes that confer glyphosate tolerance, such as decarboxylase genes, are described in e.g. U.S. patent application Ser. Nos. 11/588,811, 11/185,342, 12/364,724, 11/185,560 or 12/423,926.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition, e.g. described in U.S. patent application Ser. No. 11/760,602. One such efficient detoxifying enzyme is an enzyme encoding a phosphinothricin acetyltransferase (such as the bar or pat protein from *Streptomyces* species). Plants expressing an exogenous phosphinothricin acetyltransferase are for example described in U.S. Pat. Nos. 5,561,236; 5,648,477; 5,646,024; 5,273,894; 5,637,489; 5,276,268; 5,739,082; 5,908,810 and 7,112,665.

Further herbicide-tolerant plants are also plants that are made tolerant to the herbicides inhibiting the enzyme hydroxyphenylpyruvatedioxygenase (HPPD). HPPD is an enzyme that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated or chimeric HPPD enzyme as described in WO 96/38567, WO 99/24585, WO 99/24586, WO 2009/144079, WO 2002/046387, or U.S. Pat. No. 6,768,044, WO11/076877, WO11/076882, WO11/076885, WO11/076889, WO11/076892. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 99/34008 and WO 02/36787. Tolerance of plants to HPPD inhibitors can also be improved by transforming plants with a gene encoding an enzyme having prephenate deshydrogenase (PDH) activity in addition to a gene encoding an HPPD-tolerant enzyme, as described in WO 2004/024928. Further, plants can be made more tolerant to HPPD-inhibitor herbicides by adding into their genome a gene encoding an enzyme capable of metabolizing or degrading HPPD inhibitors, such as the CYP450 enzymes shown in WO 2007/103567 and WO 2008/150473.

Still further herbicide resistant plants are plants that are made tolerant to acetolactate synthase (ALS) inhibitors. Known ALS-inhibitors include, for example, sulfonylurea, imidazolinone, triazolopyrimidines, pryimidinyoxy(thio)benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright (2002, Weed Science 50:700-712), but also, in U.S. Pat. Nos. 5,605,011, 5,378,824, 5,141,870, and 5,013,659. The production of sulfonylurea-tolerant plants and imidazolinone-tolerant plants is described in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270. Other imidazolinone-tolerant plants are also described in for example WO 2004/040012, WO 2004/106529, WO 2005/020673, WO 2005/093093, WO 2006/007373, WO 2006/015376, WO 2006/024351, and WO 2006/060634. Further sulfonylurea- and imidazolinone-tolerant plants are also described in for example WO 07/024782, WO11/076345, WO2012058223 and US Patent Application No 61/288958.

Other plants tolerant to imidazolinone and/or sulfonylurea can be obtained by induced mutagenesis, selection in cell cultures in the presence of the herbicide or mutation breeding as described for example for soybeans in U.S. Pat. No. 5,084,082, for rice in WO 97/41218, for sugar beet in U.S. Pat. No. 5,773,702 and WO 99/057965, for lettuce in U.S. Pat. No. 5,198,599, or for sunflower in WO 01/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al. (1998, Microbiology and Molecular Biology Reviews, 62: 807-813), updated by Crickmore et al. (2005) at the *Bacillus thuringiensis* toxin nomenclature, online at: http://www.lifesci.sussex.ac.uk/Home/Neil_Crickmore/Bt/), or insecticidal portions thereof, e.g., proteins of the Cry protein classes Cry1Ab, Cry1Ac, Cry1B, Cry1C, Cry1D, Cry1F, Cry2Ab, Cry3Aa, or Cry3Bb or insecticidal portions thereof (e.g. EP 1999141 and WO 2007/107302), or such proteins encoded by synthetic genes as e.g. described in and U.S. patent application Ser. No. 12/249,016; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (Moellenbeck et al. 2001, Nat. Biotechnol. 19: 668-72; Schnepf et al. 2006, Applied Environm. Microbiol. 71, 1765-1774) or the binary toxin made up of the Cry1A or Cry1F proteins and the Cry2Aa or Cry2Ab or Cry2Ae proteins (U.S. patent application Ser. No. 12/214,022 and EP 08010791.5); or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A. 105 protein produced by corn event MON89034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604; or 5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g., proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 5) to 7) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102; or 9) a secreted protein from *Bacillus thuringiensis* or *Bacillus cereus* which is insecticidal in the presence of a crystal protein from *Bacillus thuringiensis*, such as the binary toxin made up of VIP3 and Cry1A or Cry1F (U.S. Patent Appl. No. 61/126,083 and 61/195,019), or the binary toxin made up of the VIP3 protein and the Cry2Aa or Cry2Ab or Cry2Ae proteins (U.S. patent application Ser. No. 12/214,022 and EP 08010791.5).
10) a protein of 9) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein)

Of course, an insect-resistant transgenic plant, as used herein, also includes any plant comprising a combination of genes encoding the proteins of any one of the above classes 1 to 10. In one embodiment, an insect-resistant plant contains more than one transgene encoding a protein of any one of the above classes 1 to 10, to expand the range of target insect species affected when using different proteins directed at different target insect species, or to delay insect resistance development to the plants by using different proteins insecticidal to the same target insect species but having a different mode of action, such as binding to different receptor binding sites in the insect.

An "insect-resistant transgenic plant", as used herein, further includes any plant containing at least one transgene comprising a sequence producing upon expression a double-stranded RNA which upon ingestion by a plant insect pest inhibits the growth of this insect pest, as described e.g. in WO 2007/080126, WO 2006/129204, WO 2007/074405, WO 2007/080127 and WO 2007/035650.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

1) plants which contain a transgene capable of reducing the expression and/or the activity of poly(ADP-ribose) polymerase (PARP) gene in the plant cells or plants as described in WO 00/04173, WO/2006/045633, EP 04077984.5, or EP 06009836.5.
2) plants which contain a stress tolerance enhancing transgene capable of reducing the expression and/or the activity of the PARG encoding genes of the plants or plants cells, as described e.g. in WO 2004/090140.
3) plants which contain a stress tolerance enhancing transgene coding for a plant-functional enzyme of the nicotineamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase as described e.g. in EP 04077624.7, WO 2006/133827, PCT/EP07/002433, EP 1999263, or WO 2007/107326.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications. Said transgenic plants synthesizing a modified starch are disclosed, for example, in EP 0571427, WO 95/04826, EP 0719338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO99/58688, WO 99/58690, WO 99/58654, WO 00/08184, WO 00/08185, WO 00/08175, WO 00/28052, WO 00/77229, WO 01/12782, WO 01/12826, WO 02/101059, WO 03/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 00/22140, WO 2006/063862, WO 2006/072603, WO 02/034923, EP 06090134.5, EP 06090228.5, EP 06090227.7, EP 07090007.1, EP 07090009.7, WO 01/14569, WO 02/79410, WO 03/33540, WO 2004/078983, WO 01/19975, WO 95/26407, WO 96/34968, WO 98/20145, WO 99/12950, WO 99/66050, WO 99/53072, U.S. Pat. No. 6,734,341, WO 00/11192, WO 98/22604, WO 98/32326, WO 01/98509, WO 01/98509, WO 2005/002359, U.S. Pat. No. 5,824,790, U.S. Pat. No. 6,013,861, WO 94/04693, WO 94/09144, WO 94/11520, WO 95/35026, WO 97/20936, WO 10/012796, WO 10/003701
2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, as disclosed in EP 0663956, WO 96/01904, WO 96/21023, WO 98/39460, and WO 99/24593, plants producing alpha-1,4-glucans as disclosed in WO 95/31553, US 2002031826, U.S. Pat. No. 6,284,479, U.S. Pat. No. 5,712,107, WO 97/47806, WO 97/47807, WO 97/47808 and WO 00/14249, plants producing alpha-1,6 branched alpha-1,4-glucans, as disclosed in WO 00/73422, plants producing alternan, as disclosed in e.g. WO 00/47727, WO 00/73422, EP 06077301.7, U.S. Pat. No. 5,908,975 and EP 0728213,
3) transgenic plants which produce hyaluronan, as for example disclosed in WO 2006/032538, WO 2007/039314, WO 2007/039315, WO 2007/039316, JP 2006304779, and WO 2005/012529.
4) transgenic plants or hybrid plants, such as onions with characteristics such as 'high soluble solids content', 'low pungency' (LP) and/or 'long storage' (LS), as described in U.S. patent application Ser. No. 12/020,360 and 61/054,026.
5) Transgenic plants displaying an increase yield as for example disclosed in WO11/095528

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics and include:
  a) Plants, such as cotton plants, containing an altered form of cellulose synthase genes as described in WO 98/00549
  b) Plants, such as cotton plants, containing an altered form of rsw2 or rsw3 homologous nucleic acids as described in WO 2004/053219
  c) Plants, such as cotton plants, with increased expression of sucrose phosphate synthase as described in WO 01/17333
  d) Plants, such as cotton plants, with increased expression of sucrose synthase as described in WO 02/45485
  e) Plants, such as cotton plants, wherein the timing of the plasmodesmatal gating at the basis of the fiber cell is altered, e.g. through downregulation of fiber-selective β-1,3-glucanase as described in WO 2005/017157, or as described in EP 08075514.3 or US Patent Appl. No. 61/128,938
  f) Plants, such as cotton plants, having fibers with altered reactivity, e.g. through the expression of N-acetylglucosaminetransferase gene including nodC and chitin synthase genes as described in WO 2006/136351 WO11/089021, WO2012074868

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants contain a mutation imparting such altered oil profile characteristics and include:
  a) Plants, such as oilseed rape plants, producing oil having a high oleic acid content as described e.g. in U.S. Pat. Nos. 5,969,169, 5,840,946 or 6,323,392 or 6,063,947
  b) Plants such as oilseed rape plants, producing oil having a low linolenic acid content as described in U.S. Pat. Nos. 6,270,828, 6,169,190, 5,965,755, or WO11/060946.
  c) Plant such as oilseed rape plants, producing oil having a low level of saturated fatty acids as described e.g. in U.S. Pat. No. 5,434,283 or U.S. patent application Ser. No. 12/668,303
  d) Plants such as oilseed rape plants, producing oil having an aleter glucosinolate content as described in WO2012075426.

Plants or plant cultivars (that can be obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering as described in U.S. Patent Appl. No. 61/135,230, WO09/068313, WO10/006732 and WO2012090499.

Plants or plant cultivars (that can be obtained by plant biotechnology methods such as genetic engineering) which may also be treated according to the invention are plants, such as Tobacco plants, with altered post-translational protein modification patterns, for example as described in WO 10/121818 and WO 10/145846

Particularly useful transgenic plants which may be treated according to the invention are plants containing transformation events, or combination of transformation events, that are the subject of petitions for non-regulated status, in the United States of America, to the Animal and Plant Health Inspection Service (APHIS) of the United States Department of Agriculture (USDA) whether such petitions are granted or are still pending. At any time this information is readily available from APHIS (4700 River Road Riverdale, Md. 20737, USA), for instance on its internet site (URL http://www.aphis.usda.gov/brs/not_reg.html). On the filing date of this application the petitions for nonregulated status that were pending with APHIS or granted by APHIS were those which contains the following information:
  Petition: the identification number of the petition. Technical descriptions of the transformation events can be found in the individual petition documents which are obtainable from APHIS, for example on the APHIS website, by reference to this petition number. These descriptions are herein incorporated by reference.
  Extension of Petition: reference to a previous petition for which an extension is requested.
  Institution: the name of the entity submitting the petition.
  Regulated article: the plant species concerned.
  Transgenic phenotype: the trait conferred to the plants by the transformation event.
  Transformation event or line: the name of the event or events (sometimes also designated as lines or lines) for which nonregulated status is requested.
  APHIS documents: various documents published by APHIS in relation to the Petition and which can be requested with APHIS.

Additional particularly useful plants containing single transformation events or combinations of transformation events are listed for example in the databases from various national or regional regulatory agencies (see for example http://gmoinfo.jrc.it/gmp_browse.aspx and http://www.agbios.com/dbase.php).

Particularly useful transgenic plants which may be treated according to the invention are plants containing transformation events, or a combination of transformation events, and that are listed for example in the databases for various national or regional regulatory agencies including Event 1143-14A (cotton, insect control, not deposited, described in WO2006/128569); Event 1143-51B (cotton, insect control, not deposited, described in WO2006/128570); Event 1445 (cotton, herbicide tolerance, not deposited, described in US2002120964 or WO2002/034946); Event 17053 (rice, herbicide tolerance, deposited as PTA-9843, described in WO2010/117737); Event 17314 (rice, herbicide tolerance, deposited as PTA-9844, described in WO2010/117735); Event 281-24-236 (cotton, insect control—herbicide tolerance, deposited as PTA-6233, described in WO2005/103266 or US2005216969); Event 3006-210-23 (cotton, insect control—herbicide tolerance, deposited as PTA-6233, described in US2007143876 or WO2005/103266); Event 3272 (corn, quality trait, deposited as PTA-9972, described in WO2006098952 or US2006230473); Event 40416 (corn, insect control—herbicide tolerance, deposited as ATCC PTA-11508, described in WO2011/075593); Event 43A47 (corn, insect control—herbicide tolerance, deposited as ATCC PTA-11509, described in WO2011/075595); Event 5307 (corn, insect control, deposited as ATCC PTA-9561, described in WO2010/077816); Event ASR-368 (bent grass, herbicide tolerance, deposited as ATCC PTA-4816, described in US2006162007 or WO2004053062); Event B16 (corn, herbicide tolerance, not deposited, described in US2003126634); Event BPS-CV127-9 (soybean, herbicide tolerance, deposited as NCIMB No. 41603, described in WO2010/080829); Event CE43-67B (cotton, insect control, deposited as DSM ACC2724, described in US2009217423 or WO2006/128573); Event CE44-69D (cotton, insect control, not deposited, described in US20100024077); Event CE44-69D (cotton, insect control, not deposited, described in WO2006/128571); Event CE46-02A (cotton, insect control, not deposited, described in WO2006/128572); Event COT102 (cotton, insect control, not deposited, described in US2006130175 or WO2004039986); Event COT202 (cotton, insect control, not deposited, described in US2007067868 or WO2005054479); Event COT203 (cotton, insect control, not deposited, described in WO2005/054480); Event DAS40278 (corn, herbicide tolerance, deposited as ATCC PTA-10244, described in WO2011/022469); Event DAS-59122-7 (corn, insect control—herbicide tolerance, deposited as ATCC PTA 11384, described in US2006070139); Event DAS-59132 (corn, insect control—herbicide tolerance, not deposited, described in WO2009/100188); Event DAS68416 (soybean, herbicide tolerance, deposited as ATCC PTA-10442, described in WO2011/066384 or WO2011/066360); Event DP-098140-6 (corn, herbicide tolerance, deposited as ATCC PTA-8296, described in US2009137395 or WO2008/112019); Event DP-305423-1 (soybean, quality trait, not deposited, described in US2008312082 or WO2008/054747); Event DP-32138-1 (corn, hybridization system, deposited as ATCC PTA-9158, described in US20090210970 or WO2009/103049); Event DP-356043-5 (soybean, herbicide tolerance, deposited as ATCC PTA-8287, described in US20100184079 or WO2008/002872); Event EE-1 (brinjal, insect control, not deposited, described in WO2007/091277); Event FI117 (corn, herbicide tolerance, deposited as ATCC 209031, described in US2006059581 or WO1998/044140); Event GA21 (corn, herbicide tolerance, deposited as ATCC 209033, described in US2005086719 or WO1998/044140); Event GG25 (corn, herbicide tolerance, deposited as ATCC 209032, described in US2005188434 or WO1998/044140); Event GHB119 (cotton, insect control—herbicide tolerance, deposited as ATCC PTA-8398, described in WO2008/151780); Event GHB614 (cotton, herbicide tolerance, deposited as ATCC PTA-6878, described in US2010050282 or WO2007/017186); Event GJ11 (corn, herbicide tolerance, deposited as ATCC 209030, described in US2005188434 or WO1998/044140); Event GM RZ13 (sugar beet, virus resistance, deposited as NCIMB-41601, described in WO2010/076212); Event H7-1 (sugar beet, herbicide tolerance, deposited as NCIMB 41158 or NCIMB 41159, described in US2004172669 or WO2004/074492); Event JOPLIN1 (wheat, disease tolerance, not deposited, described in US2008064032); Event LL27 (soybean, herbicide tolerance, deposited as NCIMB41658, described in WO2006/108674 or US2008320616); Event LL55 (soybean, herbicide tolerance, deposited as NCIMB 41660, described in WO2006/108675 or US2008196127); Event LLcotton25 (cotton, herbicide tolerance, deposited as ATCC PTA-3343, described in WO2003013224 or US2003097687); Event LLRICE06 (rice, herbicide tolerance, deposited as ATCC-23352, described in U.S. Pat. No. 6,468,747 or WO2000/026345); Event LLRICE601 (rice, herbicide tolerance, deposited as ATCC PTA-2600, described in US20082289060 or WO2000/026356); Event LY038 (corn, quality trait, deposited as ATCC PTA-5623, described in US2007028322 or WO2005061720); Event MIR162 (corn, insect control, deposited as PTA-8166, described in US2009300784 or WO2007/142840); Event MIR604 (corn, insect control, not deposited, described in US2008167456 or WO2005103301); Event MON15985 (cotton, insect control, deposited as ATCC PTA-2516, described in US2004-250317 or WO2002/100163); Event MON810 (corn, insect control, not deposited, described in US2002102582); Event MON863 (corn, insect control, deposited as ATCC PTA-2605, described in WO2004/011601 or US2006095986); Event MON87427 (corn, pollination control, deposited as ATCC PTA-7899, described in WO2011/062904); Event MON87460 (corn, stress tolerance, deposited as ATCC PTA-8910, described in WO2009/111263 or US20110138504); Event MON87701 (soybean, insect control, deposited as ATCC PTA-8194, described in US2009130071 or WO2009/064652); Event MON87705 (soybean, quality trait—herbicide tolerance, deposited as ATCC PTA-9241, described in US20100080887 or WO2010/037016); Event MON87708 (soybean, herbicide tolerance, deposited as ATCC PTA9670, described in WO2011/034704); Event MON87754 (soybean, quality trait, deposited as ATCC PTA-9385, described in WO2010/024976); Event MON87769 (soybean, quality trait, deposited as ATCC PTA-8911, described in US20110067141 or WO2009/102873); Event MON88017 (corn, insect control—herbicide tolerance, deposited as ATCC PTA-5582, described in US2008028482 or WO2005/059103); Event MON88913 (cotton, herbicide tolerance, deposited as ATCC PTA-4854, described in WO2004/072235 or US2006059590); Event MON89034 (corn, insect control, deposited as ATCC PTA-7455, described in WO2007/140256 or US2008260932); Event MON89788 (soybean, herbicide tolerance, deposited as ATCC PTA-6708, described in US2006282915 or WO2006/130436); Event MS11 (oilseed rape, pollination control—herbicide tolerance, deposited as ATCC PTA-850 or PTA-2485, described in WO2001/031042); Event MS8, (oilseed rape, pollination control—herbicide tolerance, deposited as ATCC PTA-730, described in WO2001/041558 or US2003188347); Event NK603 (corn, herbicide tolerance, deposited as ATCC PTA-2478, described in US2007-292854); Event PE-7 (rice, insect control, not deposited, described in WO2008/114282); Event RF3, (oilseed rape, pollination control—herbicide tolerance, deposited as ATCC PTA-730, described in WO2001/041558 or US2003188347); Event RT73 (oilseed rape, herbicide tolerance, not deposited, described in WO2002/036831 or US2008070260); Event T227-1 (sugar beet, herbicide tolerance, not deposited, described in WO2002/44407 or US2009265817); Event T25 (corn, herbicide tolerance, not deposited, described in US2001029014 or WO2001/051654); Event T304-40 (cotton, insect control—herbicide tolerance, deposited as ATCC PTA-8171, described in US2010077501 or WO2008/122406); Event T342-142 (cotton, insect control, not deposited, described in WO2006/128568); Event TC1507 (corn, insect control—herbicide tolerance, not deposited, described in US2005039226 or WO2004/099447); Event VIP1034 (corn, insect control—herbicide tolerance, deposited as ATCC PTA-3925., described in WO2003/052073), Event 32316 (corn, insect control-herbicide tolerance, deposited as PTA-11507, described in WO2011/153186A1), Event 4114 (corn, insect control-herbicide tolerance, deposited as PTA-11506, described in WO2011/084621), event EE-GM3/FG72 (soybean, herbicide tolerance, ATCC Accession N° PTA-11041, WO2011/063413A2), event DAS-68416-4 (soybean, herbicide tolerance, ATCC Accession N° PTA-10442, WO2011/066360A1), event DAS-68416-4 (soybean, herbicide tolerance, ATCC Accession N° PTA-10442, WO2011/066384A1), event DP-040416-8 (corn, insect control, ATCC Accession N° PTA-11508, WO2011/075593A1), event DP-043A47-3 (corn, insect control, ATCC Accession N° PTA-11509, WO2011/075595A1), event DP-004114-3 (corn, insect control, ATCC Accession N° PTA-11506, WO2011/084621A1), event DP-032316-8 (corn, insect control, ATCC Accession N° PTA-11507, WO2011/084632A1), event MON-88302-9 (oilseed rape, herbicide tolerance, ATCC Accession N° PTA-10955, WO2011/153186A1), event DAS-21606-3 (soybean, herbicide tolerance, ATCC Accession N° . PTA-11028, WO2012/033794A2), event MON-87712-4 (soybean, quality trait, ATCC Accession N° . PTA-10296, WO2012/051199A2), event DAS-44406-6 (soybean, stacked herbicide tolerance, ATCC Accession N° . PTA-11336, WO2012/075426A1), event DAS-14536-7 (soybean, stacked herbicide tolerance, ATCC Accession N° . PTA-11335, WO2012/075429A1), event SYN-000H2-5 (soybean, herbicide tolerance, ATCC Accession N° . PTA-11226, WO2012/082548A2), event DP-061061-7 (oilseed rape, herbicide tolerance, no deposit N° available, WO2012071039A1), event DP-073496-4 (oilseed rape, herbicide tolerance, no deposit N° available, US2012131692), event 8264.44.06.1 (soybean, stacked herbicide tolerance, Accession N° PTA-11336, WO2012075426A2), event 8291.45.36.2 (soybean, stacked herbicide tolerance, Accession N° . PTA-11335, WO2012075429A2).

Among the diseases of plants or crops that can be controlled by the method according to the invention, mention can be made of:

Powdery mildew diseases such as:
Blumeria diseases, caused for example by *Blumeria graminis*;
Podosphaera diseases, caused for example by *Podosphaera leucotricha*;
Sphaerotheca diseases, caused for example by *Sphaerotheca fuliginea*;
Uncinula diseases, caused for example by *Uncinula necator*;
Rust diseases such as:
Gymnosporangium diseases, caused for example by *Gymnosporangium sabinae*;
Hemileia diseases, caused for example by *Hemileia vastatrix*;
Phakopsora diseases, caused for example by *Phakopsora pachyrhizi* or *Phakopsora meibomiae*;
Puccinia diseases, caused for example by *Puccinia recondite*, *Puccinia graminis* or *Puccinia striiformis*;
Uromyces diseases, caused for example by *Uromyces appendiculatus*;
Oomycete diseases such as:
Albugo diseases caused for example by *Albugo candida*;
Bremia diseases, caused for example by *Bremia lactucae*;
Peronospora diseases, caused for example by *Peronospora pisi* or *P. brassicae*;
Phytophthora diseases, caused for example by *Phytophthora infestans*;
Plasmopara diseases, caused for example by *Plasmopara viticola*;
Pseudoperonospora diseases, caused for example by *Pseudoperonospora humuli* or *Pseudoperonospora cubensis*;
Pythium diseases, caused for example by *Pythium ultimum*;
Leafspot, leaf blotch and leaf blight diseases such as:
Alternaria diseases, caused for example by *Alternaria solani*;
Cercospora diseases, caused for example by *Cercospora beticola*;
Cladiosporum diseases, caused for example by *Cladiosporium cucumerinum*;
Cochliobolus diseases, caused for example by *Cochliobolus sativus* (Conidiaform: *Drechslera*, Syn: *Helminthosporium*) or *Cochliobolus miyabeanus*;
Colletotrichum diseases, caused for example by *Colletotrichum lindemuthanium*;
Cycloconium diseases, caused for example by *Cycloconium oleaginum*;
Diaporthe diseases, caused for example by *Diaporthe citri*;
Elsinoe diseases, caused for example by *Elsinoe fawcettii*;
Gloeosporium diseases, caused for example by *Gloeosporium laeticolor*;
Glomerella diseases, caused for example by *Glomerella cingulata*;
Guignardia diseases, caused for example by *Guignardia bidwelli*;
Leptosphaeria diseases, caused for example by *Leptosphaeria maculans*; *Leptosphaeria nodorum*;
Magnaporthe diseases, caused for example by *Magnaporthe grisea*;
Mycosphaerella diseases, caused for example by *Mycosphaerella graminicola*; *Mycosphaerella arachidicola*; *Mycosphaerella fijiensis*;
Phaeosphaeria diseases, caused for example by *Phaeosphaeria nodorum*;
Pyrenophora diseases, caused for example by *Pyrenophora teres*, or *Pyrenophora tritici repentis*;
Ramularia diseases, caused for example by *Ramularia collo-cygni*, or *Ramularia areola*;
Rhynchosporium diseases, caused for example by *Rhynchosporium secalis*;
Septoria diseases, caused for example by *Septoria apii* or *Septoria lycopercisi*;
Typhula diseases, caused for example by *Typhula incamata*;
Venturia diseases, caused for example by *Venturia inaequalis*;
Root, Sheath and stem diseases such as:
Corticium diseases, caused for example by *Corticium graminearum*;
Fusarium diseases, caused for example by *Fusarium oxysporum*;
Gaeumannomyces diseases, caused for example by *Gaeumannomyces graminis*;
Rhizoctonia diseases, caused for example by *Rhizoctonia solani*;
Sarocladium diseases caused for example by *Sarocladium oryzae*;
Sclerotium diseases caused for example by *Sclerotium oryzae*;
Tapesia diseases, caused for example by *Tapesia acuformis*;
Thielaviopsis diseases, caused for example by *Thielaviopsis basicola*;
Ear and panicle diseases such as:
Alternaria diseases, caused for example by *Alternaria* spp.;
Aspergillus diseases, caused for example by *Aspergillus flavus*;
Cladosporium diseases, caused for example by *Cladosporium* spp.;
Claviceps diseases, caused for example by *Claviceps purpurea*;
Fusarium diseases, caused for example by *Fusarium culmorum*;
Gibberella diseases, caused for example by *Gibberella zeae*;

*Monographella* diseases, caused for example by *Monographella nivalis;*
Smut and bunt diseases such as:
*Sphacelotheca* diseases, caused for example by *Sphacelotheca reiliana;*
*Tilletia* diseases, caused for example by *Tilletia caries;*
*Urocystis* diseases, caused for example by *Urocystis occulta;*
*Ustilago* diseases, caused for example by *Ustilago nuda;*
Fruit rot and mould diseases such as:
*Aspergillus* diseases, caused for example by *Aspergillus flavus;*
*Botrytis* diseases, caused for example by *Botrytis cinerea;*
*Penicillium* diseases, caused for example by *Penicillium expansum;*
*Rhizopus* diseases caused by example by *Rhizopus stolonifer*
*Sclerotinia* diseases, caused for example by *Sclerotinia sclerotiorum;*
*Verticilium* diseases, caused for example by *Verticilium alboatrum;*
Seed and soilborne decay, mould, wilt, rot and damping-off diseases:
*Alternaria* diseases, caused for example by *Alternaria brassicicola*
*Aphanomyces* diseases, caused for example by *Aphanomyces euteiches*
*Ascochyta* diseases, caused for example by *Ascochyta lentis*
*Aspergillus* diseases, caused for example by *Aspergillus flavus*
*Cladosporium* diseases, caused for example by *Cladosporium herbarum*
*Cochliobolus* diseases, caused for example by *Cochliobolus sativus* (Conidiaform: *Drechslera, Bipolaris* Syn: *Helminthosporium*);
*Colletotrichum* diseases, caused for example by *Colletotrichum coccodes;*
*Fusarium* diseases, caused for example by *Fusarium culmorum;*
*Gibberella* diseases, caused for example by *Gibberella zeae;*
*Macrophomina* diseases, caused for example by *Macrophomina phaseolina*
*Monographella* diseases, caused for example by *Monographella nivalis;*
*Penicillium* diseases, caused for example by *Penicillium expansum*
*Phoma* diseases, caused for example by *Phoma lingam*
*Phomopsis* diseases, caused for example by *Phomopsis sojae;*
*Phytophthora* diseases, caused for example by *Phytophthora cactorum;*
*Pyrenophora* diseases, caused for example by *Pyrenophora graminea*
*Pyricularia* diseases, caused for example by *Pyricularia oryzae;*
*Pythium* diseases, caused for example by *Pythium ultimum;*
*Rhizoctonia* diseases, caused for example by *Rhizoctonia solani;*
*Rhizopus* diseases, caused for example by *Rhizopus oryzae*
*Sclerotium* diseases, caused for example by *Sclerotium roffsii;*
*Septoria* diseases, caused for example by *Septoria nodorum;*
*Typhula* diseases, caused for example by *Typhula incarnata;*
*Verticillium* diseases, caused for example by *Verticillium dahliae;*
Canker, broom and dieback diseases such as:
*Nectria* diseases, caused for example by *Nectria galligena;*
Blight diseases such as:
*Monilinia* diseases, caused for example by *Monilinia laxa;*
Leaf blister or leaf curl diseases such as:
*Exobasidium* diseases caused for example by *Exobasidium vexans*
*Taphrina* diseases, caused for example by *Taphrina deformans;*
Decline diseases of wooden plants such as:
Esca diseases, caused for example by *Phaemoniella clamydospora;*
*Eutypa* dyeback, caused for example by *Eutypa lata;*
*Ganoderma* diseases caused for example by *Ganoderma boninense;*
*Rigidoporus* diseases caused for example by *Rigidoporus lignosus*
Diseases of Flowers and Seeds such as
*Botrytis* diseases caused for example by *Botrytis* cinerea;
Diseases of Tubers such as
*Rhizoctonia* diseases caused for example by *Rhizoctonia solani;*
*Helminthosporium* diseases caused for example by *Helminthosporium solani;*
Club root diseases such as
*Plasmodiophora* diseases, cause for example by *Plamodiophora brassicae.*
Diseases caused by Bacterial Organisms such as
*Xanthomonas* species for example *Xanthomonas campestris* pv. *oryzae;*
*Pseudomonas* species for example *Pseudomonas syringae* pv. *lachrymans;*
*Erwinia* species for example *Erwinia amylovora.*

The composition according to the invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds according to the invention or a composition according to the invention; this includes for example direct application, spraying, dipping, injection or any other suitable means.

The dose of active compound usually applied in the method of treatment according to the invention is generally and advantageously from 10 to 800 g/ha, preferably from 50 to 300 g/ha for applications in foliar treatment. The dose of active substance applied is generally and advantageously from 2 to 200 g per 100 kg of seed, preferably from 3 to 150 g per 100 kg of seed in the case of seed treatment.

It is clearly understood that the doses indicated herein are given as illustrative examples of the method according to the invention. A person skilled in the art will know how to adapt the application doses, notably according to the nature of the plant or crop to be treated.

The compounds or mixtures according to the invention can also be used for the preparation of composition useful to curatively or preventively treat human or animal fungal diseases such as, for example, mycoses, dermatoses, trichophyton diseases and candidiases or diseases caused by *Aspergillus* spp., for example *Aspergillus fumigatus*.

The various aspects of the invention will now be illustrated with reference to the following table of compound examples and the following preparation or efficacy examples.

Table 1 illustrates in a non-limiting manner examples of compounds of formula (I) according to the invention:

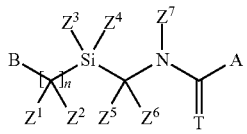

wherein A can be selected in the list consisting of the following groups: A-G1, A-G2, A-G3, A-G4, A-G5, A-G6 and A-G7:

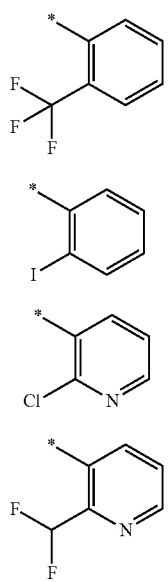

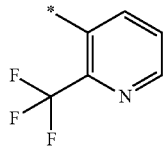

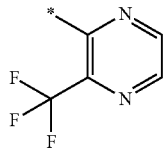

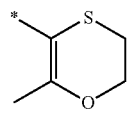

wherein * denotes the point of attachement of the group A-Gn to the (thio)carbonyl moiety.

In table 1, unless otherwise specified, M+H (Apcl+) means the molecular ion peak plus 1 a.m.u. (atomic mass unit) as observed in mass spectroscopy via positive atmospheric pressure chemical ionisation.

In table 1, the log P values were determined in accordance with EEC Directive 79/831 Annex V.A8 by HPLC (High Performance Liquid Chromatography) on a reversed-phase column (C 18), using the method described below:

Temperature: 40° C.; Mobile phases: 0.1% aqueous formic acid and acetonitrile; linear gradient from 10% acetonitrile to 90% acetonitrile.

Calibration was carried out using unbranched alkan-2-ones (comprising 3 to 16 carbon atoms) with known log P values (determination of the log P values by the retention times using linear interpolation between two successive alkanones). lambda-max-values were determined using UV-spectra from 200 nm to 400 nm and the peak values of the chromatographic signals.

Table 2 provides the NMR data ($^1$H) of a selected number of compounds from table 1

TABLE 1

| Example | A | T | n | Z1 | Z2 | Z3 | Z4 | Z5 | Z6 | Z7 | B | logP | Mass (M + H) | NMR |
|---|---|---|---|---|---|---|---|---|---|---|---|---|---|---|
| 1 | A-G4 | O | 0 | | | Me | Me | H | H | H | phenyl | 2.71 | 321 | |
| 2 | A-G5 | O | 0 | | | Me | Me | H | H | H | phenyl | 2.92 | 339 | |
| 3 | A-G3 | O | 0 | | | Me | Me | H | H | H | phenyl | 2.61 | 305 | |
| 4 | A-G3 | O | 0 | | | Me | Me | H | H | cyclopropyl | phenyl | 3.50 | 345 | |
| 5 | A-G4 | O | 0 | | | Me | Me | H | H | cyclopropyl | phenyl | 3.44 | 361 | |
| 6 | A-G7 | O | 0 | | | Me | Me | H | H | H | phenyl | 3.13 | 308 | table 2 |
| 7 | A-G6 | O | 0 | | | Me | Me | H | H | H | phenyl | 3.15 | 362 [1] | |
| 8 | A-G5 | O | 0 | | | Me | Me | H | H | cyclopropyl | phenyl | 3.89 | 379 | |
| 9 | A-G6 | O | 0 | | | Me | Me | H | H | cyclopropyl | phenyl | 4.13 | 402 [1] | |
| 10 | A-G6 | O | 0 | | | Me | Me | H | H | cyclopropyl | 2-methylphenyl | 4.41 | 416 [1] | |
| 11 | A-G5 | O | 0 | | | Me | Me | H | H | cyclopropyl | 2-methylphenyl | 4.18 | 393 | |
| 12 | A-G4 | O | 0 | | | Me | Me | H | H | cyclopropyl | 2-methylphenyl | 3.73 | 375 | |
| 13 | A-G3 | O | 0 | | | Me | Me | H | H | cyclopropyl | 2-methylphenyl | 3.80 | 359 | |
| 14 | A-G6 | O | 0 | | | Me | Me | H | H | cyclopropyl | 2-fluorophenyl | 4.18 | 420 [1] | |
| 15 | A-G5 | O | 0 | | | Me | Me | H | H | cyclopropyl | 2-fluorophenyl | 3.96 | 397 | |
| 16 | A-G4 | O | 0 | | | Me | Me | H | H | cyclopropyl | 2-fluorophenyl | 3.51 | 379 | |
| 17 | A-G3 | O | 0 | | | Me | Me | H | H | cyclopropyl | 2-fluorophenyl | 3.58 | 363 | |
| 18 | A-G3 | O | 0 | | | Me | Me | H | H | cyclopropyl | 2-ethylphenyl | 4.16 | 373 | |
| 19 | A-G4 | O | 0 | | | Me | Me | H | H | cyclopropyl | 2-ethylphenyl | 4.06 | 389 | |
| 20 | A-G5 | O | 0 | | | Me | Me | H | H | cyclopropyl | 2-ethylphenyl | 4.51 | 407 | |

TABLE 1-continued

| Example | A | T | n | Z1 | Z2 | Z3 | Z4 | Z5 | Z6 | Z7 | B | logP | Mass (M + H) | NMR |
|---|---|---|---|---|---|---|---|---|---|---|---|---|---|---|
| 21 | A-G6 | O | 0 | | | Me | Me | H | H | cyclopropyl | 2-ethylphenyl | 4.77 | 430 [1] | |
| 22 | A-G4 | O | 0 | | | Me | Me | H | H | H | 2-chlorophenyl | 3.06 | 355 | |
| 23 | A-G3 | O | 0 | | | Me | Me | H | H | cyclopropyl | 2-chlorophenyl | 3.94 | 379 | table 2 |
| 24 | A-G2 | O | 0 | | | Me | Me | H | H | cyclopropyl | 2-chlorophenyl | 5.14 | 470 | table 2 |
| 25 | A-G1 | O | 0 | | | Me | Me | H | H | cyclopropyl | 2-chlorophenyl | 5.03 | 412 | table 2 |
| 26 | A-G6 | O | 0 | | | Me | Me | H | H | cyclopropyl | 2-chlorophenyl | 4.56 | (2) | table 2 |
| 27 | A-G5 | O | 0 | | | Me | Me | H | H | cyclopropyl | 2-chlorophenyl | 4.31 | (2) | table 2 |
| 28 | A-G4 | O | 0 | | | Me | Me | H | H | cyclopropyl | 2-chlorophenyl | 3.83 | 395 | table 2 |
| 29 | A-G4 | O | 0 | | | Me | Me | H | H | H | 3-chlorophenyl | 3.15 | 355 | |
| 30 | A-G2 | O | 0 | | | Me | Me | H | H | cyclopropyl | 3-chlorophenyl | 5.14 | 470 | table 2 |
| 31 | A-G1 | O | 0 | | | Me | Me | H | H | cyclopropyl | 3-chlorophenyl | 5.03 | 412 | table 2 |
| 32 | A-G6 | O | 0 | | | Me | Me | H | H | cyclopropyl | 3-chlorophenyl | 4.56 | (2) | table 2 |
| 33 | A-G5 | O | 0 | | | Me | Me | H | H | cyclopropyl | 3-chlorophenyl | 4.34 | (2) | table 2 |
| 34 | A-G4 | O | 0 | | | Me | Me | H | H | cyclopropyl | 3-chlorophenyl | 3.87 | 395 | table 2 |
| 35 | A-G3 | O | 0 | | | Me | Me | H | H | cyclopropyl | 3-chlorophenyl | 3.96 | (2) | table 2 |
| 36 | A-G4 | O | 0 | | | Me | Et | H | H | cyclopropyl | 2-chlorophenyl | 4.21 | 409 | |
| 37 | A-G5 | O | 0 | | | Me | Et | H | H | cyclopropyl | 2-chlorophenyl | 4.71 | 427 | |
| 38 | A-G3 | O | 0 | | | Me | Et | H | H | cyclopropyl | 2-chlorophenyl | 4.34 | 393 | |
| 39 | A-G5 | O | 0 | | | Me | Me | H | H | H | 2-chlorophenyl | 3.25 | 373 | |
| 40 | A-G3 | O | 0 | | | Me | Me | H | H | H | 2-chlorophenyl | 2.94 | 339 | |
| 41 | A-G6 | O | 0 | | | Me | Me | H | H | H | 2-chlorophenyl | 3.50 | 374 | |
| 42 | A-G7 | O | 0 | | | Me | Me | H | H | H | 2-chlorophenyl | 3.50 | 342 | |
| 43 | A-G7 | O | 0 | | | Me | Me | H | H | cyclopropyl | 2-chlorophenyl | 4.29 | 382 | table 2 |
| 44 | A-G6 | O | 0 | | | Me | Et | H | H | cyclopropyl | 2-chlorophenyl | 4.95 | 428 | |
| 45 | A-G4 | O | 0 | | | Me | Me | H | H | cyclopropyl | 2-chloro-4-fluorophenyl | 3.96 | 413 | |
| 46 | A-G3 | O | 0 | | | Me | Me | H | H | cyclopropyl | 2-chloro-4-fluorophenyl | 4.06 | 397 | |
| 47 | A-G5 | O | 0 | | | Me | Me | H | H | cyclopropyl | 2-chloro-4-fluorophenyl | 4.41 | 431 | |
| 48 | A-G5 | O | 0 | | | Me | Me | H | H | cyclopropyl | 2-chloro-5-fluorophenyl | 4.34 | 431 | |
| 49 | A-G6 | O | 0 | | | Me | Me | H | H | cyclopropyl | 2-chloro-5-fluorophenyl | 4.59 | 432 | |
| 50 | A-G3 | O | 0 | | | Me | Me | H | H | cyclopropyl | 2-chloro-5-fluorophenyl | 3.99 | 397 | |
| 51 | A-G4 | O | 0 | | | Me | Me | H | H | cyclopropyl | 2-chloro-5-fluorophenyl | 3.89 | 413 | |
| 52 | A-G6 | O | 0 | | | Me | Me | H | H | cyclopropyl | 2-chloro-4-fluorophenyl | 4.67 | 432 | |
| 53 | A-G3 | O | 0 | | | Me | Me | H | H | cyclopropyl | 2-(trifluoromethyl)phenyl | 4.04 | 413 | |
| 54 | A-G6 | O | 0 | | | Me | Me | H | H | cyclopropyl | 2-(trifluoromethyl)phenyl | 4.61 | 448 | |
| 55 | A-G5 | O | 0 | | | Me | Me | H | H | cyclopropyl | 2-(trifluoromethyl)phenyl | 4.39 | 447 | |
| 56 | A-G4 | O | 0 | | | Me | Me | H | H | cyclopropyl | 2-(trifluoromethyl)phenyl | 3.94 | 429 | |
| 57 | A-G4 | O | 0 | | | Me | Me | H | H | H | 2,4-dichlorophenyl | 3.64 | 389 | |
| 58 | A-G6 | O | 0 | | | Me | Me | H | H | cyclopropyl | 2,4-dichlorophenyl | 5.25 | 448 | table 2 |
| 59 | A-G3 | O | 0 | | | Me | Me | H | H | cyclopropyl | 2,4-dichlorophenyl | 4.64 | 413 | table 2 |
| 60 | A-G2 | O | 0 | | | Me | Me | H | H | cyclopropyl | 2,4-dichlorophenyl | 5.88 | 504 | table 2 |
| 61 | A-G1 | O | 0 | | | Me | Me | H | H | cyclopropyl | 2,4-dichlorophenyl | 5.72 | 446 | table 2 |
| 62 | A-G4 | O | 0 | | | Me | Me | H | H | cyclopropyl | 2,4-dichlorophenyl | 4.51 | 429 | table 2 |
| 63 | A-G4 | O | 0 | | | Me | Me | H | H | H | 3,5-dichlorophenyl | 3.69 | 389 | |
| 64 | A-G6 | O | 0 | | | Me | Me | H | H | cyclopropyl | 3,5-dichlorophenyl | 4.95 | 448 | |
| 65 | A-G3 | O | 0 | | | Me | Me | H | H | cyclopropyl | 3,5-dichlorophenyl | 4.61 | 413 | table 2 |
| 66 | A-G1 | O | 0 | | | Me | Me | H | H | cyclopropyl | 3,5-dichlorophenyl | 5.65 | 446 | table 2 |
| 67 | A-G5 | O | 0 | | | Me | Me | H | H | cyclopropyl | 3,5-dichlorophenyl | 4.95 | 447 | table 2 |
| 68 | A-G4 | O | 0 | | | Me | Me | H | H | cyclopropyl | 3,5-dichlorophenyl | 4.49 | 429 | table 2 |
| 69 | A-G3 | O | 0 | | | Me | Me | H | H | cyclopropyl | 1-naphthyl | 4.15 | 395 | table 2 |
| 70 | A-G2 | O | 0 | | | Me | Me | H | H | cyclopropyl | 1-naphthyl | 5.31 | 486 | table 2 |
| 71 | A-G1 | O | 0 | | | Me | Me | H | H | cyclopropyl | 1-naphthyl | 5.19 | 428 | table 2 |
| 72 | A-G6 | O | 0 | | | Me | Me | H | H | cyclopropyl | 1-naphthyl | 4.77 | (2) | table 2 |
| 73 | A-G5 | O | 0 | | | Me | Me | H | H | cyclopropyl | 1-naphthyl | 4.51 | (2) | table 2 |
| 74 | A-G4 | O | 0 | | | Me | Me | H | H | cyclopropyl | 1-naphthyl | 4.04 | 411 | table 2 |
| 75 | A-G3 | O | 0 | | | Me | Me | H | H | cyclopropyl | 2-naphthyl | 4.23 | 395 | table 2 |
| 76 | A-G2 | O | 0 | | | Me | Me | H | H | cyclopropyl | 2-naphthyl | 5.36 | 486 | table 2 |
| 77 | A-G6 | O | 0 | | | Me | Me | H | H | cyclopropyl | 2-naphthyl | 4.80 | (2) | table 2 |
| 78 | A-G5 | O | 0 | | | Me | Me | H | H | cyclopropyl | 2-naphthyl | 4.56 | (2) | table 2 |
| 79 | A-G4 | O | 0 | | | Me | Me | H | H | cyclopropyl | 2-naphthyl | 4.11 | 411 | table 2 |
| 80 | A-G1 | O | 0 | | | Me | Me | H | H | cyclopropyl | 2-naphthyl | 5.25 | (2) | table 2 |
| 81 | A-G5 | O | 0 | | | Me | Me | H | H | cyclopropyl | 2-thienyl | 3.80 | 385 | table 2 |
| 82 | A-G6 | O | 0 | | | Me | Me | H | H | cyclopropyl | 2-thienyl | 4.01 | (2) | table 2 |
| 83 | A-G3 | O | 0 | | | Me | Me | H | H | cyclopropyl | 2-thienyl | 3.39 | (2) | table 2 |
| 84 | A-G2 | O | 0 | | | Me | Me | H | H | cyclopropyl | 2-thienyl | 4.59 | (2) | table 2 |
| 85 | A-G1 | O | 0 | | | Me | Me | H | H | cyclopropyl | 2-thienyl | 4.51 | (2) | table 2 |

TABLE 1-continued

| Example | A | T | n | Z1 | Z2 | Z3 | Z4 | Z5 | Z6 | Z7 | B | logP | Mass (M + H) | NMR |
|---|---|---|---|---|---|---|---|---|---|---|---|---|---|---|
| 86 | A-G6 | O | 0 | | | Me | Me | H | H | cyclopropyl | 3-thienyl | 3.94 | 386 | table 2 |
| 87 | A-G4 | O | 0 | | | Me | Me | H | H | cyclopropyl | 3-thienyl | 3.27 | 367 | table 2 |
| 88 | A-G3 | O | 0 | | | Me | Me | H | H | cyclopropyl | 3-thienyl | 3.33 | 351 | table 2 |
| 89 | A-G2 | O | 0 | | | Me | Me | H | H | cyclopropyl | 3-thienyl | 4.49 | 442 | table 2 |
| 90 | A-G1 | O | 0 | | | Me | Me | H | H | cyclopropyl | 3-thienyl | 4.44 | 384 | table 2 |
| 91 | A-G5 | O | 0 | | | Me | Me | H | H | cyclopropyl | 3-thienyl | 3.72 | (2) | table 2 |
| 92 | A-G4 | O | 1 | H | H | Me | Me | H | H | cyclopropyl | phenyl | 3.80 | 375 | table 2 |
| 93 | A-G6 | O | 1 | H | H | Me | Me | H | H | cyclopropyl | phenyl | 4.44 | 394 | table 2 |
| 94 | A-G3 | O | 1 | H | H | Me | Me | H | H | cyclopropyl | phenyl | 3.87 | 359 | table 2 |
| 95 | A-G2 | O | 1 | H | H | Me | Me | H | H | cyclopropyl | phenyl | 5.00 | 450 | table 2 |
| 96 | A-G1 | O | 1 | H | H | Me | Me | H | H | cyclopropyl | phenyl | 4.90 | 392 | table 2 |
| 97 | A-G5 | O | 1 | H | H | Me | Me | H | H | cyclopropyl | phenyl | 4.19 | 393 | table 2 |
| 98 | A-G4 | O | 1 | H | H | Me | Me | H | H | cyclopropyl | 2-chlorophenyl | 4.11 | 409 | table 2 |
| 99 | A-G6 | O | 1 | H | H | Me | Me | H | H | cyclopropyl | 2-chlorophenyl | 4.82 | 428 | table 2 |
| 100 | A-G3 | O | 1 | H | H | Me | Me | H | H | cyclopropyl | 2-chlorophenyl | 4.25 | 393 | table 2 |
| 101 | A-G2 | O | 1 | H | H | Me | Me | H | H | cyclopropyl | 2-chlorophenyl | 5.45 | 484 | table 2 |
| 102 | A-G1 | O | 1 | H | H | Me | Me | H | H | cyclopropyl | 2-chlorophenyl | 5.31 | 426 | table 2 |
| 103 | A-G5 | O | 1 | H | H | Me | Me | H | H | cyclopropyl | 2-chlorophenyl | 4.59 | 427 | table 2 |
| 104 | A-G4 | O | 1 | H | H | Me | Me | H | H | cyclopropyl | 3-chlorophenyl | 4.16 | 409 | table 2 |
| 105 | A-G6 | O | 1 | H | H | Me | Me | H | H | cyclopropyl | 3-chlorophenyl | 4.82 | 428 | table 2 |
| 106 | A-G3 | O | 1 | H | H | Me | Me | H | H | cyclopropyl | 3-chlorophenyl | 4.30 | 393 | table 2 |
| 107 | A-G2 | O | 1 | H | H | Me | Me | H | H | cyclopropyl | 3-chlorophenyl | 5.45 | 484 | table 2 |
| 108 | A-G1 | O | 1 | H | H | Me | Me | H | H | cyclopropyl | 3-chlorophenyl | 5.31 | 426 | table 2 |
| 109 | A-G5 | O | 1 | H | H | Me | Me | H | H | cyclopropyl | 3-chlorophenyl | 4.61 | 427 | table 2 |
| 110 | A-G4 | O | 1 | H | H | Me | Me | H | H | cyclopropyl | 2,4-dichlorophenyl | 4.74 | 443 | table 2 |
| 111 | A-G6 | O | 1 | H | H | Me | Me | H | H | cyclopropyl | 2,4-dichlorophenyl | 5.45 | 462 | table 2 |
| 112 | A-G3 | O | 1 | H | H | Me | Me | H | H | cyclopropyl | 2,4-dichlorophenyl | 4.90 | 427 | table 2 |
| 113 | A-G2 | O | 1 | H | H | Me | Me | H | H | cyclopropyl | 2,4-dichlorophenyl | 6.14 | 518 | table 2 |
| 114 | A-G1 | O | 1 | H | H | Me | Me | H | H | cyclopropyl | 2,4-dichlorophenyl | 5.94 | 460 | table 2 |
| 115 | A-G5 | O | 1 | H | H | Me | Me | H | H | cyclopropyl | 2,4-dichlorophenyl | 5.22 | 461 | table 2 |
| 116 | A-G6 | O | 1 | H | H | Me | Me | H | H | cyclopropyl | 3,5-dichlorophenyl | 5.45 | 462 | table 2 |
| 117 | A-G4 | O | 1 | H | H | Me | Me | H | H | cyclopropyl | 3,5-dichlorophenyl | 4.77 | 443 | table 2 |
| 118 | A-G3 | O | 1 | H | H | Me | Me | H | H | cyclopropyl | 3,5-dichlorophenyl | 4.92 | 427 | table 2 |
| 119 | A-G2 | O | 1 | H | H | Me | Me | H | H | cyclopropyl | 3,5-dichlorophenyl | 6.14 | 518 | table 2 |
| 120 | A-G1 | O | 1 | H | H | Me | Me | H | H | cyclopropyl | 3,5-dichlorophenyl | 5.94 | 460 | table 2 |
| 121 | A-G5 | O | 1 | H | H | Me | Me | H | H | cyclopropyl | 3,5-dichlorophenyl | 5.22 | 461 | table 2 |
| 122 | A-G4 | O | 0 | | | Me | Me | H | H | methyl | 3,5-dichlorophenyl | 403 | 3.92 | |
| 123 | A-G4 | S | 0 | | | Me | Me | H | H | H | 2-chlorophenyl | 371 | 3.83 | |
| 124 | A-G4 | S | 0 | | | Me | Me | H | H | cyclopropyl | 2,4-dichlorophenyl | 445 | 5.13 | |
| 125 | A-G4 | S | 0 | | | Me | Me | H | H | cyclopropyl | 2-naphthyl | 427 | 4.72 | |
| 126 | A-G6 | S | 0 | | | Me | Me | H | H | cyclopropyl | 2-naphthyl | 446 | 5.35 | |
| 127 | A-G4 | S | 1 | H | H | Me | Me | H | H | cyclopropyl | 2-chlorophenyl | 425 | 4.76 | |

Note
(1) M + Na ion
Note
(2): loss of aryl; fragment [Si(Me)$_2$CH$_2$N(cPr)C(=O)A]
Note:
Me: methyl; Et: ethyl

TABLE 2

NMR peak lists
The $^1$H-NMR data (at 400 Mhz in DMSO-d$_6$) of selected examples are stated in the form of $^1$H-NMR peak lists.
For each signal peak, the δ value in ppm and the signal intensity in brackets are listed:

| Example | $^1$H-NMR (400 Mhz in DMSO-d$_6$) |
|---|---|
| 6 | 7.6222 (0.43); 7.5496 (0.90); 7.5449 (1.18); 7.5385 (0.68); 7.5327 (0.90); 7.5259 (1.24); 7.3855 (0.38); 7.3765 (1.82); 7.3734 (1.84); 7.3671 (0.68); 7.3612 (0.89); 7.3588 (1.02); 4.2149 (1.03); 4.2067 (0.80); 4.2037 (1.09); 4.2004 (0.79); 4.1923 (1.06); 3.3460 (13.28); 2.9830 (1.06); 2.9748 (0.78); 2.9717 (1.10); 2.9604 (1.01); 2.8651 (1.95); 2.8507 (1.94); 2.5166 (2.47); 2.5122 (5.04); 2.5078 (6.77); 2.5033 (4.82); 2.4990 (2.24); 1.8778 (7.97); 0.2935 (0.78); 0.2854 (16.00); 0.2771 (0.71) |
| 23 | 8.4477 (0.90); 8.4429 (0.97); 8.4357 (0.93); 8.4309 (0.92); 7.7708 (0.84); 7.7661 (0.87); 7.7519 (1.00); 7.7471 (0.96); 7.5733 (0.87); 7.5556 (0.91); 7.4954 (1.02); 7.4834 (0.98); 7.4764 (0.94); 7.4644 (0.90); 7.4486 (1.83); 7.4398 (2.19); 7.4361 (1.14); 7.3822 (0.63); 7.3717 (0.70); 7.3638 (0.59); 7.3612 (0.49); 7.3553 (0.52); 7.3514 (0.44); 7.3426 (0.34); 3.3903 (0.52); 3.3721 (0.77); 3.3371 (66.23); 2.6028 (0.32); 2.5953 (0.38); 2.5860 (0.62); 2.5761 (0.42); 2.5684 (0.35); 2.5252 (0.44); 2.5116 (7.50); 2.5074 (14.80); 2.5029 (19.60); 2.4984 (14.69); 2.4944 (7.46); 1.2309 (0.42); 0.5093 (16.00); 0.4637 (0.70); 0.4533 (0.85); 0.4455 (1.04); 0.3840 (0.86); 0.3742 (0.73); 0.3667 (0.85); 0.3570 (0.65); 0.1189 (0.89); −0.0002 (0.97) |
| 24 | 7.8593 (1.09); 7.8409 (1.07); 7.5830 (0.95); 7.5658 (0.90); 7.5638 (0.87); 7.4486 (1.91); 7.4461 (2.03); 7.4388 (1.73); 7.4364 (1.57); 7.4322 (1.27); 7.4276 (0.70); 7.4161 (0.43); 7.4112 (1.27); 7.4086 (1.17); 7.3922 (0.76); 7.3900 (0.75); 7.3795 (0.73); 7.3709 (0.59); 7.3667 (0.53); 7.3612 (0.73); 7.3583 (0.59); 7.3538 (0.62); 7.3474 (0.49); 7.3400 (0.42); 7.1380 (0.49); 7.1340 (0.67); 7.1190 (0.73); 7.1147 (1.31); 7.1099 (1.25); 7.0997 (0.42); 7.0956 (0.77); 7.0912 (1.11); 3.3713 (0.36); 3.3529 (0.57); 3.3306 (58.18); |

TABLE 2-continued

NMR peak lists
The ¹H-NMR data (at 400 Mhz in DMSO-d₆) of selected examples are stated in the form of ¹H-NMR peak lists.
For each signal peak, the δ value in ppm and the signal intensity in brackets are listed:

| Example | ¹H-NMR (400 Mhz in DMSO-d₆) |
|---|---|
| | 2.5997 (0.38); 2.5918 (0.44); 2.5824 (0.68); 2.5729 (0.47); 2.5649 (0.37); 2.5245 (0.47); 2.5110 (8.87); 2.5067 (17.50); 2.5021 (23.09); 2.4976 (17.19); 2.4933 (8.61); 1.2302 (0.50); 0.5197 (16.00); 0.4631 (1.32); 0.4566 (1.21); 0.4541 (1.21); 0.4456 (1.18); 0.4203 (0.40); 0.3558 (0.60); 0.3408 (0.84); 0.3320 (0.63); 0.3202 (0.49); 0.1290 (0.94); −0.0002 (1.66) |
| 25 | 7.7876 (1.07); 7.7681 (1.31); 7.6986 (0.50); 7.6805 (1.12); 7.6619 (0.80); 7.6256 (0.89); 7.6064 (1.10); 7.5871 (0.50); 7.5785 (1.35); 7.5612 (1.19); 7.5593 (1.16); 7.4559 (2.51); 7.4534 (2.63); 7.4454 (2.20); 7.4399 (1.46); 7.4236 (0.39); 7.4200 (0.40); 7.3856 (0.92); 7.3767 (0.76); 7.3731 (0.70); 7.3673 (0.89); 7.3644 (0.66); 7.3597 (0.66); 7.3538 (0.61); 7.3462 (0.61); 7.3217 (1.21); 7.3029 (1.06); 5.2982 (0.34); 3.3896 (0.36); 3.3718 (0.74); 3.3378 (121.27); 2.5618 (0.44); 2.5561 (0.53); 2.5460 (0.84); 2.5254 (0.93); 2.5118 (13.36); 2.5074 (26.19); 2.5028 (34.54); 2.4983 (25.58); 2.4940 (12.67); 1.2307 (0.69); 0.4999 (16.00); 0.4592 (1.02); 0.4456 (1.56); 0.4411 (0.54); 0.4318 (0.33); 0.4159 (0.37); 0.4096 (0.38); 0.4008 (0.58); 0.3900 (0.37); 0.3760 (0.36); 0.3645 (0.39); 0.3563 (0.59); 0.3475 (0.42); 0.3410 (0.51); 0.3319 (0.35); 0.3240 (0.36); 0.3052 (0.48); 0.3015 (0.54); 0.2420 (0.35); 0.1099 (1.03); −0.0002 (3.64) |
| 26 | 9.0491 (1.20); 9.0434 (1.35); 8.9566 (1.34); 8.9509 (1.22); 7.5668 (0.87); 7.5491 (0.89); 7.4574 (1.79); 7.4556 (1.75); 7.4479 (1.65); 7.4420 (1.00); 7.3890 (0.59); 7.3800 (0.50); 7.3766 (0.44); 7.3705 (0.58); 7.3631 (0.42); 7.3570 (0.41); 3.4348 (1.48); 3.3351 (54.80); 2.5831 (0.35); 2.5736 (0.60); 2.5630 (0.39); 2.5561 (0.36); 2.5075 (12.96); 2.5032 (17.01); 2.4988 (12.98); 0.5129 (0.97); 0.5044 (16.00); 0.4797 (0.65); 0.4417 (0.49); 0.3992 (1.00); 0.3742 (1.13); 0.3631 (0.81); 0.3565 (0.98) |
| 27 | 8.7910 (0.89); 8.7804 (0.90); 7.8706 (0.74); 7.8512 (1.03); 7.7707 (0.87); 7.7591 (0.86); 7.7510 (0.64); 7.7393 (0.62); 7.5773 (0.96); 7.5592 (1.00); 7.4559 (2.06); 7.4468 (2.10); 7.4427 (1.18); 7.3874 (0.65); 7.3778 (0.57); 7.3759 (0.54); 7.3689 (0.63); 7.3611 (0.48); 7.3558 (0.49); 7.3478 (0.35); 3.3325 (53.29); 2.5683 (0.39); 2.5567 (0.63); 2.5431 (0.44); 2.5250 (0.44); 2.5112 (7.23); 2.5071 (14.19); 2.5027 (18.85); 2.4983 (14.39); 0.5004 (16.00); 0.4155 (0.43); 0.3894 (0.58); −0.0002 (0.38); −0.0490 (0.50) |
| 28 | 8.7275 (0.70); 8.7241 (0.75); 8.7156 (0.78); 8.7123 (0.78); 7.8113 (0.64); 7.7915 (0.77); 7.6121 (0.55); 7.6005 (0.57); 7.5925 (0.52); 7.5804 (1.24); 7.5627 (0.83); 7.4555 (1.70); 7.4467 (1.66); 7.4422 (0.97); 7.3864 (0.55); 7.3770 (0.49); 7.3680 (0.55); 7.3602 (0.41); 7.3547 (0.37); 6.9437 (0.58); 6.8086 (1.26); 6.6736 (0.62); 3.3794 (2.14); 3.3300 (183.46); 3.3015 (0.49); 2.6710 (0.59); 2.6666 (0.42); 2.6610 (0.41); 2.6539 (0.36); 2.6437 (0.59); 2.6330 (0.37); 2.6284 (0.37); 2.5240 (1.50); 2.5106 (26.97); 2.5063 (53.21); 2.5018 (70.51); 2.4973 (53.08); 2.4932 (27.20); 2.3286 (0.43); 1.2353 (0.56); 0.5033 (16.00); 0.3901 (1.92); 0.3724 (0.99); −0.0002 (1.49) |
| 30 | 7.8540 (0.86); 7.8520 (0.92); 7.8342 (0.93); 7.8322 (0.94); 7.6105 (1.06); 7.6055 (1.04); 7.5815 (0.49); 7.5784 (0.70); 7.5754 (0.49); 7.5643 (0.63); 7.5612 (0.84); 7.5585 (0.62); 7.4793 (0.42); 7.4741 (0.35); 7.4632 (0.92); 7.4584 (1.26); 7.4541 (0.85); 7.4466 (1.14); 7.4293 (0.97); 7.4082 (0.65); 7.4050 (0.53); 7.3887 (0.96); 7.3862 (1.00); 7.3699 (0.63); 7.3674 (0.70); 7.1298 (0.48); 7.1258 (0.55); 7.1104 (0.76); 7.1066 (0.82); 7.0914 (0.42); 7.0874 (0.44); 6.9795 (0.81); 6.9757 (0.81); 6.9605 (0.78); 6.9567 (0.72); 3.3530 (0.47); 3.3303 (49.09); 2.9756 (0.39); 2.5640 (0.37); 2.5547 (0.59); 2.5447 (0.44); 2.5370 (0.38); 2.5248 (0.47); 2.5111 (7.37); 2.5067 (14.51); 2.5021 (19.16); 2.4976 (14.31); 2.4932 (7.18); 1.2302 (0.43); 0.4553 (1.03); 0.4473 (16.00); 0.4390 (1.34); 0.3757 (0.33); 0.3466 (0.68); 0.3317 (1.58); 0.2956 (0.32); −0.0002 (1.30) |
| 31 | 7.7804 (0.83); 7.7614 (1.02); 7.6741 (0.34); 7.6559 (0.88); 7.6377 (0.70); 7.6161 (0.76); 7.6062 (1.38); 7.6008 (1.77); 7.5764 (1.07); 7.5592 (1.05); 7.4873 (0.46); 7.4823 (0.36); 7.4711 (0.98); 7.4668 (1.38); 7.4622 (0.88); 7.4531 (1.49); 7.4356 (1.18); 7.4158 (0.49); 7.1808 (0.93); 7.1622 (0.85); 3.3723 (0.37); 3.3345 (70.37); 2.5249 (0.79); 2.5115 (9.51); 2.5073 (17.79); 2.5028 (23.39); 2.4984 (17.65); 1.2311 (0.45); 0.4275 (16.00); 0.3906 (0.48); 0.3454 (0.44); 0.3319 (1.48); 0.3236 (0.34); 0.3174 (0.32); 0.3056 (0.47); 0.2961 (0.51); 0.2864 (0.52); 0.2761 (0.37); 0.2548 (0.35); 0.2396 (0.32); −0.0002 (1.26) |
| 32 | 9.0396 (1.15); 9.0338 (1.32); 8.9527 (1.30); 8.9468 (1.18); 7.6165 (1.14); 7.6121 (1.13); 7.5742 (0.72); 7.5572 (0.90); 7.4767 (0.40); 7.4607 (0.78); 7.4563 (1.16); 7.4518 (0.69); 7.4451 (1.27); 7.4277 (1.03); 7.4080 (0.38); 3.3301 (42.10); 3.2926 (1.57); 2.5655 (0.34); 2.5535 (0.60); 2.5382 (0.42); 2.5254 (0.49); 2.5113 (6.52); 2.5072 (12.98); 2.5027 (17.38); 2.4983 (13.28); 0.4326 (0.86); 0.4245 (16.00); 0.3930 (1.75); 0.3852 (2.03); 0.3677 (1.11); −0.0002 (0.47) |
| 33 | 8.7874 (0.62); 8.7808 (0.93); 8.7721 (0.69); 7.7407 (1.61); 7.7366 (1.67); 7.7309 (3.20); 7.6088 (1.21); 7.6040 (1.23); 7.5765 (0.79); 7.5595 (0.99); 7.4884 (0.42); 7.4723 (0.85); 7.4677 (1.19); 7.4633 (0.73); 7.4543 (1.33); 7.4367 (1.08); 7.4172 (0.44); 3.3285 (33.97); 2.5367 (0.44); 2.5214 (0.90); 2.5112 (6.82); 2.5070 (13.24); 2.5026 (17.55); 2.4981 (13.50); 0.4284 (16.00); 0.3989 (0.63); −0.0002 (0.54) |
| 34 | 8.7203 (0.76); 8.7170 (0.84); 8.7087 (0.83); 8.7053 (0.84); 7.6992 (0.64); 7.6797 (0.90); 7.6098 (1.19); 7.6053 (1.21); 7.5958 (0.71); 7.5813 (0.91); 7.5776 (1.18); 7.5614 (1.16); 7.4873 (0.42); 7.4712 (0.81); 7.4666 (1.16); 7.4623 (0.73); 7.4525 (1.21); 7.4349 (1.02); 7.4152 (0.40); 6.8843 (0.62); 6.7493 (1.35); 6.6143 (0.68); 3.3269 (24.49); 3.2492 (2.03); 2.6294 (0.46); 2.6162 (0.60); 2.6019 (0.45); 2.5109 (5.93); 2.5067 (11.90); 2.5022 (15.94); 2.4978 (12.15); 0.4333 (16.00); 0.3887 (2.54); 0.3748 (3.83); −0.0002 (0.56) |
| 35 | 8.4425 (0.81); 8.4378 (0.89); 8.4306 (0.89); 8.4258 (0.88); 7.6830 (0.78); 7.6782 (0.83); 7.6641 (0.97); 7.6593 (0.95); 7.6105 (1.16); 7.6066 (1.16); 7.5744 (0.74); 7.5572 (0.91); 7.4841 (1.13); 7.4799 (0.49); 7.4723 (1.06); 7.4641 (1.29); 7.4587 (1.21); 7.4536 (1.32); 7.4462 (1.23); 7.4288 (1.00); 7.4090 (0.39); 3.3247 (16.41); 3.2445 (0.74); 2.5794 (0.33); 2.5705 (0.64); 2.5595 (0.38); 2.5525 (0.32); 2.5065 (11.05); 2.5020 (14.64); 2.4976 (11.16); 0.4351 (16.00); 0.3851 (0.43); 0.3683 (0.81); −0.0002 (0.72) |
| 42 | 7.6761 (0.46); 7.5108 (0.53); 7.5091 (0.58); 7.5074 (0.52); 7.4944 (0.53); 7.4918 (0.91); 7.4891 (0.58); 7.4286 (0.71); 7.4243 (1.30); 7.4156 (2.04); 7.4131 (1.76); 7.3519 (0.55); 7.3435 (0.45); 7.3391 (0.42); 7.3337 (0.49); 7.3307 (0.41); 7.3239 (0.38); 7.3222 (0.40); 4.2161 (1.04); 4.2079 (0.82); 4.2048 (1.10); 4.2015 (0.82); 4.1935 (1.07); 3.3456 (27.34); 3.0009 (1.89); 2.9865 (2.15); 2.9753 (0.85); 2.9720 (1.15); 2.9691 (0.85); 2.9607 (1.04); 2.5166 (4.24); 2.5123 (8.65); 2.5078 (11.68); 2.5033 (8.36); 2.4989 (3.92); 1.8931 (8.19); 0.3822 (0.78); 0.3739 (16.00); 0.3655 (0.74) |
| 43 | 7.4614 (1.01); 7.4589 (0.80); 7.4435 (1.24); 7.4408 (1.01); 7.3825 (2.51); 7.3738 (3.06); 7.3708 (1.83); 7.3153 (0.87); 7.3046 (1.15); 7.2971 (0.79); 7.2941 (0.67); 7.2874 (0.67); 7.2857 (0.63); 7.2759 (0.46); 4.1909 (1.36); 4.1797 (1.59); 4.1765 (1.32); 4.1685 (1.52); 3.3516 (0.51); 3.3008 (38.44); 3.1675 (1.68); |

TABLE 2-continued

NMR peak lists
The $^1$H-NMR data (at 400 Mhz in DMSO-$d_6$) of selected examples are stated in the form of $^1$H-NMR peak lists.
For each signal peak, the δ value in ppm and the signal intensity in brackets are listed:

| Example | $^1$H-NMR (400 Mhz in DMSO-$d_6$) |
|---|---|
|  | 2.9567 (1.38); 2.9454 (1.57); 2.9343 (1.44); 2.6325 (0.44); 2.6279 (0.45); 2.4813 (0.46); 2.4725 (5.96); 2.4681 (12.70); 2.4636 (17.69); 2.4591 (13.34); 2.4548 (6.95); 1.6259 (12.81); 0.6455 (1.11); 0.6281 (1.66); 0.3579 (16.00) |
| 58 | 9.0434 (1.18); 9.0376 (1.31); 8.9572 (1.34); 8.9515 (1.20); 7.6217 (1.55); 7.6169 (1.67); 7.5662 (1.31); 7.5460 (1.93); 7.4737 (1.20); 7.4689 (1.14); 7.4536 (0.79); 7.4488 (0.78); 5.3030 (0.65); 3.4101 (1.53); 3.3921 (0.41); 3.3736 (0.80); 3.3554 (0.97); 3.3300 (40.04); 2.5848 (0.33); 2.5737 (0.57); 2.5575 (0.45); 2.5446 (0.37); 2.5252 (0.55); 2.5114 (10.61); 2.5073 (20.67); 2.5028 (27.24); 2.4983 (20.32); 1.2497 (0.59); 1.2316 (1.29); 1.2134 (0.55); 0.5075 (1.23); 0.4988 (16.00); 0.4772 (0.65); 0.4456 (0.72); 0.4409 (1.49); 0.3956 (1.79); 0.3769 (1.06); 0.3560 (0.54); 0.3386 (0.42); 0.2447 (0.46); −0.0002 (3.12) |
| 59 | 8.4516 (0.99); 8.4470 (1.01); 8.4396 (1.01); 8.4350 (0.96); 7.8043 (0.92); 7.7996 (0.93); 7.7854 (1.07); 7.7807 (1.00); 7.6111 (1.66); 7.6063 (1.71); 7.5745 (1.48); 7.5543 (1.90); 7.5016 (1.05); 7.4896 (1.05); 7.4827 (1.00); 7.4706 (1.13); 7.4662 (1.36); 7.4615 (1.18); 7.4461 (0.89); 7.4414 (0.84); 3.3903 (0.38); 3.3726 (0.74); 3.3350 (63.44); 2.9982 (0.39); 2.6159 (0.36); 2.6087 (0.42); 2.5998 (0.70); 2.5897 (0.46); 2.5818 (0.38); 2.5076 (16.46); 2.5033 (21.14); 2.4989 (15.98); 1.2317 (0.52); 0.5022 (16.00); 0.4662 (0.86); 0.4491 (0.73); 0.4414 (2.02); 0.4012 (1.10); 0.3845 (1.02); 0.3563 (0.34); 0.2524 (0.67); −0.0002 (0.34) |
| 60 | 7.8626 (1.03); 7.8603 (1.06); 7.8416 (1.22); 7.6083 (1.71); 7.6036 (1.83); 7.5862 (1.52); 7.5661 (2.06); 7.4596 (1.23); 7.4547 (1.21); 7.4392 (1.20); 7.4348 (1.46); 7.4183 (1.22); 7.3995 (0.70); 7.3976 (0.65); 7.1395 (1.01); 7.1358 (1.32); 7.1319 (1.11); 7.1210 (1.21); 7.1172 (1.34); 7.1128 (0.96); 7.1044 (0.67); 7.1006 (0.43); 3.3538 (0.36); 3.3275 (30.71); 2.9762 (0.33); 2.6149 (0.39); 2.6071 (0.49); 2.5978 (0.73); 2.5884 (0.49); 2.5802 (0.39); 2.5249 (0.40); 2.5071 (13.87); 2.5026 (18.18); 2.4982 (13.60); 1.2314 (0.40); 0.5126 (16.00); 0.4669 (1.41); 0.4595 (1.33); 0.4409 (2.09); 0.4157 (0.39); 0.3563 (0.98); 0.3505 (0.80); 0.3392 (0.66); 0.2733 (0.40); −0.0002 (1.50) |
| 61 | 7.7897 (1.04); 7.7705 (1.30); 7.7080 (0.46); 7.6901 (1.11); 7.6715 (0.78); 7.6317 (0.82); 7.6165 (2.71); 7.6118 (3.27); 7.5938 (0.51); 7.5772 (1.88); 7.5711 (0.33); 7.5571 (2.52); 7.4672 (1.66); 7.4623 (1.53); 7.4471 (1.18); 7.4422 (1.10); 7.3586 (1.18); 7.3396 (1.04); 3.3722 (0.35); 3.3539 (0.43); 3.3481 (0.36); 3.3272 (57.54); 2.5759 (0.45); 2.5657 (0.72); 2.5526 (0.51); 2.5377 (0.34); 2.5247 (0.70); 2.5113 (12.34); 2.5069 (24.59); 2.5024 (32.72); 2.4979 (24.45); 2.4935 (12.29); 1.2309 (0.61); 0.4915 (16.00); 0.4618 (0.54); 0.4491 (0.58); 0.4407 (2.09); 0.4325 (0.49); 0.4058 (0.34); 0.3954 (0.46); 0.3764 (0.34); 0.3724 (0.35); 0.3646 (0.35); 0.3559 (0.66); 0.3510 (0.42); 0.3386 (0.62); 0.3320 (0.40); 0.3140 (0.39); 0.3038 (0.55); 0.2394 (0.59); −0.0002 (2.77) |
| 62 | 8.7332 (0.80); 8.7301 (0.86); 8.7215 (0.87); 8.7183 (0.86); 7.8587 (0.73); 7.8392 (0.85); 7.6194 (1.79); 7.6144 (1.96); 7.6035 (0.59); 7.5915 (0.56); 7.5807 (1.29); 7.5606 (1.79); 7.4692 (1.09); 7.4644 (1.06); 7.4491 (0.80); 7.4442 (0.77); 6.9483 (0.64); 6.8132 (1.39); 6.6780 (0.70); 3.3518 (2.59); 3.3307 (50.72); 2.6768 (0.45); 2.6714 (0.43); 2.6647 (0.65); 2.6505 (0.42); 2.5251 (0.39); 2.5114 (7.70); 2.5071 (15.27); 2.5026 (20.25); 2.4981 (15.23); 2.4941 (7.82); 0.4958 (16.00); 0.4041 (3.30); 0.3886 (1.68); −0.0002 (0.39) |
| 65 | 8.4499 (0.87); 8.4451 (0.92); 8.4379 (0.92); 8.4331 (0.89); 7.7567 (0.83); 7.7519 (0.85); 7.7378 (0.99); 7.7330 (0.95); 7.6369 (0.71); 7.6321 (1.56); 7.6273 (1.10); 7.5916 (3.83); 7.5867 (3.16); 7.4982 (1.03); 7.4862 (0.97); 7.4793 (0.88); 7.4673 (0.84); 3.3281 (36.81); 3.2351 (0.40); 2.5987 (0.60); 2.5880 (0.36); 2.5249 (0.38); 2.5115 (7.25); 2.5071 (14.18); 2.5026 (18.66); 2.4981 (13.79); 2.4938 (6.84); 1.2312 (0.38); 0.4496 (1.30); 0.4415 (16.00); 0.4040 (0.90); 0.3867 (0.84); 0.3768 (0.54); 0.3643 (1.36); −0.0002 (1.32) |
| 66 | 7.7870 (0.81); 7.7678 (1.00); 7.6981 (0.35); 7.6798 (0.87); 7.6612 (0.65); 7.6406 (0.91); 7.6357 (1.84); 7.6308 (1.60); 7.6091 (0.84); 7.5853 (4.25); 7.5804 (3.53); 7.2838 (0.90); 7.2651 (0.81); 3.3540 (0.33); 3.3250 (29.71); 2.5673 (0.32); 2.5616 (0.37); 2.5515 (0.62); 2.5389 (0.47); 2.5112 (9.41); 2.5068 (18.44); 2.5023 (24.27); 2.4978 (17.92); 2.4935 (8.88); 1.2309 (0.45); 0.4325 (16.00); 0.3904 (0.42); 0.3717 (0.61); 0.3642 (1.69); 0.3458 (0.46); 0.3371 (0.36); 0.3279 (0.55); 0.3047 (0.37); 0.2999 (0.49); 0.2688 (0.34); −0.0002 (2.55) |
| 67 | 8.7939 (0.80); 8.7827 (0.83); 7.8583 (0.64); 7.8389 (0.97); 7.7760 (0.82); 7.7643 (0.81); 7.7562 (0.57); 7.7446 (0.54); 7.6416 (0.75); 7.6368 (1.63); 7.6320 (1.09); 7.5902 (3.93); 7.5853 (3.44); 3.3342 (62.03); 2.5728 (0.38); 2.5600 (0.59); 2.5464 (0.43); 2.5254 (0.41); 2.5117 (7.42); 2.5076 (14.82); 2.5031 (19.84); 2.4987 (15.19); 0.4336 (16.00); 0.4063 (0.72); 0.4004 (0.73); −0.0002 (0.35) |
| 68 | 8.7300 (0.80); 8.7272 (0.88); 8.7185 (0.88); 8.7155 (0.89); 7.8013 (0.74); 7.7823 (0.90); 7.6417 (0.76); 7.6369 (1.68); 7.6321 (1.20); 7.6179 (0.65); 7.6059 (0.69); 7.5926 (3.93); 7.5877 (3.77); 6.9079 (0.64); 6.7728 (1.37); 6.6377 (0.69); 3.3317 (54.71); 3.2345 (2.55); 2.6727 (0.60); 2.6594 (0.75); 2.6458 (0.52); 2.5071 (14.98); 2.5027 (20.21); 2.4982 (15.64); 0.4391 (16.00); 0.4044 (3.75); 0.3906 (3.65); 0.3642 (0.63); −0.0002 (0.34) |
| 69 | 8.4351 (0.93); 8.4303 (1.01); 8.4231 (1.02); 8.4183 (1.01); 8.2028 (0.87); 8.1821 (0.94); 8.0097 (0.91); 7.9873 (1.46); 7.9658 (0.93); 7.9629 (0.93); 7.7831 (0.86); 7.7805 (0.89); 7.7661 (1.07); 7.7635 (1.00); 7.6301 (1.09); 7.6255 (1.28); 7.6114 (1.80); 7.6069 (1.63); 7.5913 (0.67); 7.5874 (0.60); 7.5719 (0.69); 7.5691 (0.74); 7.5528 (1.65); 7.5355 (1.27); 7.5329 (1.36); 7.5158 (0.81); 7.4635 (1.10); 7.4515 (1.10); 7.4446 (0.93); 7.4326 (0.93); 3.4824 (1.26); 3.3775 (0.32); 3.3441 (66.02); 2.8967 (0.52); 2.7381 (0.43); 2.5315 (0.50); 2.5178 (7.90); 2.5136 (15.20); 2.5090 (20.07); 2.5045 (15.03); 2.5002 (7.70); 1.2369 (0.36); 0.6246 (16.00); 0.4274 (1.08); 0.2758 (0.54) |
| 70 | 8.1833 (0.88); 8.1626 (0.93); 8.0013 (0.92); 7.9802 (1.73); 7.9594 (0.93); 7.9570 (0.92); 7.8446 (1.07); 7.8251 (1.10); 7.7851 (0.84); 7.7829 (0.89); 7.7682 (1.02); 7.7662 (0.98); 7.6222 (0.34); 7.6190 (0.39); 7.6052 (0.68); 7.6019 (0.82); 7.5848 (0.63); 7.5811 (0.57); 7.5616 (0.73); 7.5467 (1.41); 7.5269 (1.36); 7.5096 (0.79); 7.3751 (0.55); 7.3563 (1.14); 7.3374 (0.65); 7.1151 (0.50); 7.1112 (0.55); 7.0957 (0.87); 7.0920 (0.90); 7.0766 (0.50); 7.0728 (0.47); 6.9377 (0.90); 6.9340 (0.91); 6.9187 (0.87); 6.9150 (0.81); 3.3290 (43.30); 2.8899 (0.56); 2.7310 (0.48); 2.5242 (0.63); 2.5105 (8.42); 2.5065 (16.18); 2.5021 (21.03); 2.4976 (16.13); 2.4935 (8.21); 2.4811 (0.66); 0.6288 (16.00); 0.5958 (0.32); 0.4206 (1.37); 0.4129 (1.26); 0.2452 (0.46); −0.0002 (1.60) |
| 71 | 8.1838 (1.25); 8.1630 (1.29); 8.0106 (1.29); 7.9872 (1.67); 7.9655 (1.29); 7.9625 (1.23); 7.7847 (1.25); 7.7820 (1.32); 7.7680 (2.18); 7.7544 (1.30); 7.7505 (1.15); 7.6346 (0.42); 7.6168 (1.52); 7.6005 (2.66); 7.5966 (2.31); 7.5827 (1.68); 7.5790 (1.78); 7.5651 (1.18); 7.5624 (1.40); 7.5539 (1.56); 7.5453 (1.41); 7.5367 (1.47); 7.5335 (1.50); 7.5285 (0.71); 7.5260 (0.63); 7.5164 (1.13); 7.1127 (1.12); 7.0953 (1.01); |

TABLE 2-continued

NMR peak lists
The $^1$H-NMR data (at 400 Mhz in DMSO-d$_6$) of selected examples are stated in the form of $^1$H-NMR peak lists.
For each signal peak, the δ value in ppm and the signal intensity in brackets are listed:

| Example | $^1$H-NMR (400 Mhz in DMSO-d$_6$) |
|---|---|
| | 3.3536 (0.37); 3.3298 (58.47); 2.5249 (0.58); 2.5115 (10.80); 2.5071 (21.35); 2.5025 (28.25); 2.4980 (20.99); 2.4936 (10.45); 2.4767 (0.57); 2.4693 (0.58); 2.4594 (0.84); 2.4493 (0.54); 2.4427 (0.46); 1.2307 (0.45); 0.6121 (16.00); 0.5828 (0.47); 0.5716 (0.45); 0.5125 (0.36); 0.4215 (0.56); 0.2550 (0.32); 0.2144 (0.39); 0.2041 (0.39); −0.0002 (1.70) |
| 72 | 9.0612 (1.26); 9.0553 (1.43); 8.9622 (1.41); 8.9563 (1.29); 8.1984 (0.88); 8.1778 (0.94); 8.0053 (0.92); 7.9836 (1.62); 7.9604 (0.91); 7.7717 (0.87); 7.7697 (0.88); 7.7549 (1.04); 7.6346 (0.35); 7.6316 (0.38); 7.6174 (0.66); 7.6143 (0.81); 7.5970 (0.60); 7.5936 (0.55); 7.5700 (0.70); 7.5514 (1.72); 7.5337 (1.27); 7.5136 (0.70); 3.5154 (0.98); 3.3369 (58.51); 2.8914 (0.32); 2.6019 (0.32); 2.5946 (0.38); 2.5852 (0.63); 2.5754 (0.43); 2.5676 (0.36); 2.5256 (0.39); 2.5121 (7.23); 2.5080 (14.09); 2.5036 (18.58); 2.4992 (14.00); 0.6115 (16.00); 0.5942 (0.66); 0.3644 (0.84); 0.2908 (0.98); 0.2814 (0.68); 0.2735 (0.97) |
| 73 | 8.7704 (0.92); 8.7599 (0.93); 8.1795 (1.01); 8.1588 (1.07); 8.0133 (1.05); 7.9923 (1.25); 7.9672 (1.04); 7.9649 (1.03); 7.7838 (0.97); 7.7816 (1.02); 7.7669 (1.17); 7.7648 (1.14); 7.7202 (0.55); 7.7087 (0.54); 7.7005 (1.03); 7.6889 (1.05); 7.6535 (1.28); 7.6360 (0.66); 7.6230 (0.40); 7.6196 (0.44); 7.6058 (0.80); 7.6026 (0.93); 7.5855 (0.73); 7.5817 (0.66); 7.5677 (0.78); 7.5654 (0.85); 7.5553 (1.13); 7.5479 (1.10); 7.5380 (1.18); 7.5351 (1.26); 7.5179 (0.87); 3.3333 (54.12); 2.5249 (0.40); 2.5074 (16.18); 2.5029 (21.45); 2.4985 (16.35); 2.4735 (0.76); 2.4622 (0.46); 0.6132 (16.00); 0.4145 (0.80); 0.3034 (0.49); −0.0003 (0.33) |
| 74 | 8.7020 (0.79); 8.6981 (0.86); 8.6906 (0.87); 8.6867 (0.85); 8.1820 (0.90); 8.1614 (0.94); 8.0129 (0.93); 7.9921 (1.09); 7.9663 (0.91); 7.9640 (0.90); 7.7844 (0.89); 7.7696 (1.03); 7.7675 (1.00); 7.6181 (0.34); 7.6149 (0.38); 7.6008 (0.72); 7.5977 (0.87); 7.5936 (0.77); 7.5808 (0.75); 7.5721 (1.24); 7.5692 (1.23); 7.5533 (1.40); 7.5375 (1.63); 7.5338 (1.34); 7.5169 (0.94); 6.9097 (0.64); 6.7746 (1.39); 6.6397 (0.70); 3.4837 (1.48); 3.3326 (47.22); 2.8904 (0.38); 2.7316 (0.33); 2.5650 (0.34); 2.5582 (0.40); 2.5492 (0.69); 2.5385 (0.49); 2.5309 (0.46); 2.5201 (0.73); 2.5112 (7.17); 2.5071 (14.20); 2.5027 (18.96); 2.4982 (14.42); 0.6156 (16.00); 0.3522 (1.20); 0.3204 (0.54); 0.3093 (1.12); 0.2924 (1.02); 0.2836 (0.63) |
| 75 | 8.4140 (0.98); 8.4093 (1.06); 8.4020 (1.07); 8.3973 (1.06); 8.1805 (1.87); 7.9698 (0.62); 7.9567 (0.66); 7.9410 (1.27); 7.9205 (1.69); 7.9138 (0.79); 7.9007 (0.86); 7.7346 (1.13); 7.7326 (1.11); 7.7144 (0.95); 7.7121 (0.94); 7.6103 (0.94); 7.6055 (0.99); 7.5914 (1.18); 7.5866 (1.13); 7.5539 (1.44); 7.5488 (1.01); 7.5423 (1.33); 7.5349 (0.98); 7.5303 (1.39); 7.4084 (1.13); 7.3964 (1.11); 7.3895 (0.98); 7.3775 (0.95); 3.3380 (62.85); 2.5800 (0.36); 2.5726 (0.41); 2.5633 (0.68); 2.5532 (0.47); 2.5456 (0.41); 2.5256 (0.43); 2.5121 (7.25); 2.5078 (14.26); 2.5033 (18.87); 2.4988 (14.09); 2.4945 (7.09); 0.5196 (16.00); 0.4484 (0.69); 0.4231 (0.41); 0.4147 (1.43); 0.3776 (0.37); 0.3535 (0.79); 0.3372 (0.79); 0.3286 (0.87) |
| 76 | 8.1950 (2.43); 7.9787 (0.87); 7.9658 (0.91); 7.9550 (0.96); 7.9422 (1.55); 7.9215 (2.21); 7.9002 (1.23); 7.8865 (0.32); 7.8351 (1.43); 7.8336 (1.49); 7.8155 (1.52); 7.8138 (1.53); 7.7427 (1.48); 7.7408 (1.49); 7.7225 (1.24); 7.7203 (1.26); 7.5652 (0.37); 7.5533 (1.98); 7.5482 (1.37); 7.5423 (1.73); 7.5406 (1.70); 7.5346 (1.39); 7.5299 (1.94); 7.5179 (0.44); 7.2974 (0.70); 7.2951 (0.71); 7.2786 (1.53); 7.2763 (1.53); 7.2599 (0.93); 7.2575 (0.91); 7.0936 (0.75); 7.0897 (0.81); 7.0742 (1.18); 7.0705 (1.23); 7.0552 (0.63); 7.0513 (0.63); 6.8952 (1.29); 6.8914 (1.32); 6.8762 (1.23); 6.8724 (1.18); 3.3724 (0.35); 3.3530 (6.40); 2.5552 (0.45); 2.5474 (0.58); 2.5380 (0.86); 2.5284 (0.66); 2.5174 (1.60); 2.5129 (2.97); 2.5084 (3.92); 2.5039 (2.90); 2.4997 (1.48); 1.2329 (0.43); 0.5381 (16.00); 0.4757 (0.34); 0.4318 (1.58); 0.4192 (2.63); 0.3849 (0.47); 0.3394 (0.68); 0.2954 (0.70) |
| 77 | 9.0269 (1.24); 9.0211 (1.48); 8.9469 (1.41); 8.9411 (1.27); 8.1832 (1.80); 7.9756 (0.58); 7.9606 (0.58); 7.9519 (0.69); 7.9414 (1.16); 7.9204 (1.81); 7.9112 (0.61); 7.8960 (0.70); 7.7341 (1.09); 7.7137 (0.91); 7.5521 (1.57); 7.5462 (0.88); 7.5421 (0.96); 7.5388 (0.99); 7.5347 (0.87); 7.5285 (1.51); 3.3806 (1.32); 3.3331 (47.92); 2.5892 (0.35); 2.5802 (0.66); 2.5695 (0.41); 2.5622 (0.35); 2.5248 (0.34); 2.5074 (13.29); 2.5031 (17.88); 2.4987 (13.84); 0.5046 (16.00); 0.4750 (0.58); 0.3881 (0.45); 0.3519 (1.14); 0.3343 (0.97) |
| 78 | 8.7509 (0.61); 8.7433 (1.19); 8.7354 (0.69); 8.1843 (1.79); 7.9746 (0.59); 7.9615 (0.62); 7.9492 (1.52); 7.9282 (1.67); 7.9202 (0.72); 7.9070 (0.74); 7.7327 (1.06); 7.7128 (0.88); 7.7108 (0.88); 7.6146 (3.04); 7.6067 (3.46); 7.5590 (1.25); 7.5546 (0.98); 7.5471 (1.34); 7.5395 (0.91); 7.5355 (1.21); 3.3332 (46.14); 2.5340 (0.43); 2.5211 (0.97); 2.5117 (7.08); 2.5076 (13.72); 2.5031 (18.01); 2.4986 (13.65); 0.5133 (16.00); 0.4148 (0.40); 0.3615 (0.47); 0.3285 (0.32); −0.0002 (0.33) |
| 79 | 8.6813 (0.83); 8.6779 (0.91); 8.6696 (0.89); 8.6662 (0.90); 8.1843 (1.77); 7.9687 (0.60); 7.9555 (0.64); 7.9448 (1.76); 7.9245 (1.65); 7.9169 (0.74); 7.9035 (0.75); 7.7323 (1.05); 7.7118 (0.89); 7.5860 (0.68); 7.5679 (1.12); 7.5544 (1.28); 7.5436 (1.38); 7.5326 (1.16); 7.4755 (0.67); 7.4636 (0.67); 7.4559 (0.53); 7.4441 (0.49); 6.8931 (0.63); 6.7581 (1.38); 6.6230 (0.69); 3.3342 (49.88); 2.6210 (0.36); 2.6101 (0.60); 2.5987 (0.36); 2.5947 (0.36); 2.5250 (0.36); 2.5113 (6.65); 2.5073 (13.21); 2.5029 (17.68); 2.4985 (13.56); 0.5173 (16.00); 0.3706 (2.27); 0.3533 (1.15) |
| 80 | 7.9473 (0.57); 7.7084 (0.39); 7.6874 (0.51); 7.4970 (0.58); 7.3192 (0.68); 7.3076 (0.47); 7.3003 (0.47); 7.2972 (0.50); 3.0952 (16.00); 2.2698 (4.75); 2.2654 (6.28); 2.2610 (4.91); 0.2752 (4.73) |
| 81 | 8.7955 (0.61); 8.7865 (0.84); 8.7801 (0.57); 7.9024 (1.00); 7.8908 (1.04); 7.7596 (2.83); 7.7539 (1.47); 7.7496 (1.40); 7.4455 (1.06); 7.4373 (1.18); 7.2849 (0.94); 7.2765 (0.95); 7.2735 (0.98); 7.2651 (0.82); 5.3016 (0.37); 3.3726 (0.44); 3.3545 (0.50); 3.3259 (17.05); 2.5773 (0.35); 2.5635 (0.52); 2.5506 (0.36); 2.5242 (0.38); 2.5108 (7.04); 2.5065 (13.77); 2.5020 (18.15); 2.4975 (13.50); 2.4933 (6.79); 1.2488 (0.34); 1.2307 (0.73); 0.4679 (1.02); 0.4596 (16.00); 0.4212 (0.48); 0.4131 (0.48); 0.3947 (0.60); 0.3902 (0.44); 0.2377 (0.53); −0.0002 (2.40) |
| 82 | 9.0571 (1.17); 9.0514 (1.34); 8.9646 (1.32); 8.9588 (1.21); 7.8946 (1.09); 7.8830 (1.13); 7.4526 (1.16); 7.4443 (1.27); 7.2744 (0.87); 7.2658 (0.88); 7.2632 (0.99); 7.2545 (0.79); 3.3245 (15.84); 3.2779 (1.79); 2.6338 (0.46); 2.6204 (0.68); 2.6061 (0.47); 2.5064 (11.35); 2.5021 (15.18); 2.4978 (11.81); 0.4543 (16.00); 0.4340 (0.65); 0.4056 (2.75); 0.3913 (3.11); −0.0002 (0.67) |
| 83 | 8.4530 (0.98); 8.4486 (0.90); 8.4413 (0.85); 8.4366 (0.84); 7.8945 (1.10); 7.8830 (1.35); 7.7113 (0.75); 7.7066 (0.79); 7.6924 (0.92); 7.6877 (0.91); 7.4956 (0.92); 7.4903 (0.33); 7.4836 (0.90); 7.4767 (0.81); 7.4647 (0.75); 7.4434 (1.12); 7.4351 (1.25); 7.2772 (0.90); 7.2687 (0.90); 7.2659 (0.97); 7.2574 (0.82); 3.3253 (22.38); 3.2274 (2.20); 2.6415 (0.32); 2.6324 (0.61); 2.6212 (0.35); 2.5236 (0.34); 2.5062 (12.33); 2.5018 (16.52); 2.4974 (12.70); 0.5014 (0.45); 0.4754 (1.06); 0.4674 (16.00); 0.4155 (0.88); 0.3987 (0.76); 0.2514 (4.97); −0.0002 (0.57) |

TABLE 2-continued

NMR peak lists
The $^1$H-NMR data (at 400 Mhz in DMSO-$d_6$) of selected examples are stated in the form of $^1$H-NMR peak lists.
For each signal peak, the δ value in ppm and the signal intensity in brackets are listed:

| Example | $^1$H-NMR (400 Mhz in DMSO-$d_6$) |
|---|---|
| 84 | 7.8854 (1.23); 7.8738 (1.31); 7.8643 (1.17); 7.8446 (1.19); 7.4369 (1.30); 7.4284 (1.84); 7.4078 (1.15); 7.3892 (0.66); 7.2742 (0.93); 7.2629 (1.09); 7.2545 (1.02); 7.1411 (0.50); 7.1375 (0.61); 7.1218 (0.85); 7.1185 (0.99); 7.1028 (0.43); 7.0991 (0.50); 7.0604 (0.96); 7.0569 (0.93); 7.0414 (0.89); 7.0379 (0.82); 3.3336 (65.60); 2.6269 (0.36); 2.6195 (0.41); 2.6105 (0.68); 2.6003 (0.46); 2.5925 (0.37); 2.5062 (16.04); 2.5019 (21.16); 2.4977 (16.31); 0.4818 (16.00); 0.4459 (1.06); 0.4392 (1.09); 0.4111 (0.46); 0.3656 (0.93); 0.2695 (0.80) |
| 85 | 7.8955 (1.19); 7.8840 (1.23); 7.7905 (0.84); 7.7716 (1.01); 7.6937 (0.37); 7.6743 (0.86); 7.6559 (0.63); 7.6265 (0.76); 7.6074 (0.88); 7.5884 (0.32); 7.4393 (1.24); 7.4311 (1.37); 7.2815 (1.00); 7.2730 (1.04); 7.2704 (1.12); 7.2617 (0.92); 7.2505 (0.96); 7.2314 (0.84); 3.3299 (50.14); 2.5690 (0.39); 2.5570 (0.63); 2.5423 (0.48); 2.5246 (0.40); 2.5105 (7.76); 2.5064 (15.44); 2.5020 (20.69); 2.4976 (15.90); 0.4571 (16.00); 0.3527 (0.46); 0.3049 (0.36); 0.2363 (2.20); −0.0002 (0.65) |
| 86 | 9.0483 (1.06); 9.0426 (1.18); 8.9555 (1.18); 8.9498 (1.06); 7.8055 (0.90); 7.8030 (0.97); 7.7992 (1.03); 7.7966 (0.95); 7.6496 (0.84); 7.6432 (0.81); 7.6377 (0.93); 7.6312 (0.85); 7.3238 (1.05); 7.3215 (1.02); 7.3119 (0.98); 7.3095 (0.95); 3.3538 (0.61); 3.3320 (38.19); 3.2766 (1.31); 2.5974 (0.38); 2.5832 (0.54); 2.5689 (0.40); 2.5247 (0.42); 2.5112 (7.78); 2.5069 (15.10); 2.5024 (19.80); 2.4979 (14.67); 2.4937 (7.33); 1.2309 (0.41); 0.4146 (0.84); 0.4109 (1.05); 0.4026 (16.00); 0.3938 (1.36); 0.3866 (2.61); 0.3699 (2.02); −0.0002 (0.77) |
| 87 | 8.7161 (0.71); 8.7123 (0.77); 8.7047 (0.78); 8.7008 (0.77); 7.8112 (0.91); 7.8089 (1.01); 7.8050 (1.08); 7.8028 (1.01); 7.6578 (0.86); 7.6514 (0.85); 7.6459 (0.98); 7.6395 (0.89); 7.6274 (0.46); 7.6102 (1.02); 7.5881 (0.81); 7.5766 (0.76); 7.5685 (0.37); 7.5570 (0.35); 7.3144 (1.06); 7.3124 (1.05); 7.3025 (1.01); 7.3005 (0.98); 6.9130 (0.62); 6.7780 (1.31); 6.6430 (0.66); 3.3259 (24.41); 3.2449 (1.64); 2.6067 (0.40); 2.5927 (0.58); 2.5791 (0.39); 2.5240 (0.46); 2.5062 (15.48); 2.5018 (20.24); 2.4974 (15.19); 1.2303 (0.46); 0.4161 (16.00); 0.3827 (1.61); 0.3776 (1.60); 0.3676 (3.19); −0.0002 (1.76) |
| 88 | 7.6110 (0.32); 7.4468 (0.44); 3.1531 (16.00); 3.0456 (1.22); 2.3214 (3.42); 2.3170 (4.49); 2.3126 (3.41); 0.2322 (4.18) |
| 89 | 7.8520 (1.06); 7.8505 (1.08); 7.8323 (1.12); 7.8308 (1.09); 7.7987 (1.08); 7.7962 (1.16); 7.7924 (1.25); 7.7898 (1.17); 7.6471 (1.08); 7.6407 (0.99); 7.6352 (1.15); 7.6287 (1.03); 7.4061 (0.51); 7.4038 (0.52); 7.3873 (1.09); 7.3851 (1.08); 7.3686 (0.64); 7.3663 (0.61); 7.3168 (1.25); 7.3144 (1.25); 7.3049 (1.15); 7.3025 (1.14); 7.1256 (0.55); 7.1216 (0.61); 7.1062 (0.88); 7.1024 (0.92); 7.0872 (0.50); 7.0832 (0.54); 6.9658 (0.93); 6.9621 (0.93); 6.9468 (0.89); 6.9431 (0.83); 3.3523 (0.47); 3.3310 (51.59); 2.9754 (0.40); 2.5637 (0.36); 2.5562 (0.42); 2.5470 (0.69); 2.5370 (0.50); 2.5290 (0.47); 2.5243 (0.45); 2.5106 (6.97); 2.5063 (13.79); 2.5018 (18.30); 2.4973 (13.70); 2.4930 (6.92); 0.4298 (16.00); 0.3466 (0.70); 0.3181 (0.74); −0.0002 (0.95) |
| 90 | 7.8036 (0.89); 7.8011 (0.96); 7.7973 (1.03); 7.7947 (0.95); 7.7776 (0.65); 7.7586 (0.79); 7.6687 (0.33); 7.6558 (1.01); 7.6496 (1.47); 7.6441 (1.03); 7.6375 (0.96); 7.6334 (0.63); 7.6109 (0.55); 7.5918 (0.63); 7.3139 (1.01); 7.3114 (0.99); 7.3020 (0.94); 7.2995 (0.92); 7.1336 (0.73); 7.1149 (0.71); 3.3273 (31.39); 2.5108 (7.06); 2.5064 (13.82); 2.5018 (18.04); 2.4973 (13.34); 2.4929 (6.79); 0.4181 (0.97); 0.4098 (16.00); 0.4015 (0.96); 0.3746 (0.34); 0.3047 (0.35); −0.0002 (1.53) |
| 91 | 8.7785 (0.71); 8.7686 (0.72); 8.7671 (0.71); 7.8100 (0.91); 7.8076 (0.98); 7.8037 (1.07); 7.8013 (0.98); 7.7478 (0.48); 7.7362 (0.48); 7.7281 (0.78); 7.7164 (0.73); 7.6594 (0.93); 7.6530 (1.66); 7.6479 (1.43); 7.6411 (0.92); 7.6330 (0.59); 7.3146 (1.05); 7.3123 (1.03); 7.3026 (1.00); 7.3003 (0.97); 3.3266 (22.37); 2.5242 (0.61); 2.5198 (0.71); 2.5108 (6.10); 2.5066 (11.40); 2.5021 (14.95); 2.4976 (11.44); 0.4202 (1.04); 0.4120 (16.00); −0.0002 (0.55) |
| 92 | 8.6639 (0.51); 8.6608 (0.55); 8.6522 (0.55); 8.6490 (0.55); 7.9089 (0.48); 7.8897 (0.54); 7.5649 (0.38); 7.5530 (0.39); 7.5453 (0.37); 7.5335 (0.34); 7.1762 (0.54); 7.1567 (1.09); 7.1382 (0.86); 7.0162 (1.53); 6.9969 (1.40); 6.9878 (0.57); 6.8521 (0.92); 6.7167 (0.46); 3.2520 (32.41); 2.9720 (1.32); 2.6631 (0.41); 2.4348 (6.06); 2.4306 (12.01); 2.4261 (16.00); 2.4217 (12.18); 2.1647 (2.80); 0.3668 (0.66); 0.3493 (0.68); 0.3028 (0.77); 0.2941 (0.63); −0.0002 (11.18); −0.0758 (1.12) |
| 93 | 8.9785 (0.79); 8.9729 (0.90); 8.8808 (0.88); 8.8753 (0.81); 7.1739 (0.60); 7.1546 (1.11); 7.1359 (1.01); 7.0097 (1.99); 6.9920 (1.59); 3.2924 (0.35); 3.2551 (37.41); 2.9967 (0.83); 2.5962 (0.35); 2.5858 (0.50); 2.4447 (0.35); 2.4313 (6.07); 2.4271 (12.00); 2.4226 (16.00); 2.4182 (12.16); 2.1621 (2.96); 1.1509 (0.46); 0.3809 (0.64); 0.3636 (0.69); 0.3168 (0.60); 0.0081 (1.04); −0.0002 (12.13); −0.0801 (0.76) |
| 94 | 8.3822 (0.60); 8.3775 (0.64); 8.3702 (0.65); 8.3655 (0.64); 7.8039 (0.58); 7.7992 (0.62); 7.7850 (0.68); 7.7802 (0.66); 7.4365 (0.66); 7.4244 (0.66); 7.4175 (0.62); 7.4055 (0.59); 7.1700 (0.56); 7.1492 (1.04); 7.1317 (0.93); 7.0073 (1.98); 6.9890 (1.59); 3.2453 (16.00); 2.9167 (0.42); 2.6490 (0.34); 2.6348 (0.45); 2.6201 (0.33); 2.4301 (4.44); 2.4258 (8.88); 2.4213 (11.86); 2.4168 (8.96); 2.4125 (4.59); 2.1605 (2.81); 0.3729 (1.23); 0.3571 (1.28); 0.0076 (0.60); −0.0002 (11.49); −0.0806 (1.24) |
| 95 | 7.7779 (0.49); 7.7598 (0.51); 7.7581 (0.51); 7.3459 (0.52); 7.3436 (0.52); 7.3272 (0.33); 7.3248 (0.32); 7.1549 (0.83); 7.1510 (0.66); 7.1358 (1.24); 7.1170 (0.67); 7.0359 (0.43); 7.0320 (0.43); 7.0029 (0.95); 6.9853 (0.73); 6.9721 (0.45); 3.2308 (16.00); 2.5785 (0.35); 2.4167 (4.72); 2.4123 (9.31); 2.4077 (12.30); 2.4032 (9.14); 2.3989 (4.57); 2.1587 (2.05); 0.3340 (0.55); 0.3141 (0.34); −0.0002 (8.48); −0.0080 (0.47); −0.0937 (1.18) |
| 96 | 7.7283 (0.61); 7.7088 (0.76); 7.6457 (0.65); 7.6270 (0.45); 7.5677 (0.43); 7.5484 (0.60); 7.4298 (0.70); 7.4108 (0.59); 7.1817 (0.66); 7.1615 (1.20); 7.1488 (0.32); 7.1434 (1.04); 7.0186 (2.10); 7.0000 (1.81); 3.2546 (18.43); 2.5569 (0.46); 2.4535 (0.33); 2.4401 (6.12); 2.4357 (12.10); 2.4311 (16.00); 2.4266 (11.90); 2.4223 (5.97); 2.1611 (3.20); 0.0077 (0.72); −0.0002 (13.48); −0.0080 (0.75); −0.0707 (2.15) |
| 97 | 8.7304 (0.78); 8.7191 (0.81); 7.9694 (0.74); 7.9499 (0.85); 7.7227 (0.69); 7.7110 (0.69); 7.7030 (0.63); 7.6912 (0.59); 7.1824 (0.86); 7.1618 (1.57); 7.1499 (0.36); 7.1441 (1.36); 7.0186 (2.98); 7.0003 (2.45); 6.9816 (0.38); 3.2539 (18.23); 2.5819 (0.34); 2.5684 (0.55); 2.5577 (0.35); 2.4528 (0.32); 2.4351 (12.08); 2.4306 (16.00); 2.4262 (12.17); 2.1605 (4.17); 0.3828 (0.48); −0.0002 (16.50); −0.0714 (0.81) |
| 98 | 8.7397 (2.95); 8.7309 (2.92); 8.7279 (2.96); 7.9930 (2.64); 7.9737 (2.94); 7.6455 (2.02); 7.6336 (2.07); 7.6260 (1.97); 7.6140 (1.82); 7.4001 (3.07); 7.3799 (3.42); 7.2731 (0.84); 7.2679 (1.30); 7.2541 (4.25); 7.2487 (6.63); 7.2297 (3.19); 7.2129 (1.03); 7.2103 (1.03); 7.1371 (1.71); 7.1316 (1.60); 7.1168 (2.14); 7.1002 (1.22); 7.0947 (1.16); 7.0668 (2.27); 6.9315 (4.74); 6.7962 (2.41); 3.3521 (0.47); 3.3276 (92.93); |

TABLE 2-continued

NMR peak lists
The $^1$H-NMR data (at 400 Mhz in DMSO-d$_6$) of selected examples are stated in the form of $^1$H-NMR peak lists.
For each signal peak, the δ value in ppm and the signal intensity in brackets are listed:

| Example | $^1$H-NMR (400 Mhz in DMSO-d$_6$) |
|---|---|
|  | 3.1005 (7.59); 2.8902 (0.38); 2.7799 (0.52); 2.7697 (1.12); 2.7621 (1.42); 2.7518 (2.15); 2.7427 (1.32); 2.7357 (1.17); 2.7256 (0.61); 2.6706 (0.44); 2.6663 (0.41); 2.5065 (43.07); 2.5021 (57.71); 2.4977 (44.59); 2.4196 (16.00); 2.3290 (0.39); 1.2347 (0.60); 0.4748 (0.62); 0.4571 (3.43); 0.4406 (3.66); 0.4295 (2.13); 0.4109 (1.84); 0.4007 (4.53); 0.3720 (0.70); 0.1072 (55.93); 0.0752 (1.28); −0.0002 (1.42) |
| 99 | 8.9484 (0.76); 8.9426 (0.87); 8.8526 (0.87); 8.8468 (0.81); 7.2913 (0.58); 7.2720 (0.66); 7.2700 (0.66); 7.1422 (0.90); 7.1368 (1.34); 7.1226 (0.68); 7.1200 (0.66); 7.0291 (0.36); 7.0122 (0.33); 7.0089 (0.41); 7.0039 (0.35); 3.2158 (11.59); 3.0275 (0.75); 2.5730 (0.42); 2.4136 (0.35); 2.4002 (6.07); 2.3958 (12.05); 2.3913 (16.00); 2.3867 (11.90); 2.3824 (5.94); 2.3176 (3.11); 1.1200 (0.40); 0.3665 (0.59); 0.3497 (0.65); 0.3116 (0.60); 0.0250 (0.85); 0.0077 (0.93); −0.0002 (11.61); −0.1113 (1.99) |
| 100 | 8.3536 (0.71); 8.3489 (0.76); 8.3416 (0.77); 8.3370 (0.76); 7.7787 (0.71); 7.7740 (0.74); 7.7598 (0.82); 7.7550 (0.80); 7.4088 (0.80); 7.3969 (0.79); 7.3900 (0.76); 7.3779 (0.73); 7.2869 (0.70); 7.2675 (0.77); 7.1404 (1.01); 7.1351 (1.54); 7.1189 (0.75); 7.1164 (0.73); 7.0249 (0.40); 7.0192 (0.37); 7.0047 (0.50); 3.2128 (16.00); 2.6340 (0.37); 2.6191 (0.52); 2.6050 (0.38); 2.3945 (10.35); 2.3900 (13.72); 2.3856 (10.35); 2.3131 (3.72); 0.3590 (1.57); 0.3434 (1.39); 0.1395 (0.56); −0.0002 (12.50); −0.1123 (1.33) |
| 101 | 7.0088 (0.32); 3.2130 (16.00); 2.3862 (1.60); 2.3822 (3.14); 2.3777 (4.17); 2.3732 (3.15); 2.3081 (0.98); −0.0002 (3.80) |
| 102 | 7.1452 (0.45); 3.2342 (16.00); 2.4101 (1.79); 2.4058 (3.54); 2.4013 (4.71); 2.3967 (3.53); 2.3925 (1.78); 2.3124 (0.98); −0.0002 (3.77); −0.1016 (0.33) |
| 103 | 8.8048 (2.82); 8.7941 (2.90); 8.0489 (2.63); 8.0303 (3.05); 7.7992 (2.46); 7.7875 (2.47); 7.7795 (2.28); 7.7677 (2.21); 7.4011 (3.18); 7.3807 (3.45); 7.2721 (0.64); 7.2660 (1.18); 7.2516 (5.09); 7.2471 (7.09); 7.2330 (3.26); 7.2308 (3.22); 7.2139 (1.06); 7.2119 (1.00); 7.1385 (1.76); 7.1324 (1.58); 7.1180 (2.14); 7.1018 (1.26); 7.0962 (1.15); 3.3258 (80.24); 3.1654 (0.36); 3.0298 (0.33); 3.0154 (0.38); 3.0049 (0.37); 2.9968 (0.40); 2.9787 (0.37); 2.8909 (0.53); 2.7317 (0.41); 2.6818 (0.65); 2.6673 (1.56); 2.6541 (1.98); 2.6427 (1.24); 2.6274 (0.73); 2.5245 (1.17); 2.5108 (23.53); 2.5067 (46.77); 2.5023 (62.54); 2.4979 (48.00); 2.4132 (16.00); 2.3291 (0.42); 2.3246 (0.32); 2.2113 (0.60); 1.2352 (0.63); 0.4675 (1.78); 0.2513 (0.41); 0.1322 (0.60); 0.1028 (57.38); 0.0705 (0.69); −0.0002 (2.71) |
| 104 | 8.7424 (3.05); 8.7394 (3.27); 8.7307 (3.32); 8.7276 (3.27); 8.0009 (2.93); 7.9814 (3.26); 7.6440 (2.28); 7.6321 (2.34); 7.6244 (2.22); 7.6125 (2.07); 7.2822 (2.33); 7.2627 (5.59); 7.2432 (3.74); 7.1695 (5.42); 7.1411 (3.12); 7.1213 (2.22); 7.0673 (5.14); 7.0456 (2.91); 6.9325 (5.48); 6.7972 (2.81); 3.3299 (134.57); 3.0429 (8.14); 2.8906 (0.47); 2.7795 (0.58); 2.7692 (1.25); 2.7616 (1.61); 2.7514 (2.45); 2.7423 (1.49); 2.7348 (1.36); 2.7250 (0.68); 2.6716 (0.40); 2.5247 (1.24); 2.5069 (44.91); 2.5024 (59.35); 2.4980 (44.63); 2.3290 (0.40); 2.3248 (0.33); 2.2823 (16.00); 1.2350 (0.62); 0.4504 (3.97); 0.4330 (4.03); 0.4214 (1.78); 0.3958 (1.86); 0.3860 (4.59); 0.3773 (3.76); 0.3580 (0.82); 0.2313 (0.37); 0.0831 (63.20); 0.0374 (0.76); −0.0002 (1.41); −0.0684 (0.36) |
| 105 | 8.9702 (0.78); 8.9644 (0.89); 8.8750 (0.89); 8.8692 (0.84); 7.1937 (0.41); 7.1742 (0.97); 7.1548 (0.68); 7.0758 (0.92); 7.0533 (0.59); 7.0338 (0.45); 6.9724 (0.60); 6.9532 (0.49); 3.2364 (11.24); 2.9803 (0.88); 2.5792 (0.48); 2.4345 (0.34); 2.4208 (6.17); 2.4167 (12.08); 2.4123 (16.00); 2.4078 (12.04); 2.4038 (6.17); 2.1931 (2.74); 1.1410 (0.39); 0.3772 (0.64); 0.3598 (0.69); 0.3122 (0.60); 0.0369 (0.41); 0.0073 (1.18); −0.0002 (11.19); −0.0902 (2.03); −0.1390 (0.60) |
| 106 | 7.1720 (0.37); 7.0785 (0.33); 3.2471 (16.00); 2.4226 (1.75); 2.4182 (3.48); 2.4137 (4.63); 2.4091 (3.45); 2.4047 (1.72); 2.1924 (0.99); 0.3719 (0.46); 0.3563 (0.51); −0.0002 (4.26); −0.0068 (0.42) |
| 107 | 7.7737 (0.43); 7.7720 (0.44); 7.7540 (0.47); 7.7523 (0.45); 7.3404 (0.46); 7.3382 (0.46); 7.1572 (1.01); 7.1379 (0.76); 7.0756 (0.58); 7.0715 (0.42); 7.0318 (0.67); 7.0126 (0.48); 7.0092 (0.41); 6.9701 (0.38); 3.2250 (16.00); 2.4094 (3.46); 2.4051 (6.82); 2.4006 (9.04); 2.3961 (6.75); 2.3918 (3.40); 2.1941 (1.66); 0.3332 (0.49); −0.0002 (7.13); −0.1013 (0.80); −0.1505 (0.38) |
| 108 | 7.7240 (0.52); 7.7045 (0.62); 7.6412 (0.56); 7.6223 (0.38); 7.5642 (0.40); 7.5450 (0.52); 7.4391 (0.56); 7.4200 (0.47); 7.2044 (0.39); 7.1849 (0.84); 7.1655 (0.61); 7.0890 (0.81); 7.0621 (0.51); 7.0421 (0.41); 6.9841 (0.54); 6.9652 (0.46); 3.2672 (0.81); 3.2471 (16.00); 2.5625 (0.40); 2.4331 (6.04); 2.4288 (10.57); 2.4244 (13.54); 2.4200 (10.31); 2.1957 (2.27); 0.0498 (0.33); 0.0190 (0.60); −0.0002 (9.69); −0.0779 (1.40); −0.1266 (0.63) |
| 109 | 8.8050 (3.17); 8.7942 (3.27); 8.0599 (2.96); 8.0406 (3.41); 7.7981 (2.73); 7.7864 (2.75); 7.7784 (2.54); 7.7667 (2.39); 7.2837 (2.35); 7.2642 (5.58); 7.2448 (3.71); 7.1677 (5.43); 7.1428 (3.15); 7.1231 (2.21); 7.0617 (3.50); 7.0426 (2.92); 3.3263 (85.63); 3.1233 (0.40); 3.1174 (0.40); 3.0149 (0.34); 2.9975 (0.34); 2.9784 (0.34); 2.9610 (0.35); 2.9235 (0.40); 2.8909 (0.79); 2.7317 (0.48); 2.6804 (0.74); 2.6672 (1.66); 2.6528 (2.20); 2.6424 (1.39); 2.6262 (0.66); 2.5067 (50.80); 2.5024 (67.08); 2.4981 (51.47); 2.3335 (0.33); 2.3292 (0.46); 2.2732 (16.00); 2.1024 (0.53); 1.2351 (0.72); 0.4590 (1.94); 0.3612 (0.54); 0.3328 (0.49); 0.2268 (0.43); 0.0785 (62.96); 0.0520 (0.61); −0.0003 (2.57); −0.0728 (0.34) |
| 110 | 8.7411 (3.09); 8.7321 (3.07); 8.7294 (3.11); 7.9985 (2.81); 7.9791 (3.11); 7.6464 (2.15); 7.6346 (2.20); 7.6269 (2.09); 7.6151 (1.93); 7.5437 (4.80); 7.5388 (5.22); 7.3397 (1.39); 7.3348 (1.21); 7.3188 (4.75); 7.3138 (5.10); 7.3024 (7.93); 7.2816 (2.11); 7.0671 (2.30); 6.9318 (4.95); 6.7965 (2.52); 3.3306 (161.79); 3.0911 (8.18); 2.8912 (0.45); 2.7902 (0.54); 2.7801 (1.15); 2.7723 (1.46); 2.7621 (2.26); 2.7531 (1.42); 2.7462 (1.21); 2.7357 (0.63); 2.6718 (0.48); 2.6675 (0.37); 2.5248 (1.35); 2.5071 (51.24); 2.5027 (68.35); 2.4984 (52.85); 2.4200 (16.00); 2.3338 (0.35); 2.3294 (0.45); 2.3251 (0.36); 1.2350 (0.66); 0.4823 (0.65); 0.4653 (3.60); 0.4488 (3.83); 0.4378 (2.27); 0.4197 (1.98); 0.4095 (4.78); 0.3808 (0.71); 0.2556 (0.34); 0.1072 (57.78); −0.0002 (1.44) |
| 111 | 8.9479 (0.33); 8.9421 (0.38); 8.8535 (0.38); 8.8478 (0.36); 7.4332 (0.39); 7.4282 (0.41); 7.2079 (0.40); 7.2028 (0.42); 7.1898 (0.62); 3.2215 (16.00); 3.0215 (0.33); 2.3995 (3.00); 2.3953 (5.80); 2.3908 (7.58); 2.3863 (5.62); 2.3821 (2.82); 2.3159 (1.24); −0.0002 (4.79); −0.1124 (0.84) |
| 112 | 8.3552 (0.33); 8.3505 (0.36); 8.3432 (0.36); 8.3385 (0.36); 7.7780 (0.33); 7.7638 (0.36); 7.7590 (0.35); 7.4299 (0.46); 7.4249 (0.49); 7.4101 (0.39); 7.3981 (0.37); 7.3912 (0.36); 7.3791 (0.34); 7.2060 (0.49); 7.2009 (0.52); 7.1898 (0.78); 3.2163 (16.00); 2.3992 (2.99); 2.3949 (5.93); 2.3904 (7.89); 2.3858 (5.91); 2.3815 (2.99); 2.3132 (1.53); 0.3673 (0.69); 0.3515 (0.59); 0.1394 (0.40); −0.0002 (5.58); −0.1124 (0.58) |

TABLE 2-continued

NMR peak lists
The ¹H-NMR data (at 400 Mhz in DMSO-d₆) of selected examples are stated in the form of ¹H-NMR peak lists.
For each signal peak, the δ value in ppm and the signal intensity in brackets are listed:

| Example | ¹H-NMR (400 Mhz in DMSO-d₆) |
|---|---|
| 113 | 7.7521 (0.91); 7.7324 (0.98); 7.4109 (1.16); 7.3386 (0.42); 7.3367 (0.40); 7.3198 (0.94); 7.3012 (0.58); 7.1901 (3.39); 7.1356 (0.78); 7.1319 (0.89); 7.1166 (0.70); 7.1129 (0.71); 7.0303 (0.54); 7.0263 (0.51); 7.0109 (0.81); 7.0074 (0.77); 6.9919 (0.47); 6.9880 (0.43); 3.1997 (15.48); 2.5817 (0.33); 2.5730 (0.59); 2.5619 (0.36); 2.5548 (0.33); 2.4001 (0.33); 2.3866 (6.28); 2.3824 (12.16); 2.3780 (16.00); 2.3735 (11.97); 2.3114 (3.53); 0.3373 (0.97); 0.2950 (0.60); 0.1460 (0.58); 0.0443 (0.51); −0.0002 (13.57); −0.0092 (1.12); −0.0503 (0.41); −0.1243 (1.90) |
| 114 | 7.7026 (0.44); 7.6830 (0.56); 7.6203 (0.48); 7.6018 (0.33); 7.5427 (0.33); 7.5236 (0.45); 7.4408 (0.70); 7.4359 (0.75); 7.4140 (0.49); 7.3949 (0.41); 7.2169 (0.73); 7.2118 (0.77); 7.1997 (1.18); 7.1789 (0.33); 3.2244 (16.00); 2.5539 (0.32); 2.4098 (5.08); 2.4057 (9.91); 2.4012 (13.06); 2.3968 (9.87); 2.3928 (5.07); 2.3128 (2.06); 0.1356 (0.36); 0.0364 (0.37); 0.0091 (0.69); −0.0002 (8.37); −0.1011 (1.58) |
| 115 | 8.8068 (2.97); 8.7960 (3.02); 8.0557 (2.76); 8.0364 (3.16); 7.8006 (2.60); 7.7888 (2.61); 7.7809 (2.38); 7.7691 (2.34); 7.5439 (5.16); 7.5388 (5.48); 7.4341 (0.57); 7.4292 (0.55); 7.3409 (1.62); 7.3358 (1.42); 7.3313 (0.48); 7.3201 (4.98); 7.3149 (5.16); 7.3004 (8.13); 7.2795 (2.55); 3.3257 (76.96); 3.1640 (0.38); 3.1598 (0.38); 3.1540 (0.38); 3.0337 (0.34); 3.0162 (0.38); 2.9978 (0.41); 2.9782 (0.39); 2.8914 (0.58); 2.7320 (0.43); 2.6917 (0.63); 2.6765 (1.62); 2.6721 (1.44); 2.6638 (2.24); 2.6528 (1.32); 2.6370 (0.64); 2.5245 (1.31); 2.5113 (25.17); 2.5072 (49.69); 2.5027 (66.08); 2.4983 (50.20); 2.4134 (16.00); 2.3338 (0.32); 2.3295 (0.44); 2.3249 (0.34); 2.2097 (0.62); 1.2349 (0.71); 0.4763 (1.83); 0.4414 (1.28); 0.3730 (0.61); 0.3644 (3.43); 0.3281 (0.48); 0.2514 (0.41); 0.1470 (0.60); 0.1027 (60.58); 0.0590 (0.71); 0.0254 (0.32); −0.0002 (3.17); −0.0491 (0.33) |
| 116 | 8.9599 (0.36); 8.9537 (0.52); 8.9467 (0.36); 8.8666 (0.44); 8.8619 (0.69); 7.1933 (0.41); 7.0782 (0.91); 7.0736 (0.84); 5.2039 (0.67); 3.2729 (0.70); 3.2547 (0.82); 3.2279 (16.00); 2.9618 (0.54); 2.9438 (0.33); 2.4239 (0.37); 2.4105 (6.12); 2.4062 (11.92); 2.4017 (15.68); 2.3971 (11.68); 2.3929 (5.88); 2.2202 (1.09); 1.1485 (0.59); 1.1305 (1.25); 1.1123 (0.56); 0.3696 (0.71); 0.1474 (0.28); 0.1423 (1.77); 0.1355 (1.21); 0.1305 (0.53); 0.0059 (1.24); −0.0002 (5.70); −0.0074 (0.89); −0.0109 (0.76); −0.1010 (2.11) |
| 117 | 8.6524 (0.46); 8.6503 (0.46); 8.6411 (0.49); 7.9232 (0.36); 7.9037 (0.40); 7.5555 (0.33); 7.5436 (0.34); 7.5360 (0.32); 7.1996 (0.64); 7.1954 (0.40); 7.0888 (1.46); 7.0845 (1.40); 6.8439 (0.61); 5.2135 (0.65); 3.2822 (0.68); 3.2640 (0.73); 3.2356 (16.00); 2.9484 (1.04); 2.6710 (0.42); 2.4151 (10.48); 2.4109 (13.58); 2.4067 (10.42); 2.2287 (1.79); 1.1578 (0.63); 1.1398 (1.31); 1.1216 (0.59); 0.3652 (0.64); 0.3486 (0.59); 0.3026 (0.59); 0.2942 (0.49); 0.1569 (0.39); 0.1552 (0.39); 0.1518 (0.41); 0.0091 (0.85); −0.0002 (7.33); −0.0078 (0.97); −0.0916 (1.59) |
| 118 | 8.3693 (0.66); 8.3647 (0.71); 8.3574 (0.72); 8.3527 (0.71); 7.8119 (0.63); 7.8072 (0.65); 7.7930 (0.74); 7.7882 (0.70); 7.4244 (0.71); 7.4124 (0.70); 7.4055 (0.68); 7.3935 (0.65); 7.1971 (0.53); 7.1925 (1.03); 7.1879 (0.61); 7.0830 (2.34); 7.0784 (2.20); 5.2039 (0.45); 3.2743 (0.44); 3.2561 (0.48); 3.2268 (16.00); 2.6458 (0.35); 2.6323 (0.52); 2.6179 (0.35); 2.4081 (11.24); 2.4037 (14.64); 2.3992 (10.95); 2.2203 (2.69); 1.1504 (0.40); 1.1323 (0.87); 1.1141 (0.38); 0.3687 (1.46); 0.3536 (1.62); −0.0002 (11.45); −0.0088 (1.05); −0.0988 (1.96) |
| 119 | 7.7669 (0.78); 7.7650 (0.80); 7.7471 (0.84); 7.7452 (0.81); 7.3530 (0.36); 7.3504 (0.37); 7.3342 (0.80); 7.3317 (0.80); 7.3154 (0.50); 7.3129 (0.49); 7.1802 (0.58); 7.1755 (1.15); 7.1708 (0.71); 7.1641 (0.73); 7.1602 (0.77); 7.1450 (0.62); 7.1412 (0.60); 7.0818 (2.55); 7.0771 (2.36); 7.0457 (0.43); 7.0417 (0.42); 7.0264 (0.68); 7.0227 (0.65); 7.0074 (0.42); 7.0033 (0.38); 5.1926 (0.52); 3.2627 (0.49); 3.2445 (0.52); 3.2147 (15.88); 2.5837 (0.47); 2.5663 (0.33); 2.4149 (0.35); 2.4014 (6.13); 2.3970 (12.11); 2.3924 (16.00); 2.3879 (11.83); 2.3834 (5.82); 2.2253 (2.69); 1.1389 (0.44); 1.1208 (0.95); 1.1027 (0.42); 0.3333 (0.84); 0.3155 (0.60); 0.2997 (0.54); 0.0076 (0.78); −0.0002 (12.69); −0.0083 (1.25); −0.1097 (2.59) |
| 120 | 7.7187 (0.61); 7.6991 (0.76); 7.6360 (0.66); 7.6174 (0.47); 7.5598 (0.44); 7.5407 (0.61); 7.4446 (0.67); 7.4257 (0.58); 7.2078 (0.54); 7.2032 (1.05); 7.1986 (0.62); 7.0924 (2.39); 7.0878 (2.26); 5.2155 (0.55); 3.2872 (0.68); 3.2689 (1.12); 3.2509 (53.88); 2.5818 (0.37); 2.5666 (0.45); 2.4396 (0.36); 2.4260 (6.35); 2.4218 (12.24); 2.4173 (16.00); 2.4128 (11.91); 2.2258 (2.78); 1.1635 (0.48); 1.1455 (1.04); 1.1273 (0.46); −0.0002 (11.90); −0.0080 (1.19); −0.0859 (1.64) |
| 121 | 8.8079 (3.31); 8.7965 (3.35); 8.0747 (3.08); 8.0551 (3.49); 7.8021 (2.92); 7.7903 (2.93); 7.7823 (2.76); 7.7706 (2.54); 7.2973 (3.09); 7.2927 (6.17); 7.2881 (3.71); 7.1794 (13.76); 7.1748 (13.14); 6.8966 (0.43); 6.8921 (0.43); 3.3285 (138.88); 3.1080 (0.42); 3.0805 (0.40); 3.0452 (0.36); 3.0332 (0.34); 3.0159 (0.37); 2.9970 (0.37); 2.9740 (0.37); 2.9356 (0.42); 2.8915 (0.83); 2.7323 (0.50); 2.6924 (0.65); 2.6768 (1.70); 2.6722 (1.58); 2.6646 (2.42); 2.6541 (1.44); 2.6377 (0.71); 2.5252 (1.37); 2.5118 (26.36); 2.5075 (52.59); 2.5029 (70.23); 2.4985 (53.31); 2.4943 (27.71); 2.3296 (0.65); 2.3110 (16.00); 2.1415 (0.52); 1.2349 (0.80); 0.4668 (2.02); 0.3766 (0.56); 0.3434 (0.49); 0.3329 (0.47); 0.2357 (0.44); 0.0873 (66.37); −0.0002 (2.95); −0.0642 (0.38) |

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

The ¹H-NMR peak lists are similar to classical ¹H-NMR prints and contain therefore usually all peaks, which are listed at classical NMR-interpretation. Additionally they can show like classical ¹H-NMR prints signals of solvents, stereoisomers of the target compounds, which are also object of the invention, and/or peaks of impurities. To show compound signals in the delta-range of solvents and/or water the usual peaks of solvents, for example peaks of DMSO in DMSO-d6 and the peak of water are shown in our ¹H-NMR peak lists and have usually on average a high intensity.

The peaks of stereoisomers of the target compounds and/or peaks of impurities have usually on average a lower intensity than the peaks of target compounds (for example with a purity >90%). Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values), can isolate the peaks of the target compounds as needed optionally using additional intensity filters. This isolation would be similar to relevant peak picking at classical $^1$H-NMR interpretation.

Further details of NMR-data description with peak lists can be found in the publication "Citation of NMR Peaklist Data within Patent Applications" of the Research Disclosure Database Number 564025.

The following examples illustrate in a non-limiting manner the preparation and efficacy of the compounds of formula (I) according to the invention.

GENERAL PREPARATION EXAMPLE 1

Preparation of Amide of Formula (I) on Chemspeed™ Apparatus

In a 13 mL Chemspeed™ vial is distributed 4 mL of a 0.15 molar solution of the amine (II) (0.60 mmol) in dichloromethane followed by 0.72 mmol of triethylamine. At a rate of 1 mL/mn, 2 mL of a 0.30 molar solution of the acyl chloride (III) ($L^1$=Cl) (0.60 mmole) are added and the mixture is then stirred at room temperature overnight. 1 mL of water is then added and the mixture is poured over a basic alumina cartridge (2 g) and eluted with dichloromethane. The solvents are removed and the crude amide derivative is analyzed by LCMS and NMR. Insufficiently pure compounds are further purified by preparative LCMS.

GENERAL PREPARATION EXAMPLE 2

Thionation of Amide of Formula (I) on Chemspeed™ Apparatus

In a 13 mL Chemspeed™ vial is weighted 0.27 mmol of phosphorous pentasulfide ($P_2S_5$). 3 mL of a 0.18 molar solution of the amide (I) (0.54 mmol) in dioxane is added and the mixture is heated at reflux for two hours. The temperature is then cooled to 80° C. and 2.5 mL of water are added. The mixture is heated at 80° C. for one more hour. 2 mL of water are then added and the reaction mixture is extracted twice by 4 mL of dichloromethane. The organic phase is deposited on a basic alumina cartridge (2 g) and eluted twice by 8 mL of dichloromethane. The solvents are removed and the crude thioamide derivative is analyzed by LCMS and NMR. Insufficiently pure compounds are further purified by preparative LCMS.

PREPARATION EXAMPLE 3

Preparation of 2-(difluoromethyl)-N-{[dimethyl(phenyl)silyl]methyl}nicotinamide (compound 1) 121 mg (0.6 mmol) of 1-[dimethyl(phenyl)silyl]methanamine are reacted with 126 mg (0.66 mmol) of 2-(difluoromethyl)nicotinoyl chloride according to the general preparation example 1, to yield 142 mg (72%) 2-(difluoromethyl)-N-{[dimethyl(phenyl)silyl]methyl}nicotinamide of 97% purety. (M+H=321).

EXAMPLE A

In Vivo Preventive Test on Sphaerotheca fuliginea (Powdery Mildew on Cucurbits)

The active ingredients tested are prepared by homogenization in a mixture of acetone/tween/DMSO and then diluted with water to obtain the desired active material concentration.

Gherkin plants ("Vert petit de Paris" variety), sown in starter cups on a 50/50 peat soil-pozzolana substrate and grown at 24° C., are treated at the Z11 cotyledon stage by spraying with the active ingredient prepared as described above. Plants, used as controls, are treated with the mixture of acetone/tween/DMSO/water not containing the active material.

After 24 hours, the plants are contaminated by spraying the cotyledons with an aqueous suspension of Sphaerotheca fuliginea spores (100 000 spores per mL). The spores are collected from infected plants. The contaminated gherkin plants are incubated at about 20° C. and at 70-80% relative humidity.

Grading (% of efficacy) is carried out 12 days after the contamination, in comparison with the control plants.

Under these conditions, good (at least 70%) to excellent (at least 95%) protection is observed at a dose of 500 ppm of active ingredient with the following compounds from table A:

TABLE A

| Example | Efficacy |
|---------|----------|
| 1 | 98 |
| 2 | 83 |
| 5 | 89 |
| 10 | 78 |
| 11 | 94 |
| 14 | 98 |
| 15 | 72 |
| 20 | 100 |
| 21 | 98 |
| 22 | 78 |
| 26 | 93 |
| 36 | 94 |
| 41 | 78 |
| 44 | 94 |
| 45 | 83 |
| 48 | 98 |
| 50 | 98 |
| 52 | 94 |
| 54 | 83 |
| 56 | 83 |
| 62 | 79 |
| 63 | 71 |

EXAMPLE B

In Vivo Preventive Test on Alternaria solani (Tomato)

Solvent: 49 parts by weight of N,N-dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after this treatment, the plants are inoculated with an aqueous spore suspension of Alternaria solani. The plants remain for one day in an incubation cabinet at approximately 22° C. and a relative atmospheric humidity of 100%. Then the plants are placed in an incubation cabinet at approximately 20° C. and a relative atmospheric humidity of 96%.

The test is evaluated 7 days after the inoculation. 0% means an efficacy which corresponds to that of the untreated control while an efficacy of 100% means that no disease is observed.

Under these conditions, good (at least 90%) to excellent (at least 95%) protection is observed at a dose of 500 ppm of active ingredient with the following compounds from table B:

TABLE B

| Example | Efficacy |
| --- | --- |
| 1 | 95 |
| 28 | 89 |
| 29 | 95 |
| 32 | 89 |
| 34 | 89 |
| 62 | 94 |
| 63 | 95 |
| 72 | 89 |
| 74 | 78 |
| 77 | 78 |
| 79 | 89 |
| 86 | 75 |
| 87 | 88 |
| 91 | 78 |
| 92 | 78 |
| 93 | 75 |
| 104 | 90 |
| 110 | 70 |
| 117 | 75 |

EXAMPLE C

In Vivo Preventive Test on *Pyrenophora teres* (Barley)

Solvent: 49 parts by weight of N,N-dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after this treatment, the plants are inoculated with an aqueous spore suspension of *Pyrenophora teres*. The plants remain for 48 hours in an incubation cabinet at 22° C. and a relative atmospheric humidity of 100%. Then the plants are placed in a greenhouse at a temperature of approximately 20° C. and a relative atmospheric humidity of approximately 80%.

The test is evaluated 7-9 days after the inoculation. 0% means an efficacy which corresponds to that of the untreated control while an efficacy of 100% means that no disease is observed.

Under these conditions, good (at least 70%) to total protection is observed at a dose of 500 ppm of active ingredient with the following compounds from table C:

TABLE C

| Example | Efficacy |
| --- | --- |
| 1 | 90 |
| 7 | 100 |
| 8 | 100 |
| 9 | 100 |
| 10 | 100 |
| 11 | 97 |
| 12 | 97 |
| 13 | 100 |
| 14 | 100 |
| 15 | 100 |

TABLE C-continued

| Example | Efficacy |
| --- | --- |
| 16 | 100 |
| 17 | 86 |
| 20 | 100 |
| 21 | 100 |
| 26 | 95 |
| 28 | 100 |
| 29 | 95 |
| 32 | 95 |
| 33 | 80 |
| 34 | 100 |
| 44 | 93 |
| 47 | 97 |
| 48 | 97 |
| 49 | 97 |
| 50 | 97 |
| 51 | 97 |
| 52 | 100 |
| 54 | 100 |
| 55 | 97 |
| 56 | 100 |
| 58 | 100 |
| 62 | 100 |
| 63 | 95 |
| 68 | 80 |
| 72 | 95 |
| 74 | 95 |
| 77 | 100 |
| 78 | 95 |
| 79 | 95 |
| 82 | 95 |
| 86 | 90 |
| 87 | 100 |
| 91 | 70 |
| 92 | 90 |
| 93 | 70 |
| 99 | 70 |
| 104 | 80 |
| 105 | 70 |
| 110 | 95 |
| 111 | 95 |
| 117 | 90 |

EXAMPLE D

In Vivo Preventive Test on *Pyrenophora teres* (Barley)—2nd Test

The active ingredients tested are prepared by homogenization in a mixture of acetone/tween/DMSO, and then diluted with water to obtain the desired active material concentration.

Barley plants ("Plaisant" variety), sown in starter cups on a 50/50 peat soil pozzolana substrate and grown at 22° C., are treated at the 1 leaf stage (10 cm height) by spraying with the active ingredient prepared as described above. Plants, used as controls, are treated with the mixture of acetone/tween/DMSO/water not containing the active material.

After 24 hours, the plants are contaminated by spraying the leaves with an aqueous suspension of *Pyrenophora teres* spores (12 000 spores per mL). The spores are collected from a 12-day-old culture. The contaminated barley plants are incubated for 48 hours at 20° C. and at 100% relative humidity, and then for 12 days at 20° C. at 70-80% relative humidity.

Grading (% of efficacy) is carried out 14 days after the contamination, in comparison with the control plants.

Under these conditions, good (at least 70%) to excellent (at least 90%) protection is observed at a dose of 500 ppm of active ingredient with the following compounds from table D:

TABLE D

| Example | Efficacy |
|---|---|
| 1 | 79 |
| 42 | 93 |
| 62 | 93 |

EXAMPLE E

In Vivo Preventive Test on *Septoria tritici* (Wheat)

The active ingredients tested are prepared by homogenization in a mixture of acetone/tween/DMSO, and then diluted with water to obtain the desired active material concentration.

Wheat plants ("Scipion" variety), sown in starter cups on a 50/50 peat soil pozzolana substrate and grown at 22° C., are treated at the 1 leaf stage (10 cm height) by spraying with the active ingredient prepared as described above. Plants, used as controls, are treated with the mixture of acetone/tween/DMSO/water not containing the active material.

After 24 hours, the plants are contaminated by spraying the leaves with an aqueous suspension of cryopreserved *Septoria tritici* spores (500 000 spores per mL). The contaminated wheat plants are incubated for 72 hours at 18° C. and at 100% relative humidity, and then for 21 days at 90% relative humidity.

Grading (% of efficacy) is carried out 24 days after the contamination, in comparison with the control plants.

Under these conditions, good (at least 70%) to total protection is observed at a dose of 500 ppm of active ingredient with the following compounds from table E:

TABLE E

| Example | Efficacy |
|---|---|
| 1 | 100 |
| 2 | 100 |
| 3 | 90 |
| 5 | 80 |
| 7 | 93 |
| 8 | 100 |
| 9 | 86 |
| 10 | 79 |
| 12 | 79 |
| 13 | 97 |
| 14 | 93 |
| 15 | 71 |
| 16 | 71 |
| 17 | 79 |
| 20 | 93 |
| 21 | 86 |
| 22 | 96 |
| 26 | 100 |
| 36 | 90 |
| 38 | 80 |
| 39 | 96 |
| 40 | 96 |
| 41 | 90 |
| 42 | 100 |
| 44 | 86 |
| 45 | 80 |
| 47 | 93 |
| 48 | 93 |
| 49 | 100 |
| 51 | 100 |
| 52 | 97 |
| 54 | 93 |
| 55 | 64 |
| 56 | 100 |
| 62 | 100 |
| 63 | 96 |

EXAMPLE F

In Vivo Preventive Test on *Puccinia recondita* (Brown Rust on Wheat)

The active ingredients tested are prepared by homogenization in a mixture of acetone/tween/DMSO, and then diluted with water to obtain the desired active material concentration.

Wheat plants ("Scipion" variety), sown in starter cups on a 50/50 peat soil pozzolana substrate and grown at 22° C., are treated at the 1 leaf stage (10 cm height) by spraying with the active ingredient prepared as described above. Plants, used as controls, are treated with the mixture of acetone/tween/DMSO/water not containing the active material.

After 24 hours, the plants are contaminated by spraying the leaves with an aqueous suspension of *Puccinia recondita* spores (100 000 spores per mL). The spores are collected from an infected plant and are suspended in water containing 2.5 mL/L of Tween 80 at 10%. The contaminated wheat plants are incubated for 24 hours at 20° C. and at 100% relative humidity, and then for 10 days at 20° C. and at 70-80% relative humidity.

Grading (% of efficacy) is carried out 12 days after the contamination, in comparison with the control plants.

Under these conditions, good (at least 70%) to total protection is observed at a dose of 500 ppm of active ingredient with the following compounds from table F:

TABLE F

| Example | Efficacy |
|---|---|
| 1 | 88 |
| 2 | 88 |
| 3 | 75 |
| 11 | 88 |
| 14 | 98 |
| 15 | 75 |
| 20 | 88 |
| 21 | 75 |
| 22 | 100 |
| 26 | 92 |
| 36 | 81 |
| 42 | 72 |
| 44 | 75 |
| 45 | 75 |
| 48 | 88 |
| 49 | 88 |
| 50 | 75 |
| 51 | 88 |
| 62 | 92 |
| 63 | 97 |

EXAMPLE G

In Vivo Preventive Test on *Alternaria brassicae* (Leaf Spot on Radish)

The active ingredients tested are prepared by homogenization in a mixture of acetone/tween/DMSO, and then diluted with water to obtain the desired active material concentration.

Radish plants ("Pernod Clair" variety), sown in starter cups on a 50/50 peat soil pozzolana substrate and grown at 17° C., are treated at the cotyledon stage by spraying with the active ingredient prepared as described above. Plants, used as controls, are treated with the mixture of acetone/tween/DMSO/water not containing the active material.

After 24 hours, the plants are contaminated by spraying the cotyledons with an aqueous suspension of *Alternaria brassicae* spores (50 000 spores per mL). The spores are collected from a 15-day-old culture. The contaminated radish plants are incubated at 20° C. and at 100% relative humidity.

Grading (% of efficacy) is carried out 6 days after the contamination, in comparison with the control plants.

Under these conditions, good (at least 75%) to total protection is observed at a dose of 500 ppm of active ingredient with the following compounds from table G:

TABLE G

| Example | Efficacy |
|---------|----------|
| 5 | 96 |
| 8 | 88 |
| 10 | 88 |
| 11 | 88 |
| 12 | 88 |
| 14 | 95 |
| 16 | 95 |
| 20 | 75 |
| 36 | 90 |
| 44 | 75 |
| 45 | 90 |
| 47 | 75 |
| 48 | 75 |
| 49 | 75 |
| 50 | 75 |
| 52 | 100 |
| 56 | 88 |

EXAMPLE H

In Vivo Preventive Test on *Botrytis cinerea* (Cucumber)

Solvent: 49 parts by weight of N,N-dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after this treatment, the plants are inoculated with an aqueous spore suspension of *Botrytis cinerea*. The plants remain for two days in an incubation cabinet at approximately 22° C. and a relative atmospheric humidity of 100%. Then the plants are placed in an incubation cabinet at approximately 14° C. and a relative atmospheric humidity of 96%.

The test is evaluated 5-6 days after the inoculation. 0% means an efficacy which corresponds to that of the untreated control while an efficacy of 100% means that no disease is observed.

Under these conditions, good (at least 70%) to total protection is observed at a dose of 500 ppm of active ingredient with the following compounds from table H:

TABLE H

| Example | Efficacy |
|---------|----------|
| 26 | 99 |
| 32 | 94 |
| 34 | 85 |
| 77 | 95 |
| 79 | 70 |
| 86 | 80 |
| 92 | 98 |
| 93 | 100 |
| 105 | 93 |

EXAMPLE I

In Vivo Preventive Test on *Botrytis cinerea* (Grey Mould)—$2^{nd}$ Test

The active ingredients tested are prepared by homogenization in a mixture of acetone/tween/DMSO and then diluted with water to obtain the desired active material concentration.

Gherkin plants ("Vert petit de Paris" variety), sown in starter cups on a 50/50 peat soil pozzolana substrate and grown at 24° C., are treated at the Z11 cotyledon stage by spraying with the active ingredient prepared as described above. Plants, used as controls, are treated with the mixture of acetone/tween/DMSO/water not containing the active material.

After 24 hours, the plants are contaminated by spraying the cotyledons with an aqueous suspension of cryopreserved *Botrytis cinerea* spores (50 000 spores per mL). The spores are suspended in a nutrient solution composed of 10 g/L of PDB, 50 g/L of D-Fructose, 2 g/L of $NH_4NO_3$ and 1 g/L of $KH_2PO4$. The contaminated gherkin plants are incubated at 17° C. and at 90% relative humidity.

Grading (% of efficacy) is carried out 4 to 5 days after the contamination, in comparison with the control plants.

Under these conditions, high (at least 85%) protection is observed at a dose of 500 ppm of active ingredient with the following compounds from table I:

TABLE I

| Example | Efficacy |
|---------|----------|
| 1 | 89 |
| 22 | 92 |

EXAMPLE J

In Vivo Preventive Test on *Pyricularia oryzae* (Rice Blast)

The active ingredients tested are prepared by homogenization in a mixture of acetone/tween/DMSO, and then diluted with water to obtain the desired active material concentration.

Rice plants ("Koshihikari" variety), sown in starter cups on a 50/50 peat soil pozzolana substrate and grown at 26° C., are treated at the 2 leaf stage (10 cm height) by spraying with the active ingredient prepared as described above. Plants, used as controls, are treated with the mixture of acetone/tween/DMSO/water not containing the active material.

After 24 hours, the plants are contaminated by spraying the leaves with an aqueous suspension of *Pyricularia oryzae* spores (40 000 spores per mL). The spores are collected from a 15-day-old culture and are suspended in water containing 2.5 g/L of gelatin. The contaminated rice plants are incubated at 25° C. and at 80% relative humidity.

Grading (% of efficacy) is carried out 6 days after the contamination, in comparison with the control plants.

Under these conditions, high (at least 80%) to excellent (at least 90%) protection is observed at a dose of 500 ppm of active ingredient with the following compounds from table J:

TABLE J

| Example | Efficacy |
|---------|----------|
| 45 | 83 |
| 46 | 92 |

EXAMPLE K

In Vivo Preventive Test on *Uromices appendiculatus* (Bean Rust)

The active ingredients tested are prepared by homogenization in a mixture of acetone/tween/DMSO, and then diluted with water to obtain the desired active material concentration.

Bean plants ("Saxa" variety), sown in starter cups on a 50/50 peat soil pozzolana substrate and grown at 24° C., are treated at the 2 leaf stage (9 cm height) by spraying with the active ingredient prepared as described above. Plants, used as controls, are treated with the mixture of acetone/tween/DMSO/water not containing the active material.

After 24 hours, the plants are contaminated by spraying the leaves with an aqueous suspension of *Uromyces appendiculatus* spores (150 000 spores per mL). The spores are collected from infected plants and are suspended in water containing 2.5 mL/L of Tween 80 at 10%. The contaminated bean plants are incubated for 24 hours at 20° C. and at 100% relative humidity, and then for 10 days at 20° C. and at 70-80% relative humidity.

Grading (% of efficacy) is carried out 11 days after the contamination, in comparison with the control plants.

Under these conditions, high (at least 80%) to total protection is observed at a dose of 500 ppm of active ingredient with the following compounds from table K:

TABLE K

| Example | Efficacy |
|---------|----------|
| 1 | 100 |
| 2 | 100 |
| 14 | 84 |
| 22 | 96 |

EXAMPLE L

In Vivo Preventive Test on *Leptosphaeria nodotrum* (Wheat)

Solvent: 49 parts by weight of N,N-dimethylformamide
Emulsifier: 1 part by weight of alkylaryl polyglycol ether
To produce a suitable preparation of active compound, 1 part by weight of active compound is mixed with the stated amounts of solvent and emulsifier, and the concentrate is diluted with water to the desired concentration.

To test for preventive activity, young plants are sprayed with a preparation of active compound at the stated rate of application. One day after this treatment, the plants are inoculated with an aqueous spore suspension of *Leptosphaeria nodorum*. The plants remain for 48 hours in an incubation cabinet at 22° C. and a relative atmospheric humidity of 100%. Then the plants are placed in a greenhouse at a temperature of approximately 22° C. and a relative atmospheric humidity of approximately 90%.

The test is evaluated 7-9 days after the inoculation. 0% means an efficacy which corresponds to that of the untreated control, while an efficacy of 100% means that no disease is observed.

Under these conditions, good (at least 70%) to excellent (at least 95%) protection is observed at a dose of 500 ppm of active ingredient with the following compounds from table L:

TABLE L

| Example | Efficacy |
|---------|----------|
| 26 | 80 |
| 32 | 90 |
| 34 | 80 |
| 62 | 70 |
| 72 | 80 |
| 74 | 70 |
| 77 | 95 |
| 79 | 90 |
| 92 | 80 |
| 93 | 80 |
| 99 | 70 |

The invention claimed is:
1. A compound of formula (I)

$$B \underset{Z^1 \ Z^2}{\overset{Z^3 \ Z^4}{\underset{}{\mid}}} \!\!\!\!\underset{n}{Si} \underset{Z^5 \ Z^6}{\overset{Z^7}{\mid}} N \underset{T}{\overset{}{\mid}} A \quad (I)$$

wherein
A represents a phenyl group that can be substituted by up to five groups R or a carbo-linked, unsaturated or partially saturated, 6-membered heterocyclyl group that can be substituted by up to four groups R;
T represents O or S;
n represents 0 or 1;
B represents a phenyl ring that can be substituted by up to 5 groups X which can be the same or different; a naphthyl ring that can be substituted by up to 7 groups X which can be the same or different;
X represents a halogen atom; nitro; cyano; isonitrile; hydroxy; amino; sulfanyl; pentafluoro-$\lambda^6$-sulfanyl; formyl; formyloxy; formylamino; substituted or non-substituted (hydroxyimino)-$C_1$-$C_8$-alkyl; substituted or non-substituted ($C_2$-$C_8$-alkoxyimino)-$C_1$-$C_8$alkyl; substituted or non-substituted ($C_2$-$C_8$-alkenyloxyimino)-$C_1$-$C_8$-alkyl; substituted or non-substituted ($C_2$-$C_8$-alkynyloxyimino)-$C_1$-$C_8$alalkyl; substituted or non-substituted (benzyloxyimino)-$C_1$-$C_8$-alkyl; carboxy; carbamoyl; N-hydroxycarbamoyl; substituted or non-substituted $C_1$-$C_8$-alkyl; $C_1$-$C_8$-halogenoalkyl having 1 to 5 halogen atoms; substituted or non-substituted $C_2$-$C_8$-alkeny; $C_2$-$C_8$-halogenoalkenyl having 1 to 5 halogen atoms; substituted or non-substituted $C_2$-$C_8$-alkynyl; $C_2$-$C_8$-halogenoalkynyl having 1 to 5 halogen atoms; substituted or non-substituted $C_1$-$C_8$-alkoxy; $C_1$-$C_8$-halogenoalkoxy having 1 to 5 halogen atoms; substituted or non-substituted $C_1$-$C_8$-alkylsulfanyl; $C_1$-$C_8$-halogenoalkylsulfanyl having 1 to 5 halogen atoms; substituted or non-substituted $C_1$-$C_8$-alkylsulfinyl; $C_1$-$C_8$-halogenoalkylsulfinyl having 1 to 5 halogen atoms; substituted or non-substituted $C_1$-$C_8$-alkylsulfonyl; $C_1$-$C_8$-halogenoalkylsulfonyl having 1 to 5 halogen atoms; substituted or non-substituted $C_1$-$C_8$-alkylamino; substituted or non-substituted di-$C_1$-$C_8$-alkylamino; substituted or non-substituted $C_2$-$C_8$-alkenyloxy; $C_2$-$C_8$-halogenoalkenyloxy having 1 to 5 halogen atoms; substituted or non-substituted $C_3$-$C_8$-alkynyloxy; $C_2$-$C_8$-halogenoalkynyloxy having 1 to 5 halogen atoms; substituted or non-substituted $C_3$-$C_7$-cycloalkyl; $C_3$-$C_7$-halogenocycloalkyl having 1 to 5 halogen atoms; substituted or non-substituted ($C_3$-$C_7$-cycloalkyl)-$C_1$-$C_8$-alkyl; substituted or non-substituted ($C_3$-$C_7$-cycloalkyl)-$C_2$-$C_8$alkenyl; substituted or non-substituted ($C_3$-$C_7$-cycloalkyl)-$C_2$-$C_8$-alkynyl; substituted or non-substituted tri($C_1$-$C_8$-alkyl)silyl; substituted or non-substituted tri($C_1$-$C_8$-alkyl)silyl-$C_1$-$C_8$-alkyl; substituted or non-substituted $C_1$-$C_8$-alkylcarbonyl; $C_1$-$C_8$-halogenoalkylcarbonyl having 1 to 5 halogen atoms; substituted or non-substituted $C_1$-$C_8$-alkylcarbonyloxy; $C_1$-$C_8$-halogenoalkylcarbonyloxy having 1 to 5 halogen atoms; substituted or non-substituted $C_1$-$C_8$-alkylcarbonylamino; $C_1$-$C_8$-halogenoalkyl-carbonylamino having 1 to 5 halogen atoms; substituted or non-substituted $C_1$-$C_8$-alkoxycarbonyl; $C_1$-$C_8$-halogenoalkoxycarbonyl having 1 to 5 halogen atoms; substituted or non-substituted $C_1$-$C_8$-alkyloxycarbonyloxy; $C_1$-$C_8$-halogenoalkoxycarbonyloxy having 1 to 5 halogen atoms; substituted or non-substituted $C_1$-$C_8$-alkylcarbamoyl; substituted or non-substituted di-$C_1$-$C_8$-alkylcarbamoyl; substituted or non-substituted $C_1$-$C_8$-alkylaminocarbonyloxy; substituted or non-substituted di-$C_1$-$C_8$-alkylaminocarbonyloxy; substituted or non-substituted N—($C_1$-$C_8$-alkyl)hydroxy carbamoyl; substituted or non-substituted $C_1$-$C_8$-alkoxycarbamoyl; substituted or non-substituted N—($C_1$-$C_8$-alkyl)-$C_1$-$C_8$-alkoxycarbamoyl; aryl that can be substituted by up to 6 groups Q which can be the same or different; $C_1$-$C_8$-arylalkyl that can be substituted by up to 6 groups Q which can be the same or different; $C_2$-$C_8$-arylalkenyl that can be substituted by up to 6 groups Q which can be the same or different; $C_2$-$C_8$-arylalkynyl that can be substituted by up to 6 groups Q which can be the same or different; aryloxy that can be substituted by up to 6 groups Q which can be the same or different; arylsulfanyl that can be substituted by up to 6 groups Q which can be the same or different; arylamino that can be substituted by up to 6 groups Q which can be the same or different; $C_1$-$C_8$-arylalkyloxy that can be substituted by up to 6 groups Q which can be the same or different; $C_1$-$C_8$-arylalkylsulfanyl that can be substituted by up to 6 groups Q which can be the same or different; or $C_1$-$C_8$-arylalkylamino that can be substituted by up to 6 groups Q which can be the same or different; or $Z^1$ and $Z^2$ independently represent a hydrogen atom; a halogen atom; cyano; substituted or non-substituted $C_1$-$C_8$-alkyl; $C_1$-$C_8$-halogenoalkyl having 1 to 5 halogen atoms; substituted or non-substituted $C_1$-$C_8$-alkoxy; substituted or non-substituted $C_1$-$C_8$-alkylsulfanyl; or substituted or non-substituted $C_1$-$C_8$-alkoxycarbonyl; or $Z^1$ and $Z^2$ are a $C_2$-$C_5$-alkylene group that can be substituted by up to four $C_1$-$C_8$-alkyl groups;

$Z^3$ and $Z^4$ independently represent a non-substituted $C_1$-$C_8$-alkyl;

$Z^5$ and $Z^6$ independently represent a hydrogen atom; a halogen atom; cyano; substituted or non-substituted $C_1$-$C_8$-alkyl; $C_1$-$C_8$-halogenoalkyl having 1 to 5 halogen atoms; substituted or non-substituted $C_1$-$C_8$-alkoxy; substituted or non-substituted $C_1$-$C_8$-alkylsulfanyl; or substituted or non-substituted $C_1$-$C_8$-alkoxycarbonyl; or $Z^5$ and $Z^6$ are a $C_2$-$C_5$-alkylene group that can be substituted by up to four $C_1$-$C_8$-alkyl groups;

$Z^7$ represents a hydrogen atom; a formyl group; a substituted or non-substituted $C_1$-$C_8$-alkyl; a substituted or non substituted $C_1$-$C_8$-alkoxy; a non-substituted $C_3$-$C_7$-cycloalkyl or a $C_3$-$C_7$-cycloalkyl substituted by up to 10 atoms or groups that can be the same or different and that can be selected in the list consisting of halogen atoms, cyano, $C_1$-$C_8$-alkyl, $C_1$-$C_8$-halogenoalkyl comprising up to 9 halogen atoms that can be the same or different, $C_1$-$C_8$-alkoxy, $C_1$-$C_8$-halogenoalkoxy comprising up to 9 halogen atoms that can be the same or different, $C_1$-$C_8$-alkoxycarbonyl, $C_1$-$C_8$-halogenoalkoxycarbonyl comprising up to 9 halogen atoms that can be the same or different, $C_1$-$C_8$-alkylaminocarbonyl and di-$C_1$-$C_8$-alkylaminocarbonyl;

Q independently represents a halogen atom; cyano; nitro; substituted or non-substituted $C_1$-$C_8$-alkyl; $C_1$-$C_8$-halogenoalkyl having 1 to 9 halogen atoms that can be the same or different; substituted or non-substituted $C_1$-$C_8$-alkoxy; $C_1$-$C_8$-halogenoalkoxy having 1 to 9 halogen atoms that can be the same or different; substituted or non-substituted $C_1$-$C_8$-alkylsulfanyl; $C_1$-$C_8$-halogenoalkylsulfanyl having 1 to 9 halogen atoms that can be the same or different; substituted or non-substituted tri($C_1$-$C_8$-alkyl)silyl; substituted or non-substituted tri ($C_1$-$C_8$-alkyl)silyl-$C_1$-$C_8$-alkyl; substituted or non-substituted ($C_1$-$C_8$-alkoxyimino)-$C_1$-$C_8$-alkyl; substituted or non-substituted (benzyloxyimino)-$C_1$-$C_8$-alkyl;

R independently represents hydrogen atom; halogen atom; nitro; cyano; hydroxy; amino; sulfanyl; pentafluoro-$\lambda^6$-sulfanyl; substituted or non-substituted ($C_1$-$C_8$-alkoxyimino)-$C_1$-$C_8$-alkyl; substituted or non-substituted (benzyloxyimino)-$C_1$-$C_8$-alkyl; substituted or non-substituted $C_1$-$C_8$-alkyl; $C_1$-$C_8$-halogenoalkyl having 1 to 5 halogen atoms; substituted or non-substituted $C_2$-$C_8$-alkenyl; $C_2$-$C_8$-halogenoalkenyl having 1 to 5 halogen atoms; substituted or non-substituted $C_2$-$C_8$-alkynyl; $C_2$-$C_8$-halogenoalkynyl having 1 to 5 halogen atoms; substituted or non-substituted $C_1$-$C_8$-alkoxy; $C_1$-$C_8$-halogenoalkoxy having 1 to 5 halogen atoms; substituted or non-substituted $C_1$-$C_8$-alkylsulfanyl; $C_1$-$C_8$-halogenoalkylsulfanyl having 1 to 5 halogen atoms; substituted or non-substituted $C_1$-$C_8$-alkylsulfinyl; $C_1$-$C_8$-halogcnoalkylsulfinyl having 1 to 5 halogen atoms; substituted or non-substituted $C_1$-$C_8$-alkylsulfonyl; $C_1$-$C_8$-halogenoalkylsulfonyl having 1 to 5 halogen atoms; substituted or non-substituted $C_1$-$C_8$-alkylamino; substituted or non-substituted di-$C_1$-$C_8$-alkylamino; substituted or non-substituted $C_2$-$C_8$-alkenyloxy; substituted or non-substituted $C_3$-$C_8$-alkynyloxy; substituted or non-substituted C$_3$-C$_7$-cycloalkyl; C$_3$-C$_7$-halogenocycloalkyl having 1 to 5 halogen atoms; substituted or non-substituted tri(C$_1$-C$_8$-alkyl)silyl; substituted or non-substituted C$_1$-C$_8$-alkylcarbonyl; C$_1$-C$_8$-halogenoalkylcarbonyl having 1 to 5 halogen atoms; substituted or non-substituted C$_1$-C$_8$alkoxycarbonyl; C$_1$-C$_8$-halogenoalkoxycarbonyl having 1 to 5 halogen atoms; substituted or non-substituted C$_1$-C$_8$-alkylcarbamoyl; substituted or non-substituted di-C$_1$-C$_8$-alkylcarbamoyl; phenoxy; phenylsulfanyl; phenylamino; benzyloxy; benzylsulfanyl; or benzylamino;

or its salts, N-oxides or optically active isomers.

2. A compound according to claim 1 wherein A is selected in the list consisting of:

a carbocycle of formula (A$^1$)

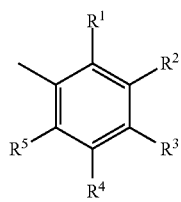

wherein:
R$^1$ represents a halogen atom; a hydroxy group; an amino group; a cyano group; substituted or non-substituted C$_1$-C$^5$-alkyl; C$_1$-C$_5$-halogenoalkyl comprising up to 5 halogen atoms that can be the same or different; substituted or non-substituted C$_1$-C$_5$-alkoxy; C$_1$-C$_5$-halogenoalkoxy comprising up to 5 halogen atoms that can be the same or different; substituted or non-substituted C$_1$-C$_5$-alkylsulfanyl or C$_1$-C$_5$-halogenoalkylsulfanyl comprising up to 5 halogen atoms that can be the same or different;

R$^2$ to R$^5$ that can be the same or different represent a hydrogen atom; a halogen atom; a hydroxy group; an amino group; a cyano group; substituted or non-substituted C$_1$-C$_5$-alkyl; C$_{1-5}$-halogenoalkyl comprising up to 5 halogen atoms that can be the same or different; substituted or non-substituted C$_1$-C$_5$-alkoxy; C$_1$-C$_5$-halogenoalkoxy comprising up to 5 halogen atoms that can be the same or different; substituted or non-substituted C$_1$-C$_5$-alkylsulfanyl or C$_{1-5}$-halogenoalkylsulfanyl comprising up to 5 halogen atoms that can be the same or different;

a heterocycle of formula (A$^2$)

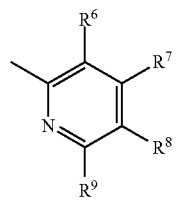

wherein :
R$^6$ represents a halogen atom; a cyano group; substituted or non-substituted C$_1$-C$_5$-alkyl; C$_1$-C$_5$-halogenoalkyl comprising up to 5 halogen atoms that can be the same or different; substituted or non-substituted C$_1$-C$_5$-alkoxy; C$_1$-C$_5$-halogenoalkoxy comprising up to 5 halogen atoms that can be the same or different; substituted or non-substituted C$_1$-C$_5$-alkylsulfanyl or C$_1$-C$_5$-halogenoalkylsulfanyl comprising up to 5 halogen atoms that can be the same or different;

R$^7$ to R$^9$ that can be the same or different represent a hydrogen atom; a halogen atom; a hydroxy group; an amino group; a cyano group; substituted or non-substituted C$_1$-C$_5$-alkyl; C$_{1-5}$-halogenoalkyl comprising up to 5 halogen atoms that can be the same or different; substituted or non-substituted C$_1$-C$_5$-alkoxy; C$_1$-C$_5$-halogenoalkoxy comprising up to 5 halogen atoms that can be the same or different; substituted or non-substituted C$_1$-C$_5$-alkylsulfanyl or C$_1$-C$_5$-halogenoalkylsulfanyl comprising up to 5 halogen atoms that can be the same or different;

a heterocycle of formula (A$^3$)

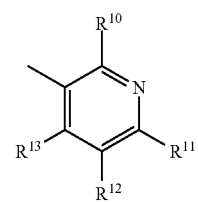

wherein:
R$^{10}$ represents a halogen atom; a hydroxy group; an amino group , a cyano group; substituted or non-substituted C$_1$-C$_5$-alkyl; C$_1$-C$_5$-halogenoalkyl comprising up to 5 halogen atoms that can be the same or different; substituted or non-substituted C$_1$-C$_5$-alkoxy; C$_1$-C$_5$-halogenoalkoxy comprising up to 5 halogen atoms that can be the same or different; substituted or non-substituted C$_1$-C$_5$-alkylsulfanyl or C$_1$-C$_5$-halogenoalkylsulfanyl comprising up to 5 halogen atoms that can be the same or different;

R$^{11}$ to R$^{13}$ that can be the same or different represent a hydrogen atom; a halogen atom; a hydroxy group; an amino group; a cyano group; substituted or non-substituted C$_1$-C$_5$-alkyl; C$_1$-C$_5$-halogenoalkyl comprising up to 5 halogen atoms that can be the same or different; substituted or non-substituted C$_1$-C$_5$-alkoxy; C$_1$-C$_5$-halogenoalkoxy comprising up to 5 halogen atoms that can be the same or different; substituted or non-substituted C$_1$-C$_5$-alkylsulfanyl or C$_1$-C$_5$-halogenoalkylsulfanyl comprising up to 5 halogen atoms that can be the same or different;

a heterocycle of formula (A$^4$)

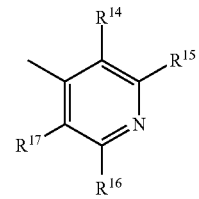

wherein:
R$^{14}$ represents a halogen atom; a cyano group; substituted or non-substituted C$_1$-C$_5$-alkyl; C$_1$-C$_5$-halogenoalkyl comprising up to 5 halogen atoms that can be the same or different; substituted or non-substituted $C_1$-$C_5$-alkoxy; $C_1$-$C_5$-halogenoalkoxy comprising up to 5 halogen atoms that can be the same or different; substituted or non-substituted $C_1$-$C_5$-alkylsulfanyl or $C_1$-$C_5$-halogenoalkylsulfanyl comprising up to 5 halogen atoms that can be the same or different;

$R^{15}$ to $R^{17}$ that can be the same or different represent a hydrogen atom; a halogen atom; a hydroxy group; an amino group; a cyano group; substituted or non-substituted $C_1$-$C_5$-alkyl;

$C_1$-$C_5$-halogenoalkyl comprising up to 5 halogen atoms that can be the same or different; substituted or non-substituted $C_1$-$C_5$-alkoxy; $C_1$-$C_5$-halogenoalkoxy comprising up to 5 halogen atoms that can be the same or different; substituted or non-substituted $C_1$-$C_5$-alkylsulfanyl or $C_1$-$C_5$-halogenoalkylsulfanyl comprising up to 5 halogen atoms that can be the same or different;

a heterocycle of formula ($A^5$)

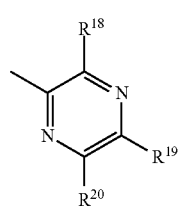

wherein:

$R^{18}$ represents a halogen atom; a cyano group; substituted or non-substituted $C_1$-$C_5$-alkyl; $C_1$-$C_5$-halogenoalkyl comprising up to 5 halogen atoms that can be the same or different; substituted or non-substituted $C_1$-$C_5$-alkoxy; $C_1$-$C_5$-halogenoalkoxy comprising up to 5 halogen atoms that can be the same or different; substituted or non-substituted $C_1$-$C_5$-alkylsulfanyl or $C_1$-$C_5$-halogenoalkylsulfanyl comprising up to 5 halogen atoms that can be the same or different;

$R^{19}$ and $R^{20}$ that can be the same or different represent a hydrogen atom; a halogen atom; substituted or non-substituted $C_1$-$C_5$-alkyl or $C_1$-$C_5$-halogenoalkyl comprising up to 5 halogen atoms that can be the same or different;

a heterocycle of formula ($A^6$)

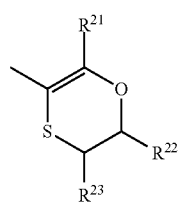

wherein:

$R^{21}$ represents a halogen atom; a cyano group; substituted or non-substituted $C_1$-$C_5$-alkyl; $C_1$-$C_5$-halogenoalkyl comprising up to 5 halogen atoms that can be the same or different; substituted or non-substituted $C_1$-$C_5$-alkoxy; $C_1$-$C_5$-halogenoalkoxy comprising up to 5 halogen atoms that can be the same or different; substituted or non-substituted $C_1$-$C_5$-alkylsulfanyl or $C_1$-$C_5$-halogenoalkylsulfanyl comprising up to 5 halogen atoms that can be the same or different;

$R^{22}$ and $R^{23}$ that can be the same or different represent a hydrogen atom; substituted or non-substituted $C_1$-$C_5$-alkyl or $C_1$-$C_5$-halogenoalkyl comprising up to 5 halogen atoms that can be the same or different;

a heterocycle of formula ($A^7$)

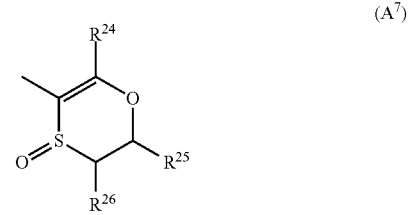

wherein:

$R^{24}$ represents a halogen atom; a cyano group; substituted or non-substituted $C_1$-$C_5$-alkyl; $C_1$-$C_5$-halogenoalkyl comprising up to 5 halogen atoms that can be the same or different; substituted or non-substituted $C_1$-$C_5$-alkoxy; $C_1$-$C_5$-halogenoalkoxy comprising up to 5 halogen atoms that can be the same or different; substituted or non-substituted $C_1$-$C_5$-alkylsulfanyl or $C_1$-$C_5$-halogenoalkylsulfanyl comprising up to 5 halogen atoms that can be the same or different;

$R^{25}$ and $R^{26}$ that can be the same or different represent a hydrogen atom; substituted or non-substituted $C_1$-$C_5$-alkyl or $C_1$-$C_5$-halogenoalkyl comprising up to 5 halogen atoms that can be the same or different;

a heterocycle of formula ($A^8$)

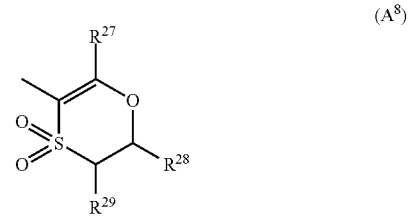

wherein:

$R^{27}$ represents a halogen atom; a cyano group; substituted or non-substituted $C_1$-$C_5$-alkyl; C-$C_5$-halogenoalkyl comprising up to 5 halogen atoms that can be the same or different; substituted or non-substituted $C_1$-$C_5$-alkoxy; $C_1$-$C_5$-halogenoalkoxy comprising up to 5 halogen atoms that can be the same or different; substituted or non-substituted $C_1$-$C_5$-alkylsulfanyl or $C_1$-$C_5$-halogenoalkylsulfanyl comprising up to 5 halogen atoms that can be the same or different;

$R^{28}$ and $R^{29}$ that can be the same or different represent a hydrogen atom; substituted or non-substituted $C_1$-$C_5$-alkyl or $C_1$-$C_5$-halogenoalkyl comprising up to 5 halogen atoms that can be the same or different;

a heterocycle of formula ($A^9$)

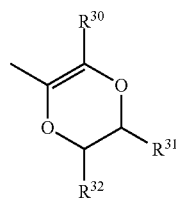

(A⁹)

wherein:

$R^{30}$ represents a halogen atom; a cyano group; substituted or non-substituted $C_1$-$C_5$-alkyl; $C_1$-$C_5$-halogenoalkyl comprising up to 5 halogen atoms that can be the same or different; substituted or non-substituted $C_1$-$C_5$-alkoxy; $C_1$-$C_5$-halogenoalkoxy comprising up to 5 halogen atoms that can be the same or different; substituted or non-substituted $C_1$-$C_5$-alkylsulfanyl or $C_1$-$C_5$-halogenoalkylsulfanyl comprising up to 5 halogen atoms that can be the same or different;

$R^{31}$ and $R^{32}$ that can be the same or different represent a hydrogen atom; substituted or non-substituted $C_1$-$C_5$-alkyl or $C_1$-$C_5$-halogenoalkyl comprising up to 5 halogen atoms that can be the same or different; and a heterocycle of formula) $(A^{10})$

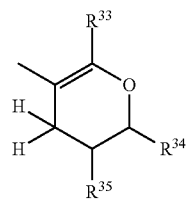

(A¹⁰)

wherein:

$R^{33}$ represents a halogen atom; a cyano group; substituted or non-substituted $C_1$-$C_5$-alkyl; $C_1$-$C_5$-halogenoalkyl comprising up to 5 halogen atoms that can be the same or different; substituted or non-substituted $C_1$-$C_5$-alkoxy; $C_1$-$C_5$-halogenoalkoxy comprising up to 5 halogen atoms that can be the same or different; substituted or non-substituted $C_1$-$C_5$-alkylsulfanyl or $C_1$-$C_5$-halogenoalkylsulfanyl comprising up to 5 halogen atoms that can be the same or different;

$R^{34}$ and $R^{35}$ that can be the same or different represent a hydrogen atom; substituted or non-substituted $C_1$-$C_5$-alkyl or $C_1$-$C_5$-halogenoalkyl comprising up to 5 halogen atoms that can be the same or different.

3. A compound according to claim 2 wherein A is selected in the list consisting of $A^1$; $A^3$; $A^5$ and $A^6$.

4. A compound according to claim 2 wherein A represents $A^1$ wherein $R^1$ represents a halogen atom, substituted or non-substituted $C_1$-$C_5$-alkyl, $C_1$-$C_5$-halogenoalkyl comprising up to 5 halogen atoms that can be the same or different and $R^2$ to $R^5$ represent a hydrogen atom.

5. A compound according to claim 2 wherein A represents $A^3$ wherein $R^{10}$ represents a halogen atom or $C_1$-$C_5$-halogenoalkyl comprising up to 5 halogen atoms that can be the same or different and $R^{11}$ to $R^{13}$ represent a hydrogen atom.

6. A compound according to claim 2 wherein A represents $A^5$ wherein $R^{18}$ represents a halogen atom or $C_1$-$C_5$-halogenoalkyl comprising up to 5 halogen atoms that can be the same or different and $R^{19}$ and $R^{20}$ represent a hydrogen atom.

7. A compound according to claim 2 wherein A represents $A^6$ wherein $R^{21}$ represents a non-substituted $C_1$-$C_5$-alkyl or $C_1$-$C_5$-halogenoalkyl comprising up to 5 halogen atoms that can be the same or different and $R^{22}$ and $R^{23}$ represent a hydrogen atom.

8. A compound according to claim 1 wherein T represents O.

9. A compound according to claim 1 wherein X independently represents a halogen atom; substituted or non-substituted $C_1$-$C_8$-alkyl; $C_1$-$C_8$-halogenoalkyl comprising up to 5 halogen atoms that can be the same or different; substituted or non-substituted tri($C_1$-$C_8$alkyl)silyl; substituted or non-substituted $C_1$-$C_8$-alkoxy or $C_1$-$C_8$-halogenoalkoxy comprising up to 5 halogen atoms that can be the same or different.

10. A compound according to claim 1 wherein $Z^1$, $Z^2$, $Z^5$ and $Z^6$ independently represent a hydrogen atom, a substituted or non-substituted $C_1$-$C_8$-alkyl or a substituted or non-substituted $C_1$-$C_8$-alkoxy.

11. A compound according to claim 1 wherein $Z^7$ represents a hydrogen atom, a non-substituted $C_3$-$C_7$ cycloalkyl or a $C_3$-$C_7$ cycloalkyl substituted by up to 10 groups or atoms that can be the same or different and that can be selected in the list consisting of halogen atoms, $C_1$-$C_8$-alkyl, $C_1$-$C_8$-halogenoalkyl comprising up to 9 halogen atoms that can be the same or different, $C_1$-$C_8$-alkoxy or $C_1$-$C_8$-halogenoalkoxy comprising up to 9 halogen atoms that can be the same or different.

12. A compound according to claim 1 wherein R independently represents a hydrogen atom; halogen atom; cyano; substituted or non-substituted $C_1$-$C_8$-alkylamino; substituted or non-substituted di-$C_1$-$C_8$-alkylamino; substituted or non-substituted tri($C_1$-$C_8$-alkyl)silyl; substituted or non-substituted $C_1$-$C_8$-alkyl; $C_1$-$C_8$-halogenoalkyl comprising up to 5 halogen atoms that can be the same or different; substituted or non-substituted $C_1$-$C_8$-alkoxy; $C_1$-$C_8$-halogenoalkoxy comprising up to 5 halogen atoms that can be the same or different; substituted or non-substituted $C_1$-$C_8$-alkylsulfanyl; amino; hydroxyl; nitro; substituted or non-substituted $C_1$-$C_8$-alkoxycarbonyl; substituted or non-substituted $C_2$-$C_8$-alkynyloxy.

13. A fungicide composition comprising, as an active ingredient, an effective amount of a compound of formula (I) according to claim 1 and an agriculturally acceptable support, carrier or filler.

14. A method for controlling phytopathogenic fungi of crops, characterized in that an agronomically effective and substantially non-phytotoxic quantity of a compound according to claim 1 is applied to the soil where plants grow or are capable of growing, to the leaves and/or the fruit of plants or to the seeds of plants.

15. A method for controlling phytopathogenic fungi of crops, characterized in that an agronomically effective and substantially non-phytotoxic quantity of a fungicide composition according to claim 13 is applied to the soil where plants grow or are capable of growing, to the leaves and/or the fruit of plants or to the seeds of plants.

* * * * *